United States Patent
Kuhn et al.

(10) Patent No.: US 11,154,249 B2
(45) Date of Patent: Oct. 26, 2021

(54) SENSING FOR HEALTH STATUS MANAGEMENT

(71) Applicant: Medtronic, Inc., Minneapolis, MN (US)

(72) Inventors: Jonathan L. Kuhn, Ham Lake, MN (US); James K. Carney, Roseville, MN (US); Shantanu Sarkar, Roseville, MN (US)

(73) Assignee: Medtronic, Inc., Minneapolis, MN (US)

(*) Notice: Subject to any disclaimer, the term of this patent is extended or adjusted under 35 U.S.C. 154(b) by 4 days.

(21) Appl. No.: 15/969,407

(22) Filed: May 2, 2018

(65) Prior Publication Data

US 2019/0336077 A1    Nov. 7, 2019

(51) Int. Cl.
*A61B 5/00* (2006.01)
*A61B 5/0205* (2006.01)
(Continued)

(52) U.S. Cl.
CPC ............ *A61B 5/686* (2013.01); *A61B 5/0205* (2013.01); *A61B 5/076* (2013.01); *A61B 5/1459* (2013.01); *A61B 5/14552* (2013.01); *A61B 5/287* (2021.01); *A61B 5/486* (2013.01); *A61B 5/7275* (2013.01); *A61B 5/7282* (2013.01); *A61B 5/02125* (2013.01); *A61B 5/02405* (2013.01); *A61B 5/0538* (2013.01); *A61B 5/08* (2013.01); *A61N 1/362* (2013.01); *A61N 1/3756* (2013.01); *A61N 1/3956* (2013.01); *G16H 40/63* (2018.01)

(58) Field of Classification Search
CPC ..... A61B 5/686; A61B 5/0205; A61B 5/7275; A61B 5/08
See application file for complete search history.

(56) References Cited

U.S. PATENT DOCUMENTS 5,788,643 A   8/1998  Feldman
6,336,903 B1  1/2002  Bardy
(Continued)

OTHER PUBLICATIONS

Bernard, Michael L. "Pacing Without Wires: Leadless Cardiac Pacing." The Ochsner journal vol. 16,3 (2016): 238-42 (Year: 2016).*

(Continued)

*Primary Examiner* — Gary Jackson
*Assistant Examiner* — Anant A Gupta
(74) *Attorney, Agent, or Firm* — Shumaker & Sieffert, P.A.

(57) ABSTRACT

In some examples, determining a health status includes using an implantable medical device configured for subcutaneous implantation and comprising at least one optical sensor. Processing circuitry of a system comprising the device may determine, for a patient, a current tissue oxygen saturation value based on a first signal received from the at least one optical sensor and a current pulsatile oxygen saturation value based on a second signal received from the at least one optical sensor. The processing circuitry may further compare the current tissue oxygen saturation and current pulsatile oxygen saturation values to corresponding baseline values, determine corresponding heart failure and pulmonary statuses of the patient based on the comparisons, and determine the health status of the patient based on the statuses.

33 Claims, 13 Drawing Sheets

(51) Int. Cl.

| | |
|---|---|
| *A61B 5/07* | (2006.01) |
| *A61B 5/1455* | (2006.01) |
| *A61B 5/1459* | (2006.01) |
| *A61B 5/287* | (2021.01) |
| *G16H 40/63* | (2018.01) |
| *A61B 5/021* | (2006.01) |
| *A61B 5/024* | (2006.01) |
| *A61B 5/0538* | (2021.01) |
| *A61B 5/08* | (2006.01) |
| *A61N 1/362* | (2006.01) |
| *A61N 1/375* | (2006.01) |
| *A61N 1/39* | (2006.01) |

(56) References Cited

U.S. PATENT DOCUMENTS

| | | | |
|---|---|---|---|
| 6,480,733 B1 | 11/2002 | Turcott | |
| 7,029,447 B2 | 4/2006 | Rantala | |
| 7,460,909 B1 | 12/2008 | Koh et al. | |
| 8,062,227 B2 | 11/2011 | Cho et al. | |
| 8,323,189 B2 * | 12/2012 | Tran | A61B 5/0024 600/300 |
| 8,346,332 B2 * | 1/2013 | Kuhn | A61N 1/36557 600/323 |
| 8,380,303 B2 * | 2/2013 | Rosenberg | A61B 5/0538 607/2 |
| 8,491,485 B2 | 7/2013 | Czygan et al. | |
| 8,515,537 B2 * | 8/2013 | Cinbis | A61N 1/36557 607/17 |
| 8,708,924 B2 | 4/2014 | Wariar et al. | |
| 8,821,404 B2 | 9/2014 | Thakur et al. | |
| 9,174,054 B1 * | 11/2015 | Nabutovsky | A61B 5/4836 |
| 9,662,073 B2 * | 5/2017 | Zhang | G16H 50/30 |
| 9,669,218 B2 | 6/2017 | Libbus et al. | |
| 10,610,132 B2 | 4/2020 | Gunderson et al. | |
| 2008/0228090 A1 | 9/2008 | Wariar et al. | |
| 2009/0062667 A1 | 3/2009 | Fayram et al. | |
| 2009/0326350 A1 | 12/2009 | Kracker | |
| 2010/0041970 A1 * | 2/2010 | Hedberg | A61N 1/3702 600/333 |
| 2011/0009754 A1 | 1/2011 | Wenzel et al. | |
| 2011/0098771 A1 | 4/2011 | Thakur et al. | |
| 2011/0172504 A1 * | 7/2011 | Wegerich | A61B 5/0205 600/301 |
| 2011/0230771 A1 | 9/2011 | Koh et al. | |
| 2012/0109243 A1 | 5/2012 | Hettrick et al. | |
| 2013/0116578 A1 | 5/2013 | An et al. | |
| 2013/0123617 A1 | 5/2013 | Sola i Caros et al. | |
| 2014/0195168 A1 * | 7/2014 | Shaikh | G16H 50/20 702/19 |
| 2014/0221849 A1 | 8/2014 | Farringdon et al. | |
| 2014/0276928 A1 | 9/2014 | Vanderpool et al. | |
| 2014/0330172 A1 | 11/2014 | Jovanov et al. | |
| 2016/0310031 A1 | 10/2016 | Sarkar et al. | |
| 2017/0156604 A1 | 6/2017 | Zhang et al. | |
| 2017/0209053 A1 | 7/2017 | Pantelopoulos et al. | |
| 2017/0231568 A1 | 8/2017 | An et al. | |
| 2017/0238812 A1 | 8/2017 | Mas | |
| 2017/0265782 A1 | 9/2017 | Vollmer | |
| 2017/0281095 A1 * | 10/2017 | An | A61B 5/201 |
| 2017/0347969 A1 * | 12/2017 | Thakur | A61B 5/7246 |
| 2018/0035898 A1 | 2/2018 | Gunderson | |
| 2018/0035920 A1 | 2/2018 | Gunderson et al. | |
| 2018/0035924 A1 | 2/2018 | Gunderson et al. | |
| 2018/0035956 A1 | 2/2018 | Gunderson et al. | |
| 2018/0055386 A1 | 3/2018 | Zielinski et al. | |
| 2018/0177486 A1 | 6/2018 | Gifford, III et al. | |
| 2019/0133457 A1 | 5/2019 | Sun et al. | |
| 2019/0336076 A1 | 11/2019 | Kuhn et al. | |

OTHER PUBLICATIONS

Yancy, MD et al. "2013 ACCF/AHA Guideline for the Management of Heart Failure." Circulation. May 2013;128: pp. e240-e327.

Yancy, MD et al. "2016 ACC/AHA/HFSA Focused Update on New Pharmacological Therapy for Heart Failure: An Update of the 2013 ACCF/AHA Guideline for the Management of Heart Failure." Journal of Cardiac Failure vol. 22 No. 9, Sep. 2016, pp. 659-669.

Ponikowski et al. "2016 ESC Guidelines for the diagnosis and treatment of acute and chronic heart failure." European Heart Journal, May 2016, 37, 2129-2200.

Bennett, et al., "Development of Implantable Devices for Continuous Ambulatory Monitoring of Central Hemodynamic Values in Heart Failure Patients." Pace, vol. Jun. 28. 2005, pp. 573-584.

Forrester, et al., "Correlative Classification of Clinical and Hemodynamic Function after Acute Myocardial Infarction." the American Journal of Cardiology, vol. 39, Issue 2, Feb. 1977, pp. 137-145.

Nohria, MD, et al. "Clinical Assessment Identifies Hemodynamic Profiles that Predict Outcomes in Patients Admitted with Heart Failures," J. Am. Col Cardiology, vol. 41, No. 10, May 21, 2003, 1797-1804.

"Causes of Hypoperfusion state," Right Diagnosis, last updated Aug. 13, 2015, accessed from http://www.rightdiagnosis.com/symptoms/hypoperfusion_state/causes.htm, 2 pp.

"VCSEL-ULM763-SingleMODE_TO5_v13," Philips, accessed on Nov. 7, 2017, accessed from http://www.photonics.philips.com/pdf/VCSEL-ULM763-SingleMode_TO5.pdf, 2 pp.

Hogan et al., "The Utility of Microvascular Perfusion Assessment in Heart Failure: A Pilot Study," J. Cardiac Failure vol. 11, No. 9, Jul. 2005, pp. 713-719.

Myers, et al., "Tissue hemoglobin index: a non-invasive optical measure of total tissue hemoglobin," Critical Care, vol. 13, Suppl. 5, Nov. 30, 2009, 13 pp.

Hogan et al., "Quantitative tissue hemoglobin oxygen saturation measurement in decompensated heart failure," J. Cardiothoracic-Renal Research May 2006 1, 153-157.

Podbregar, et al., "Skeletal muscle oxygen saturation does not estimate mixed venous oxygen saturation in patients with severe left heart failure and additional severe sepsis or spectic shock," Critical Care Jan. 2007, 11: R6.

Fontaine, et al., "Reflectance-Based Pulse Oximeter for the Chest and Wrist," A Major Qualifying Project Report. Worchester Polytechnic Institute, accessed on Nov. 7, 2017, 96 pp.

Charach, et al., "Internal Thoracic Impedance—A Useful Method for Expedient Detection and Convenient Monitoring of Pleural Effusion," PLOS One, published Apr. 28, 2015, 14 pp.

Sarkar, "A Dynamic Risk Score to Identify Increased Risk for Heart Failure Decompensation." IEEE Transactions on Biomedical Engineering, vol. 60, No. 1, Jan. 2013, pp. 147-150.

Virani, et al. "Integrated Diagnostics for Heart Failure: The Triage-HF Study." Canadian Journal of Cardiology. Oct. 2016, vol. 32, Issue 10, Supplement 1, pp. S148-S149.

Study: "Integrated Diagnostics Driven Diuretic and Chronic Medication Management for Heart Failure". Sponsor: Medtronic Cardiac Rhythm and Heart Failure. https://clinicaltrials.gov/ct2/show/NCT02698241, lasted updated Apr. 2, 2018, 6 pp.

Cowie, et al., "Development and validation of an integrated diagnostic algorithm derived from parameters monitored in implantable devices for identifying patients at risk for heart failure hospitalization in an ambulatory setting," European Heart Journal; 43, published online Mar. 19, 2013, pp. 2472-2480.

Abay et al., "Reflectance Photoplethysmography as Noninvasive Monitoring of Tissue Blood Perfusion," IEEE Transactions on Biomedical Engineering, vol. 62, No. 9, Sep. 2015, pp. 2187-2195.

International Search Report and Written Opinion of International Application No. PCT/US2019/030202, dated Jul. 29, 2019, 10 pp.

U.S. Appl. No. 15/969,369, filed May 2, 2018, by Kuhn et al.

J. Fiala et al., "Implantable Reflectance Pulse Transit Time Blood Pressure Sensor with Oximetry Capability," Proceedings SPIE 7513, 2009 International Conference on Optical Instruments and Technology, vol. 7715, Apr. 28, 2010, 6 pages.

(56) References Cited

OTHER PUBLICATIONS

Edlow et al., "The effects o healthy aging on cerebral hemodynamic responses to posture change," Physiological Measurement, vol. 31, No. 4, Feb. 2010, 19 pp.

U.S. Appl. No. 17/086,653, Naming Inventors: Gunderson et al., filed Nov. 2, 2020.

Gholamhosseini et al., "Smartphone-based blood pressure monitoring for falls risk assessment: techniques and technologies," Human Monitoring, Smart Health and Assisted Living: Techniques and Technologies, May 31, 2017, pp. 203-215.

International Search Report and Written Opinion of International Application No. PCT/US2020/058624, dated Feb. 8, 2021, 12 pp.

International Search Report and Written Opinion of International Application No. PCT/US2019/030166, dated Jul. 24, 2019, 14 pp.

\* cited by examiner

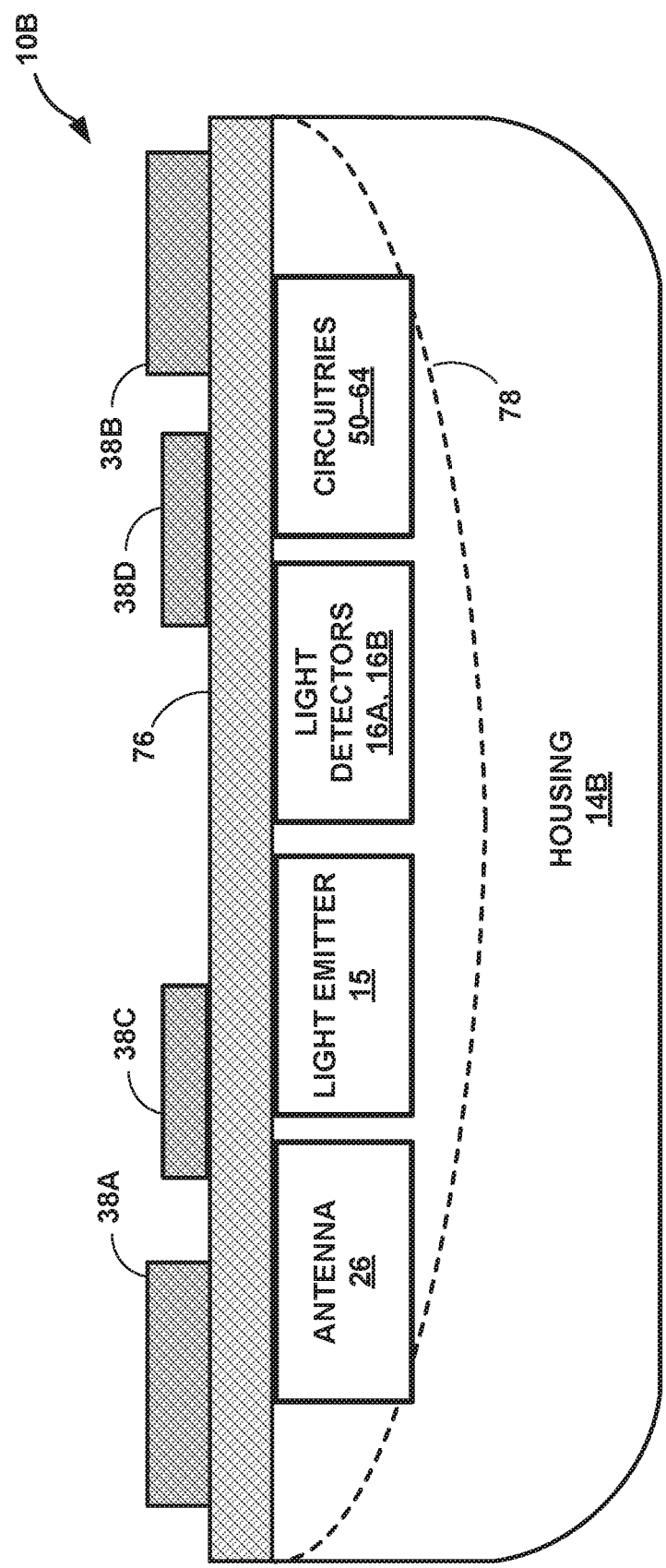

SENSING FOR HEALTH STATUS MANAGEMENT

TECHNICAL FIELD

The disclosure relates generally to medical device systems and, more particularly, medical device systems configured to monitor patient parameters.

BACKGROUND

Some types of implantable medical devices (IMDs) may be used to monitor one or more physiological parameters of a patient, such as physiological parameters associated with cardiac or pulmonary function. Such IMDs may include, or may be part of a system that includes, sensors that detect signals associated with such physiological parameters; e.g., tissue impedance or oxygen levels. Values determined based on such signals may be used to assist in detecting changes in medical conditions, in evaluating the efficacy of a therapy, or in generally evaluating patient health.

Implantable devices that monitor physiological parameters related to a medical condition of a patient may evaluate values associated with the physiological parameters, such as to determine whether the values exceed a threshold or have changed. Values that exceed a threshold or that have changed may indicate that a therapy being administered to the patient is not effectively managing the patient's medical condition.

SUMMARY

In general, this disclosure is directed to techniques for determining a health status of a patient, such as a patient diagnosed with a heart failure condition. Such techniques may include performing assessments associated with aspects of a patient's cardiac function, lung function, and blood function, and determining a medical profile of the patient based on the outcome of the assessments. Such medical profiles may indicate heart failure, pulmonary, and anemia statuses of the patient (e.g., whether the patient's cardiac, lung, and blood functions are stable or deteriorating), and may help guide therapy selection. Additionally, such profiles may enable differential diagnosis between two or more of a cardiac condition, a lung condition, and anemia, particularly where such conditions may present with similar symptoms.

A patient initially may be diagnosed with a heart failure condition after presenting at a healthcare facility with acute heart failure symptoms, such as shortness of breath or dyspnea. When evaluating such a patient for heart failure conditions, a clinician may perform assessments associated with aspects of the patient's cardiac function, such as preload, afterload, and vascular resistance, by observing surrogate parameters. For example, in order to assess preload (a measure of heart filling capacity), a clinician may observe the patient for signs of congestion, such as peripheral edema, jugular venous dilatation, ascites, or others. To assess afterload (a measure of heart contractility and output), a clinician may observe the patient for signs of inadequate peripheral perfusion, such as cold sweated extremities, oliguria, mental confusion, and dizziness. Vascular resistance may be approximated using blood pressure measurements, or by observing the patient for signs of vasoconstriction, such as numbness and tingling in extremities. Based on the combined outcome of these assessments, a clinician may identify a hemodynamic profile of the patient (e.g., congested+adequately perfused+vasoconstricted), which may signify a type of the patient's heart failure condition.

In some examples, the clinician also may assess the patient's lung and blood functions to evaluate the patient for pulmonary disorders or anemia, which in some cases may be co-morbid with heart failure conditions and may present with similar symptoms, such as shortness of breath (dyspnea) or fatigue. In order to evaluate the patient for pulmonary disorders, the clinician may perform assessments associated with aspects of the patient's lung function, such as arterial blood oxygenation. For example, the clinician may assess arterial blood oxygenation by observing the patient for surrogate parameter of hypoxia, which may be characterized by cyanosis, rapid breathing, or low pulsatile oxygen saturation as measured by a pulse oximetry device applied to the patient's periphery. In order to evaluate the patient for anemia, the clinician may perform assessments associated with aspects of the patient's blood function, such as hemoglobin concentration. In some examples, the clinician may assess hemoglobin concentration by observing the patient for the surrogate parameters of fatigue, weakness, or dizziness, or by observing results of a laboratory blood test.

Based on the combined outcome of these assessments, a clinician may identify a health status of the patient (e.g., positive for congestive heart failure and negative for pulmonary disorders and anemia), and prescribe treatment in accordance with the patient's health status. For example, such treatment may include drug therapy to compensate for a loss of cardiac function caused by the patient's heart failure condition. Thereafter, the patient may be discharged from the healthcare facility with instructions for continuing the prescribed therapy and scheduling regular clinician visits.

For one or more reasons, however, one or more of a patient's medical conditions, which may be in a state of chronic but stable compensation when adequately managed by therapy, may become unstable and acutely decompensate, that is, no longer adequately be managed by therapy between clinician visits. For example, the progressive nature of heart disease may cause a patient to experience worsening congestion between visits, which may be caused by physiological cardiac remodeling and changes in cardiac function that occur in the progression of heart failure. In some examples, effects of the changes in cardiac function associated with progressing heart failure may lead to changes in lung and/or blood functions. Such changes may be circular in nature, such that changes in lung and/or blood functions caused by worsening cardiac function may in turn cause further worsening of cardiac function.

For example, the development or worsening of congestion in a patient with a heart failure condition may decrease the ability of the lungs to oxygenate the patient's arterial blood, which in turn may lead to inadequate tissue perfusion. In some such cases, the patient's body may attempt to compensate for inadequate tissue perfusion by increasing vasoconstriction, which in turn may increase congestion, leading to a cycle of worsening cardiac and lung function. Additionally, or alternatively, the development or worsening of congestion and a resultant increase in vasoconstriction may increase strain on the kidneys, which may result in the development of renal failure, which in turn may lead to the development of anemia. In some such cases, the patient's body may attempt to compensate for the anemia by increasing heart rate, which may increase strain on the heart, leading to a cycle of worsening cardiac and blood function.

In any such cases, the patient may become symptomatic and acutely decompensate between visits. In some examples, such acute decompensation may lead to hospitalization or other adverse medical events. However, by the time the patient receives treatment for his or her symptoms at a healthcare facility, cycles of worsening physiological function may have caused further progression of the patient's heart failure condition or the development of additional medical conditions such as a pulmonary disorder or chronic anemia. Such effects of decompensation may lead to a decline in the patient's quality of life or other undesirable clinical outcomes.

Moreover, evaluation and treatment of the symptomatic acutely decompensated patient may be complicated by the fact that changes in different physiological functions each may result in the same symptom. For example, the symptom of shortness of breath may be caused by any one or more of changes in cardiac function, lung function, or blood function (i.e., anemia). Thus, it may be desirable to differentiate between shortness of breath caused by worsening anemia caused by a reduction in hematocrit and less capacity to carry oxygen, shortness of breath caused by fluid overload (i.e., congestion), and shortness of breath caused by respiratory failure (e.g., chronic obstructed pulmonary disease (COPD)), as each condition may lead to an increase in oxygen demand and shortness of breath.

Ongoing monitoring of physiological functions associated with a patient's condition (e.g., cardiac, lung, and blood) may enable early detection of changes in such physiological functions, before the changes lead to symptoms, acute decompensation, and/or the progression or development of one or more medical conditions. In the event that the patient nonetheless becomes symptomatic, such ongoing monitoring may enable identification of the physiological functions whose changes are causing symptom. Consequently, clinical outcomes for patients would benefit from methods for monitoring a patient's cardiac, lung, and blood functions between clinician visits, which in turn may enable prediction of a likelihood that progression of a disease state and hospitalization may occur or early identification of the cause of symptoms. In response to such information, a patient's treatment may be adjusted (e.g., by modifying a drug regimen), which may help reduce the patient's likelihood of acute decompensation, hospitalization, or the development of additional medical conditions.

However, assessment of parameters related to heart, lung and blood function, such as assessment of a patient's heart failure status based on observations of the surrogate parameters of congestion (i.e., hypervolemia), peripheral perfusion, and vascular resistance, may be limited to clinical or hospital settings. For example, such assessments may require medical expertise unavailable to the patient in a non-clinical environment. Thus, methods for updating a patient's hemodynamic profile between clinician visits may be performed using one or more medical devices, such as the subcutaneously-implantable medical devices described herein.

Accordingly, techniques described herein may include automatically detecting and monitoring parameters associated with cardiac, lung, and blood function that are measurable by one or more medical devices, which may be subcutaneously-implantable and, in some cases, leadless. As with a clinician's assessments, certain values of such parameters may be indicative of one or more of heart failure, pulmonary disease, and/or anemia. In addition, the techniques described herein advantageously may differentiate between potential causes of a change in a given parameter, thereby distinguishing between, for example, changes in peripheral perfusion caused by a heart failure condition and changes in peripheral perfusion caused by a pulmonary disorder. That is, such techniques may identify a potentially predominant (or differential) cause of a symptom that may be caused by one or more of multiple medical conditions. Thus, when taken together, this three-part evaluation of the patient's physiological functions may provide a robust indication of a health status of the patient, which may be useful in predicting the patient's likelihood of acute decompensation with respect to one or more particular medical conditions and in proactively modifying the patient's therapy. Because the methods described herein are intended to be performed by one or more devices of a system in between clinician visits, such methods may use electrodes, optical sensors, and/or other sensors to monitor certain parameters of the patient's physiological functions in place of the external signs observed by a clinician.

For example, some of the methods described herein include determining a pulsatile oxygen saturation ($SpO_2$) value and/or a tissue oxygen saturation ($StO_2$) value, which provide surrogates for cardiac output and/or peripheral perfusion, and which in turn may be associated with a heart failure status and/or a pulmonary status of the patient. For example, $SpO_2$ may be indicative of arterial oxygenation and, accordingly, of pulmonary function while $StO_2$ is indicative of both venous and arterial oxygenation and, accordingly, both cardiac and pulmonary function. $StO_2$ may provide a surrogate of cardiac output or otherwise be indicative of cardiac function when $SpO_2$ is relatively normal or unchanged. In some examples, these values may be determined by one or more devices from a more centralized, e.g., subcutaneous and thoracic, location, instead of assessing arterial blood oxygen saturation via observation (e.g., visual observation) and/or pulsatile oxygen saturation ($SpO_2$) at the periphery.

Instead of assessing the patient's anemia status via observation (e.g., visual observation) and/or quantification of the patient's blood hemoglobin concentration via laboratory testing, some of the methods described herein include determining a tissue hemoglobin index (THI) of the patient using the subcutaneously-implantable device. In some examples, methods of using the devices described herein may include monitoring one or more additional parameters associated with cardiac and/or pulmonary function, such as congestion (e.g., based on tissue impedance values (Z)), heart rate, and/or heart rate variability, which may enable such methods to distinguish heart failure conditions from pulmonary disorders and to distinguish different types of heart failure conditions.

A comparison of one or more of the current values of $StO_2$, $SpO_2$, and THI to corresponding baseline values may be used to determine corresponding ones of heart failure, pulmonary, and anemia statuses of the patient. A combination of the heart failure, pulmonary, and anemia statuses may be used to determine a health status, which may indicate whether the one or more of the patient's medical conditions are stable or have progressed. In some techniques described herein, a subcutaneously-implantable device may determine a patient's health status and transmit the health status to a remote computer or other device external to the patient. In some cases, the patient's health status may indicate whether any of the patient's tissue oxygen saturation, blood oxygen saturation, or hemoglobin concentration are insufficient, and may further indicate the patient's likelihood of acute decompensation or hospitalization based on one or more of such statuses, or that a particular symptom is being caused by particular underlying condition of the heart, lungs, or blood of a patient. The remote computer then may transmit instructions for a medical intervention (e.g., instructions for changes to a drug regimen), to a user device used by the patient or a caregiver. In this manner, a patient's diagnoses and/or treatment for conditions such as heart failure, pulmonary disease, and/or anemia may be modified as needed in between clinic visits, which may help avoid adverse medical events such as recurrent symptoms or hospitalization.

In one example, a method for determining a health status of a patient using an implantable medical device configured for subcutaneous implantation outside of a thorax of the patient, the implantable medical device comprising at least one optical sensor comprises, by processing circuitry of a medical device system comprising the implantable medical device: determining a current tissue oxygen saturation value of the patient based on a first signal received from the at least one optical sensor; determining a current pulsatile oxygen saturation value of the patient based on a second signal received from the at least one optical sensor; comparing the current tissue oxygen saturation value and the current pulsatile oxygen saturation value to corresponding ones of a baseline tissue oxygenation saturation value and a baseline pulsatile oxygen saturation value; determining a heart failure status of the patient at least based on the comparison of the current tissue oxygen saturation value to the baseline tissue oxygen saturation value; determining a pulmonary status of the patient at least based on the comparison of the current pulsatile oxygen saturation value of the patient to the baseline pulsatile oxygen saturation value; and determining the health status of the patient based on a combination of the heart failure status and the pulmonary status of the patient.

In another example, a system for determining a health status of a patient using an implantable medical device configured for subcutaneous implantation outside of a thorax of the patient comprises the implantable medical device comprising at least one optical sensor; and processing circuitry configured to: determine a current tissue oxygen saturation value of the patient based on a first signal received from the at least one optical sensor; determine a current pulsatile oxygen saturation value of the patient based on a second signal received from the at least one optical sensor; compare the current tissue oxygen saturation value and the current pulsatile oxygen saturation value to corresponding ones of a baseline tissue oxygenation saturation value and a baseline pulsatile oxygen saturation value; determine a heart failure status of the patient at least based on the comparison of the current tissue oxygen saturation value to the baseline tissue oxygen saturation value; determine a pulmonary status of the patient at least based on the comparison of the current pulsatile oxygen saturation value of the patient to the baseline pulsatile oxygen saturation value; and determine the health status of the patient based on a combination of the heart failure status and the pulmonary status of the patient.

In another example, a system for determining a health status of a patient using an implantable medical device configured for subcutaneous implantation outside of a thorax of the patient comprises the implantable medical device comprising at least one optical sensor; and processing circuitry configured to: determine a current tissue oxygen saturation value of the patient based on a first signal received from the at least one optical sensor; determine a current pulsatile oxygen saturation value of the patient based on a second signal received from the at least one optical sensor; determine a current tissue hemoglobin index value of the patient based on a third signal received from the at least one optical sensor; determine whether a difference between the current tissue oxygen saturation value and the baseline tissue oxygen saturation value satisfies a tissue oxygen saturation threshold value that is associated with a change in a cardiac function of the patient; determine whether a difference between the current pulsatile oxygen saturation value and the baseline pulsatile oxygen saturation value satisfies a pulsatile oxygen saturation threshold value that is associated with a change in a lung function of the patient; and determine whether a difference between the current tissue hemoglobin index value and the baseline tissue hemoglobin index value satisfies a tissue hemoglobin index threshold value that is associated with a change in a red blood cell count of the patient; determine a heart failure status of the patient at least based on the comparison of the current tissue oxygen saturation value to the baseline tissue oxygen saturation value; determine a pulmonary status of the patient at least based on the comparison of the current pulsatile oxygen saturation value of the patient to the baseline pulsatile oxygen saturation value; determine an anemia status of the patient at least based on the comparison of the current tissue hemoglobin index value to the baseline tissue hemoglobin index value; determine the health status of the patient based on a combination of the heart failure status, the pulmonary status, and the anemia status of the patient; and transmit the health status of the patient to a remote computer, wherein the remote computer comprises processing circuitry configured to: receive the health status of the patient transmitted by the processing circuitry of the implantable medical device; and transmit the instructions for the medical intervention to a user device.

In another example, a system for determining a health status of a patient comprises means for determining a current tissue oxygen saturation value of the patient based on a first signal received from at least one optical sensor; means for determining a current pulsatile oxygen saturation value of the patient based on a second signal received from the at least one optical sensor; means for comparing the current tissue oxygen saturation value and the current pulsatile oxygen saturation value to corresponding ones of a baseline tissue oxygenation saturation value and a baseline pulsatile oxygen saturation value; means for determining a heart failure status of the patient at least based on the comparison of the current tissue oxygen saturation value to the baseline tissue oxygen saturation value; means for determining a pulmonary status of the patient at least based on the comparison of the current pulsatile oxygen saturation value of the patient to the baseline pulsatile oxygen saturation value; and means for determining the health status of the patient based on a combination of the heart failure status and the pulmonary status of the patient.

In another example, a non-transitory computer-readable medium stores instructions for causing processing circuitry to perform a method for determining a health status of a patient using an implantable medical device configured for subcutaneous implantation outside of a thorax of the patient, the implantable medical device comprising at least one optical sensor, the method comprising determining a current tissue oxygen saturation value of the patient based on a first signal received from the at least one optical sensor; determining a current pulsatile oxygen saturation value of the patient based on a second signal received from the at least one optical sensor; comparing the current tissue oxygen saturation value and the current pulsatile oxygen saturation value to corresponding ones of a baseline tissue oxygenation saturation value and a baseline pulsatile oxygen saturation value; determining a heart failure status of the patient at least based on the comparison of the current tissue oxygen saturation value to the baseline tissue oxygen saturation value; determining a pulmonary status of the patient at least based on the comparison of the current pulsatile oxygen saturation value of the patient to the baseline pulsatile oxygen saturation value; and determining the health status of the patient based on a combination of the heart failure status and the pulmonary status of the patient.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

FIGS. 4A and 4B are block diagrams illustrating other example leadless implantable medical devices substantially similar to the implantable medical device of FIG. 1;

DETAILED DESCRIPTION

Figure 1:
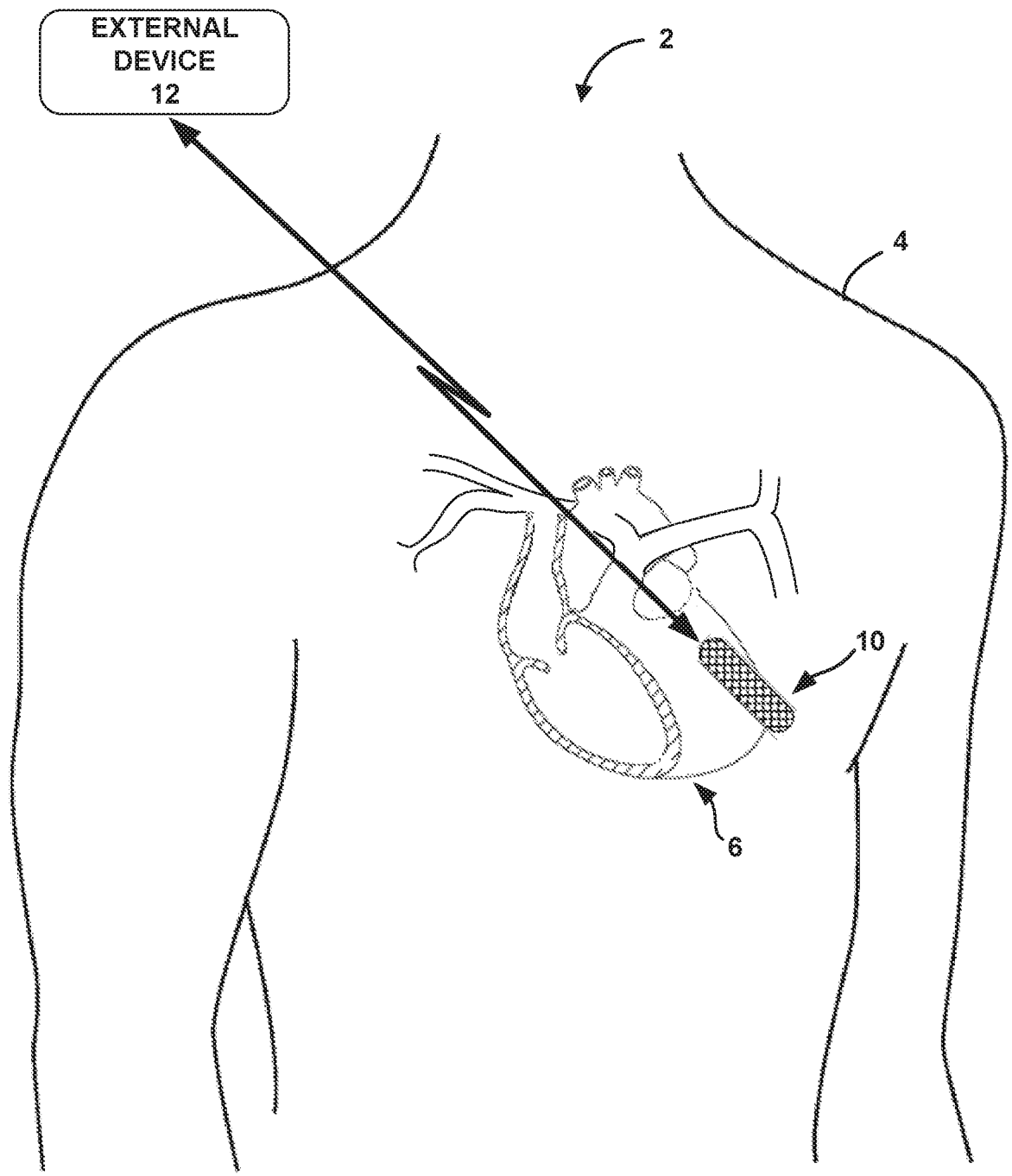
FIG. 1 is a conceptual drawing illustrating an example of a medical device system including a leadless implantable medical device and an external device in conjunction with a patient.

In general, this disclosure describes example techniques related to determining a health status of a patient based on physiological parameters associated with cardiac, lung, and blood functions and, in some cases, determining a differential diagnosis between a cardiac, lung, and anemia, e.g., as the cause of one or more symptoms, based on the parameters. A subcutaneous IMD used in some of the example techniques may be configured for placement under the skin of a patient's torso, such as between the skin and a pectoral muscle. Processing circuitry of the subcutaneous IMD may determine current $StO_2$, $SpO_2$, and THI values of the patient based on signals detected by one or more optical sensors of the subcutaneous IMD. The IMD may, in some examples, be leadless, and the optical sensors may be integrated with and/or connected to a housing of the IMD.

The processing circuitry then may compare the current $StO_2$, $SpO_2$, and THI values to corresponding baseline values, which may be stored in a memory of the IMD. Based on differences between the current values and the baseline values, the processing circuitry may determine a heart failure status, a pulmonary status, and an anemia status of the patient, and determine a current health status of the patient based one or more of the heart failure status, the pulmonary status, or the anemia status of the patient. For example, the processing circuitry may determine that a change in one or more of the patient's cardiac, lung, and blood functions has occurred, and transmit such a determination as part of the patient's health status to a remote computer. In some examples, the differences between the current and baseline values may be given different weights, such as depending upon the outcome of the status determinations. It is further contemplated that, in some examples, the remote computer may transmit instructions for medical intervention to a user device based on the health status. Although techniques for determining a health status of a patient are described herein as being based on a heart failure status, a pulmonary status, and an anemia status, such techniques may be used to determine a health status of a patient based on other statuses that pertain to other physiological functions of the patient. Additionally, although described herein primarily in the context of considering each of cardiac, lung, and blood functions, some examples may include consideration of any one or more functions, e.g., cardiac and lung functions without considering blood function.

Some other techniques may be used to monitor one or more aspects of the cardiac function of a patient, such as a patient with a heart failure condition. Such other techniques may include measuring transthoracic impedance to assess congestion, or measuring pulse transit time (PTT) to assess vasoconstriction. However, such other techniques may not provide a robust assessment of a patient's health status based on the monitoring of multiple physiological functions, as may be obtained by a combined assessment of the patient's cardiac, lung, and blood functions via monitoring of $StO_2$, $SpO_2$, and THI, according to the techniques described herein. Thus, such other techniques may be less useful for patients with one or more interrelated medical conditions whose progression may result in changes in additional physiological functions and/or in the development of additional medical conditions. Moreover, such other techniques may be of limited utility in differentiating between different types of heart failure conditions that are characterized by different hemodynamic profiles and have different treatment requirements. Because the hemodynamic profile of a heart failure patient may change as the patient's heart failure condition progresses, such other techniques may not be able to identify a progression of the patient's heart failure condition. Thus, monitoring of only tissue impedance and/or PTT may be inadequate to assess a patient's health status for the purpose of differentiating between possible causes of a particular symptom that may arise from changes in one or more of a patient's cardiac, lung, and blood functions, and likewise may be inadequate for use in identifying appropriate treatment options.

Other techniques for monitoring one or more of cardiac, lung, and blood functions may be invasive, prone to inaccuracy, and/or cumbersome for long-term monitoring. For example, some methods for monitoring cardiac function may include sensing transthoracic impedance values or producing an electrogram (ECG) with signals obtained from electrodes on leads placed within the thoracic cavity, such as within the heart. Such electrode placement is considerably more invasive than subcutaneous placement, and may be associated with a greater a risk of complications during or after implantation. Some methods for monitoring lung function may include measuring arterial blood oxygenation via arterial blood-gas sampling or $SpO_2$ measurement using an external sensor positioned at the patient's periphery. However, arterial blood-gas sampling is invasive and painful for the patient, whereas external $SpO_2$ sensors may be subject to motion artifacts and too cumbersome for long-term monitoring. Similarly, methods for measuring blood hemoglobin concentration are invasive, and rely upon laboratory analysis of blood samples. Moreover, while some other methods for monitoring physiological functions (e.g., cardiac function) may include generating an alert if a measurement satisfies a threshold, a limitation of such methods is that they do not include providing instructions to the patient for a medical intervention based on such alerts.

In some example techniques described herein, a patient's heart failure, pulmonary, and anemia statuses may be determined using a subcutaneous implantable device configured to measure all three of $StO_2$, $SpO_2$, and THI from a single location near a patient's pectoral muscle. Such measurements may be repeated at predetermined intervals, such as hourly or daily. The device then may determine heart failure, pulmonary, and anemia statuses of the patient based on current and baseline values of $StO_2$, $SpO_2$, and THI, determine a corresponding health status, and transmit the health status via wireless communication to a remote computer, which then may transmit instructions for medical intervention to a user device (e.g., a smartphone or tablet, located with the patient or a caregiver). In some cases, the health status may include a differential diagnosis between a cardiac, lung, and anemia, e.g., as the cause of one or more symptoms experienced by the patient. Thus, in some cases, the techniques described herein advantageously may provide robust and accurate assessment of a patient's health status at regular intervals and enable modification of a patient's treatment between clinician visits, which in turn may provide improved clinical outcomes.

FIG. 1 illustrates the environment of an example medical device system 2 in conjunction with a patient 4 and a heart 6, in accordance with an apparatus and method of certain examples described herein. The example techniques may be used with an implantable medical device (IMD) 10, which may be leadless and in wireless communication with external device 12, as illustrated in FIG. 1. In some examples, IMD 10 may be coupled to one or more leads. In some examples, IMD 10 may be implanted outside of a thoracic cavity of patient 4 (e.g., subcutaneously in the pectoral location illustrated in FIG. 1). IMD 10 may be positioned near the sternum near or just below the level of heart 6. In some examples, IMD 10 may take the form of a Reveal LINQ™ Insertable Cardiac Monitor (ICM), available from Medtronic plc, of Dublin, Ireland. External device 12 may be a computing device configured for use in settings such as a home, clinic, or hospital, and may further be configured to communicate with IMD 10 via wireless telemetry. For example, external device 12 may be coupled to a remote patient monitoring system, such as Carelink®, available from Medtronic plc, of Dublin, Ireland. External device 12 may, in some examples, comprise a programmer, an external monitor, or a consumer device such as a smart phone or tablet.

IMD 10 may include one or more optical sensors, which collectively detect signals that enable a processing circuitry of the IMD 10 to determine current values of subcutaneous $StO_2$, $SpO_2$, and THI for patient 4, and determine heart failure, pulmonary, and anemia statuses of patient 4 based on such values. For example, the one or more optical sensors may be configured to detect signals indicative of an $StO_2$ value, an $SpO_2$ value, and an THI value of the tissue surrounding and the IMD 10. Processing circuitry of IMD 10 may use current $StO_2$, $SpO_2$, and THI values of the tissue surrounding the IMD to determine respective ones of a heart failure status, a pulmonary status, and an anemia status of patient 4.

For example, processing circuitry of IMD 10 may compare the current $StO_2$, $SpO_2$, and THI values to corresponding baseline values stored in a memory of IMD 10 to determine differences between the current $StO_2$, $SpO_2$, and THI values and the corresponding baseline values. If the differences between one or more of the current and corresponding baseline values satisfies a threshold, then processing circuitry of IMD 10 may determine that one or more of a heart failure status, a pulmonary status, or an anemia status of patient 4 has changed relative to a time when the baseline values were established. In some examples, the differences between the current and corresponding baseline values of $StO_2$, $SpO_2$, and THI respectively correspond to changes in the heart failure, pulmonary, and anemia statuses in a 1:1 relationship. In other examples, one or more of the differences between the current and corresponding baseline values of $StO_2$, $SpO_2$, and THI may correspond to multiple ones of the changes in heart failure, pulmonary, and anemia statuses. For example, a difference between the current and corresponding baseline values of $StO_2$ may correspond to changes in both the heart failure and pulmonary statuses.

In some examples, IMD 10 further may include a plurality of electrodes. The plurality of electrodes may be configured to detect signals that enable processing circuitry of IMD 10 to determine current values of additional parameters associated with the cardiac and/or lung functions of patient 4. As noted above, the parameter of $StO_2$ may be associated with both cardiac and lung functions, as $StO_2$ values are based upon both venous oxygen saturation ($SvO_2$), which is a measure of cardiac function, and arterial oxygen saturation ($SaO_2$), which is a measure of lung function. Thus, it may be advantageous for methods that include identifying changes in patient 4's cardiac and lung functions to determine the effects of both of patient 4's cardiac and lung functions on a current $StO_2$ value. In some examples, $SaO_2$ or $SpO_2$ may indicate whether changes in $StO_2$ values are associated with changing cardiac function or changing lung function. Because $SpO_2$ may serve as an approximation of $SaO_2$, measurements of either $SaO_2$ or $SpO_2$ may be used in such examples.

In some examples, the plurality of electrodes of IMD 10 may be configured to detect a signal indicative of a current Z value of the tissue surrounding the IMD 10. For example, processing circuitry of IMD 10 may cause one or more of the plurality of electrodes to produce an electrical current that travels through tissue of patient 4 to another one or more of the plurality of electrodes. Processing circuitry of IMD 10 then may measure a voltage drop across such electrodes and determine the current Z value based on a value of the electrical current and value of the voltage drop. In such examples, it may not be necessary to determine a current $SaO_2$ or $SpO_2$ value, or a current $SvO_2$ value, in order to distinguish the changes in patient 4's cardiac function from changes in patient 4's lung function. In other examples, processing circuitry of IMD 10 may be configured to identify changes in patient 4's lung function by determining whether a difference between a current $SaO_2$ or $SpO_2$ value and a corresponding baseline $SaO_2$ or $SpO_2$ value satisfies a threshold, instead of by cross-referencing the parameter of $StO_2$ with the parameter of Z.

As discussed below with respect to FIG. 11, processing circuitry of IMD 10 may use the current Z value to determine a congestion status of patient 4, which may be considered an aspect of patient 4's heart failure status, by determining whether a difference between the current Z value and a baseline Z value satisfies a threshold. Processing circuitry of IMD 10 then may cross-reference patient 4's congestion status (i.e., congested or not congested) with the outcome of a determination of whether a difference between patient 4's current and baseline $StO_2$ values satisfies an $StO_2$ threshold. Depending on the outcome of the cross reference, processing circuitry of IMD 10 may determine the effects of patient 4's congestion status and pulmonary status on a current $StO_2$ value, thereby distinguishing patient 4's cardiac and lung functions.

In some examples, a method that includes identifying changes in patient 4's cardiac function may include using Z and $StO_2$ values to determine a type of patient 4's heart failure condition. In such examples, processing circuitry of IMD 10 may cross-reference the outcome of the determination of whether the difference between the current Z value and the baseline Z value satisfies a threshold with the outcome of a determination of whether a difference between patient 4's current and baseline $StO_2$ values satisfies an $StO_2$ threshold. As discussed below with respect to FIG. 12, processing circuitry of IMD 10 may characterize, based on the cross reference, congestion and perfusion statuses of a heart failure condition of patient 4. That is, processing circuitry of IMD 10 may determine that a congestion status of the heart failure condition of patient 4 is either "wet" or "dry" (i.e., congested or not congested), and either "warm" or "cold" (i.e., adequately perfused or inadequately perfused).

In some examples, processing circuitry of IMD 10 may be configured to distinguish whether changes in patient 4's blood function are accompanied by changes in patient 4's cardiac function and/or lung function. For example, processing circuitry of IMD 10 may cross-reference an outcome of a determination of whether differences between current values of THI and $StO_2$ and corresponding baseline values of THI and $StO_2$ satisfy a THI and/or an $StO_2$ threshold with a determination of whether differences between one or more of current values of Z and $SpO_2/SaO_2$ and corresponding baseline values of Z and $SpO_2/SaO_2$ satisfy a Z and/or an $SpO_2/SaO_2$ threshold. Processing circuitry of IMD 10 may determine, based on the cross reference, an anemia status and one or both of a congestion status or a pulmonary status of patient 4. For example, processing circuitry of IMD 10 may determine whether an anemia condition of patient 4 is accompanied by a heart failure condition (e.g., a congestive heart failure condition) and/or a pulmonary disorder. In some such examples, a determination that an anemia condition of patient 4 is accompanied by a heart failure condition and/or a pulmonary condition may indicate a higher likelihood of acute decompensation or hospitalization than examples in which processing circuitry of IMD 10 determines that an anemia condition of patient 4 is not accompanied by a heart failure condition and/or a pulmonary condition.

In still other examples, processing circuitry of IMD 10 may be configured to distinguish changes in patient 4's cardiac function from changes in patient 4's lung function by monitoring one or more other parameters associated with patient 4's lung function. For example, IMD 10 may include one or more accelerometers configured to generate a signal that may be associated with of one or more aspects of respiratory cycles of patient 4, such as a frequency and/or amplitude of the respiratory cycles, and/or with one or more respiratory abnormalities of the lung function of patient 4 (e.g., coughing or rales). Additionally, or alternatively, IMD 10 may include and/or one or more acoustic sensors configured to generate a signal that may be associated with one or more aspects of respiratory cycles of patient 4, such as sound or vibrations associated with the respiratory cycles and/or respiratory abnormalities of patient 4, and/or may identify or more aspects of respiratory cycles in a Z (impedance) signal.

In any such other examples, processing circuitry of IMD 10 may receive one or more signals associated with patient 4's lung function from the one or more accelerometers or acoustic sensors and determine a current value of one or more aspects of patient 4's lung function. Processing circuitry of IMD 10 then may determine a respiratory status of patient 4 based on a difference between the current value of the one or more aspects of patient 4's lung function and a corresponding baseline value of the one or more aspects of patient 4's lung function. Processing circuitry of IMD 10 then may cross-reference patient 4's respiratory status (e.g., normal or abnormal) with the outcome of a determination of whether a difference between patient 4's current and baseline $StO_2$ values satisfies an $StO_2$ threshold. Depending on the outcome of the cross reference, processing circuitry of IMD 10 may determine the effects of patient 4's respiratory status on a current $StO_2$ value, thereby distinguishing patient 4's cardiac and lung functions.

Additionally, or alternatively, the plurality of electrodes may be configured to detect an ECG signal, which may be indicative of a heart rate and/or a heart rate variability value of patient 4. As noted above, the parameter of $StO_2$ may be associated with both cardiac and lung functions. In addition, because the parameter of $SpO_2$ may serve as an approximation of $SaO_2$, the parameter of $SpO_2$ also may be associated with both cardiac and lung functions, though predominately with lung functions. Thus, while monitoring both $StO_2$ and $SpO_2$ may be used to distinguish between issues with cardiac or lung function, it may be advantageous for methods described herein to include monitoring one or more additional parameters of cardiac and/or lung function in order to distinguish the effects of each of patient 4's cardiac and lung functions on a current $SpO_2$ value. Such additional parameters may include HR and HRV, each of which may be associated with cardiac function. For example, as further discussed below with respect to FIG. 10, an increase in HR and/or a decrease in HRV may indicate worsening cardiac function. In such examples, it may not be necessary to determine a current $StO_2$ value or a current $SvO_2$ value in order to distinguish the changes in patient 4's cardiac function from changes in patient 4's lung function. In other examples, processing circuitry of IMD 10 may be configured to distinguish changes in patient 4's cardiac function from changes in patient 4's lung function by cross-referencing the parameters of $SpO_2$ and $StO_2$, instead of by cross-referencing the parameter of $SpO_2$ with one or both of the parameters of HR and HRV.

In some examples, the plurality of electrodes of IMD 10 may be configured to detect an ECG signal, which may be indicative of a current heart rate (HR) value and/or a current heart rate variability (HRV) value of patient 4. As discussed below with respect to FIG. 10, processing circuitry of IMD 10 then may compare one or both of the current HR and HRV values to corresponding baseline values, to determine whether a difference between the current HR and/or HRV values satisfy corresponding thresholds. Processing circuitry of IMD 10 then may cross-reference the outcome of this determination with the outcome of a determination of whether a difference between patient 4's current and baseline $SpO_2$ values satisfies an $SpO_2$ threshold. Depending on the outcome of the cross-reference, processing circuitry of IMD 10 may determine the relative effects of patient 4's heart failure status and pulmonary status on current $SpO_2$ value, thereby further distinguishing patient 4's cardiac and lung functions. In some examples, the use of HR and HRV values to distinguish patient 4's cardiac and lung functions may be particularly useful in cases in which patient 4 may have non-congestive heart failure, by accounting for the influence of $SvO_2$ on $StO_2$ (and, by in some cases, on $SpO_2$) regardless of patient 4's congestion status. In any such examples, processing circuitry of IMD 10 may determine a current arrhythmia status of patient 4 based on the ECG signal (e.g., the presence or absence of atrial fibrillation and a ventricular rate during atrial fibrillation), which indicate cardiac function and also may help enable processing circuitry of IMD 10 to distinguish whether changes in monitored parameters are attributable to patient 4's cardiac and lung functions.

Regardless of whether any of the differences between the current and corresponding baseline values of $StO_2$, $SpO_2$, THI, Z, HR, and HRV exceed a threshold, IMD 10 then may determine a health status of the patient based on a combination of the heart failure, pulmonary, and anemia statuses, and wirelessly transmit the heart failure status of patient 4 to external device 12. The health status may include a diagnostic score of patient 4, which may be associated with a likelihood that patient 4 will decompensate and require hospitalization within a certain period of time. In some examples, the health status may include a differential diagnosis between a heart failure condition, a pulmonary disorder, and anemia that patient 4 may have (e.g., as the cause or causes of one or more symptoms experienced by the patient). IMD 10 may transmit a health status of patient 4 to external device 12 at predetermined intervals, such as daily, weekly, or at any other desired period. Additionally, or alternatively, IMD 10 may determine a health status of patient 4 on an on-demand basis upon receiving input originating from patient 4 or a caregiver, such as input that indicates patient 4 is experiencing one or more particular symptoms.

Although in some examples, a health status of patient 4 may be based on differences between current and corresponding baseline values of each of $StO_2$, $SpO_2$, THI, Z, HR, HRV, or other parameters, examples herein may be described with respect to $StO_2$, $SpO_2$, and THI for the sake of clarity. However, in any such examples, methods of determining a health status of patient 4 may include values of Z, HR, HRV, or other parameters, in any combination that may be appropriate for patient 4.

In some examples, an interval at which IMD 10 determines a health status of patient 4 is the same as an interval at which IMD 10 transmits the health status to external device 12. In other examples, IMD 10 may determine a health status of patient 4 more frequently than IMD 10 transmits a health status to external device 12. By determining a health status more often than a health status is transmitted, an accuracy of a technique for determining a health status may be enhanced by eliminating outlier measurements of $StO_2$, $SpO_2$, and THI. For example, IMD 10 may determine that a difference between a current $StO_2$, $SpO_2$, and THI of patient 4 and a corresponding baseline satisfies a threshold only if a certain number or proportion of preceding results met or exceeded the threshold. In other examples, a single incident in which a current value met or exceeded a threshold may suffice to cause IMD 10 to determine that a change in one or more of a corresponding heart failure, pulmonary, or anemia status has occurred, and thus that a change in the health status of patient 4 has occurred. In some examples, a clinician may configure a sensitivity of IMD 10 to certain types of values that exceed a threshold at or after the time of implant of IMD 10, depending on factors such as the individual condition of patient 4. As discussed below, several aspects of the operation of IMD 10 may be configured by a clinician to help achieve improved monitoring and clinical outcomes for individual patients such as patient 4.

At or after the time of implantation of IMD 10 into the subcutaneous location illustrated in FIG. 1, a clinician may configure one or more aspects of IMD 10. In some examples, a clinician may establish baseline values of $StO_2$, $SpO_2$, and THI using conventional assessments. For example, the clinician may conduct arterial and venous blood draws with co-oximeter measurements to assess tissue perfusion, apply a pulse oximetry device to the patient's periphery to approximate arterial blood oxygenation, and review laboratory results of a blood analysis to approximate tissue hemoglobin index. In addition, the clinician may complete a standard examination and assessment of patient 4 to evaluate one or more additional aspects of cardiac, lung, and/or blood function. For example, the clinician may identify whether, and to what extent, congestion is present by observing the patient for edema. The clinician then may use an app on a tablet or other smart device to enter empirically-determined baseline values of patient 4's $StO_2$, $SpO_2$, and THI into a memory of the IMD 10, along with corresponding baseline heart failure, pulmonary, and anemia statuses.

In other examples, instead of determining baseline values for $StO_2$, $SpO_2$, and THI using the conventional assessments noted above, a clinician may conduct the standard examination and assessment of patient 4 to determine patient 4's heart failure, pulmonary, and anemia statuses. Based on the outcome of this assessment, and optionally on other data corresponding to patient 4, the clinician may select baseline values of $StO_2$, $SpO_2$, and THI for patient 4. Lists or tables of such values may be presented by the app on the clinician tablet or other smart device, or may be available from a centralized database. Once the clinician has selected appropriate baseline values for patient 4, he or she may use the app to store the values in IMD 10.

In still other examples, IMD 10 may be configured to undertake a learning phase after implantation into patient 4, in which IMD 10 determines the baseline values of $StO_2$, $SpO_2$, and THI for patient 4 based on values collected by IMD 10 over a period of time, and stores the values in a memory of IMD 10. For example, IMD 10 may measure $StO_2$, $SpO_2$, and THI on a relatively frequent basis (e.g., hourly or several times a day) for a period of time (e.g., a week or more) to determine baseline values during a period when the condition of patient 4 is stable and not decompensating.

Because heart failure conditions, pulmonary disorders, and anemia are progressive diseases whose progressions may be interrelated, values for baselines, thresholds, and event identifiers associated with patient 4 also may be updated periodically. For example, IMD 10 may undertake a new learning phase monthly, quarterly, yearly, or at an expiration of any other appropriate period. The new learning phase may produce new values associated with one or more of the baselines, thresholds, and evidence levels based on an updated heart failure status of patient 4. In other examples, a clinician may program IMD 10 to update such values as needed, such as following a health event experienced by patient 4 that may affect the applicability of such values to one or more aspects of patient 4's health status.

In some examples, IMD 10 may determine baseline values based on averages of the $StO_2$, $SpO_2$, and THI values collected during the training period. In other examples, IMD 10 may reject outlier values collected during the training period prior to determining the baseline values, although IMD may use other methods of determining baseline values from collected values. In some examples in which IMD 10 uses a training period to determine the baseline values, a clinician also may conduct the standard examination and assessment of heart failure, pulmonary, and anemia statuses of patient 4, and store the values in IMD 10.

In addition to determining baseline values of $StO_2$, $SpO_2$, and THI for patient 4, IMD 10 or a clinician also may determine threshold values of $StO_2$, $SpO_2$, and THI for patient 4 and store the threshold values in a memory of IMD 10. In some examples, a threshold value may be indicative of a value of a difference between a current value of one of $StO_2$, $SpO_2$, and THI and a corresponding baseline value that indicates that one or more of a heart failure, pulmonary, or anemia status of patient 4 may have changed. For example, a determination by IMD 10 of a heart failure status of patient 4 may be based, at least in part, on whether a difference between the current $StO_2$ value and the corresponding baseline value satisfies a threshold value.

IMD 10 may determine threshold values for each of a number of different baseline values for each of $StO_2$, $SpO_2$, and THI, such as during the training period of IMD 10. In some examples, IMD 10 may automatically associate a particular threshold value with a particular baseline value of one of $StO_2$, $SpO_2$, and THI for patient 4. In other examples, IMD 10 may determine a threshold value for the one of $StO_2$, $SpO_2$, and THI based in part on the values of the other baselines determined for patient 4. For example, if a baseline $StO_2$ value of patient 4 indicates that patient 4 has inadequate tissue perfusion, IMD 10 may select a lower threshold value for $SpO_2$ than if the baseline $StO_2$ value does not indicate that patient 4 has inadequate tissue perfusion. In this manner, such threshold determination may account for physiological parameters (e.g., $StO_2$) that may be associated with more than one physiological function (e.g., cardiac and lung functions). In this way, IMD 10's determinations of health status may be more sensitive for patients at a high overall risk for acute decompensation, such as those who have multiple medical conditions or those for whom acute decompensation may have greater health consequences. In other examples, a clinician may choose to program IMD 10 to apply relatively higher or lower thresholds than those selected by processing circuitry of IMD 10 based on other considerations known to the clinician.

Regardless of whether the threshold values for $StO_2$, $SpO_2$, and THI are determined by processing circuitry of IMD 10 during a training period or by a clinician, such threshold values may be updated at one or more times after implantation of IMD 10. For example, threshold values may be updated after patient 4 experiences an acute decompensation or hospitalization event, which may indicate that one or more parameters of a heart failure condition, a pulmonary disorder, or anemia of patient 4 has progressed or otherwise changed. Or, the threshold values may be updated at the expiration of a time period (e.g., weekly, monthly, or yearly following implantation of IMD 10). Such updates to the threshold values may be performed automatically by processing circuitry of IMD 10, or manually by a clinician. In any such examples, the updated threshold values may be determined based on trends in one or more of the current values of $StO_2$, $SpO_2$, and THI during the preceding time period. In this manner, the threshold values used in the techniques described herein may be modified as needed to account for changes in the health status of patient 4.

In addition to determining whether the differences between any current values of $StO_2$, $SpO_2$, and THI and corresponding baseline values exceed one or more threshold values, IMD 10 also may determine a diagnostic score for patient 4 based on the current values of $StO_2$, $SpO_2$, and THI. A diagnostic score may be a value (e.g., a numeric value) that is associated with a likelihood that patient 4 will decompensate and/or require hospitalization within a certain period of time, regardless of whether the differences between any current values of $StO_2$, $SpO_2$, and THI and corresponding baseline values exceed one or more threshold values. In some examples, a diagnostic score of patient 4 may be further increased if one or more such differences exceed a threshold value.

IMD 10 may determine a diagnostic score of patient 4 based, at least in part, on values of evidence levels that may be associated with values of various parameters of one or more medical conditions such as heart failure conditions, pulmonary disorders, and anemia. In some examples, evidence levels may be determined based on assessments of one or more populations of patients with one or more such conditions. Diagnostic scores may comprise one or more values associated with one or more evidence levels, with each evidence level being associated with a value of a parameter of a particular medical condition. For example, assessments of patient populations may classify parameters of heart failure (e.g., congestion and inadequate perfusion) as occurring at varying levels of severity. Each level of severity of each parameter may be characterized as an "evidence level" associated with a numerical value, and patient outcomes (e.g., prior patient population data) for each evidence level may be documented. In light of patient outcomes, the numerical values associated with the evidence levels may be weighted to reflect their predictive value of patient outcome.

IMD 10 may determine a diagnostic score associated with one or more of a heart failure status, a pulmonary status, or an anemia status of patient 4 based on a combination of the evidence levels associated with the current values of $StO_2$, $SpO_2$, and THI of patient 4. For example, the diagnostic score may be based on an integration of prior population data (e.g., data associated with the evidence levels) with measurements specific to patient 4 (e.g., the current values of $StO_2$, $SpO_2$, or THI of patient 4), such as by using Bayesian statistics or other methods of machine learning. In some examples, a diagnostic score based on a combination of evidence levels may indicate a likelihood that patient 4 underwent a change in each of the corresponding parameters of the medical conditions associated with the evidence levels. For example, an evidence level associated with a current value of $StO_2$ may indicate an X % chance that patient 4 underwent a change in heart failure status, which may be associated with a change in cardiac function, during a preceding time period on which the diagnostic score is based. Similarly, an evidence level associated with a current value of $SpO_2$ or THI may indicate a Y % or Z % chance that patient 4 underwent a change in respective ones of a pulmonary or anemia status, which respectively may be associated with changes in lung or blood function, during the preceding time period. In some examples, the diagnostic score may be adjusted upward or downward based on how many of the differences between the current values of patient 4 and the corresponding baseline values exceed associated thresholds. In addition, a clinician may manually modify weights assigned by IMD 10 to evidence levels for different measured parameters, depending on an individual condition or medical history of patient 4. For example, the clinician may manually modify one or more of the weights assigned by IMD 10 based on events in the medical history of patient 4 such as hospital admissions for heart failure, medication changes, history of systolic or diastolic heart failure, hypertension, respiratory illness (e.g., COPD), diabetes, atrial fibrillation, renal failure, one or more blood disorders (e.g., anemia), one or more sleep disorders (e.g., sleep apnea), among others. In any such examples, the evidence levels associated with the parameters of $StO_2$, $SpO_2$, and THI may be stored in a memory of IMD 10.

In some examples, a diagnostic score, as described above, may be a baseline diagnostic score associated with one or more of a heart failure status, a pulmonary status, or an anemia status of patient 4. Because heart failure conditions, pulmonary disorders, and anemia may be progressive diseases, IMD 10 periodically may determine an updated health status of patient 4 at regular intervals. In some examples, IMD 10 may determine an updated health status of patient 4 by iteratively performing the methods described above. In other examples, an updated health status of patient 4 determined by IMD 10 may be based, at least in part, on a determination of a current diagnostic score of patient 4 and a comparison of the current diagnostic score to a previously-determined diagnostic score of patient 4 (e.g., a baseline diagnostic score). In some examples, an updated health status may include an updated diagnosis of one or more of a heart failure condition, a pulmonary disorder, and anemia, such as a diagnosis that a heart failure condition of patient 4 has progressed from a first type of heart failure condition to a second type of heart failure condition.

In such examples, IMD 10 may determine a current diagnostic score of patient 4 by combining weighted values associated with the current values of $StO_2$, $SpO_2$, and THI of patient 4. For example, IMD 10 may determine a difference between current values of each of $StO_2$, $SpO_2$, and THI and the corresponding baseline values of patient 4. IMD 10 then may determine a weighted value for each of the differences between the current values and the corresponding baseline values. In some examples, IMD 10 may assign weights to the difference values based on factors such as a medical history of patient 4, which may include one or more of the medical history events described above with respect to examples in which a clinician manually modifies one or more of the weights. For example, patient 4 may have a medical history of anemia, which may indicate that patient 4 is prone to future episodes of anemia. Or, population-based data may indicate that patients having a same or similar profile of baseline values as patient 4 may be particularly likely to become anemic. In some examples, weights assigned by IMD 10 to the difference values may have negative values, such as if a medical history of patient 4 or population-based data indicate that patient 4 is unlikely to become anemic. IMD 10 then may combine the weighted values of the differences between the current values and the baseline values, to arrive at a current diagnostic score for patient 4.

In some examples, IMD 10 may compare the current diagnostic score to the baseline diagnostic score of patient 4, the latter of which may have been determined during a prior iteration of a method in which IMD 10 determined a health status of patient 4. IMD 10 then may determine an updated health status of patient 4 based on the comparison of the baseline diagnostic score to the current diagnostic score, and transmit the updated health status to a remote computer (e.g., external device 12). External device 12, or another remote computer, then may transmit instructions for a medical intervention (e.g., a change in a drug regimen, or instructions to schedule a clinician visit or seek medical attention), to an interface of a user device located with patient 4.

In some examples, the baseline diagnostic score of patient 4 may be updated, in a substantially similar manner as described above with respect to the threshold values. For example, the baseline diagnostic score of patient 4 may be updated after patient 4 experiences an acute decompensation or hospitalization event, which may indicate that one or more parameters of a medical condition of patient 4 has progressed or otherwise changed. Or, the baseline diagnostic score of patient 4 may be updated at the expiration of a time period (e.g., weekly, monthly, or yearly following implantation of IMD 10). Such updates to the baseline diagnostic score of patient 4 may be performed automatically by processing circuitry of IMD 10, or manually by a clinician.

In some examples, medical device system 2 may further include an implantable pressure sensing device that includes one or more pressure sensors and may be used to monitor a cardiovascular pressure, e.g., a pulmonary artery (PA) pressure, of patient 4. Increased interstitial fluid volume may subsequently be correlated with increased PA or other blood pressure and congestion of the lungs. Congested lungs may interfere with oxygen exchange and result in decreasing arterial oxygen saturation during the progression of an acute heart failure decompensation. Thus, techniques of determining a health status of patient 4 may include monitoring PA pressure or another blood pressure in order to provide an additional parameter by which medical device system 2 may monitor the cardiac and lung functions of patient 4. In such examples, an implantable pressure sensing device may be implanted within a pulmonary artery or other portion of the vasculature of patient 4. The pressure sensing device may include processing circuitry configured to receive signals from the one or more pressure sensors and determine a current PA pressure value or other current blood pressure value of patient 4, and communication circuitry configured to transmit the current PA pressure value or other current blood pressure value of patient 4 to IMD 10 and/or external device 12. As with other parameters of physiological functions of patient 4, processing circuitry of IMD 10 may compare a current blood pressure value to a baseline blood pressure value, such as by comparing the current PA pressure value to a baseline PA pressure value. Processing circuitry of IMD 10 then may determine whether a difference between the current PA pressure value or other pressure value and the corresponding baseline value exceeds a threshold and include such a determination in a determination of whether the cardiac and/or lung functions of patient 4 have changed, and/or in a determination of a diagnostic score of patient 4.

As described above, the operating parameters of IMD 10 readily may be customized to meet the needs of patient 4, such as by setting values of baselines, thresholds, and evidence levels based on the individual attributes of patient 4. The extent and ease of customizability of IMD 10 may provide numerous benefits. For example, customizability of IMD 10 to reflect a heart failure condition of patient 4 helps ensure that appropriate drug therapies are prescribed for patient 4, thereby reducing a likelihood of human error in prescribing treatment. In addition, in examples in which IMD 10 selects one or more of the baseline values, threshold values, or evidence level values for patient 4, burdens on the clinician's time may be reduced, which may reduce the time needed for an office visit and promote efficient treatment. Moreover, as discussed above, IMD 10 enables modification of heart failure, pulmonary, and/or anemia treatments for patient 4 in between clinician visits, which may help avoid acute decompensation and thus lead to better clinical outcomes, such as improved quality of life for patient 4 or reduced medical expenses.

External device 12 may be used to program commands or operating parameters into IMD 10 for controlling its functioning (e.g., when configured as a programmer for IMD 10). In some examples, external device 12 may be used to interrogate IMD 10 to retrieve data, including device operational data as well as physiological data accumulated in IMD memory. Such interrogation may occur automatically according to a schedule, or may occur in response to a remote or local user command. Programmers, external monitors, and consumer devices are examples of external devices 12 that may be used to interrogate IMD 10. Examples of communication techniques used by IMD 10 and external device 12 include radiofrequency (RF) telemetry, which may be an RF link established via Bluetooth, WiFi, or medical implant communication service (MICS). In some examples, external device 12 may include a user interface configured to allow a clinician to remotely interact with IMD 10.

Medical device system 2 is an example of a medical device system configured to monitor a health status of patient 4, diagnose causes of symptoms experienced by patient 4 by differentiating heart failure conditions, pulmonary disorders, and anemia from one another, and facilitate updates to patient 4's treatment, e.g., for a heart failure condition, a pulmonary disorder, and/or anemia, as needed between clinician visits. The techniques described herein may be performed by processing circuitry of a device of medical device system 2, such as processing circuitry of IMD 10. Additionally, or alternatively, the techniques described herein may be performed, in whole or in part, by processing circuitry of external device 12, and/or by processing circuitry of one or more other implanted or external devices or servers not shown. Examples of the one or more other implanted or external devices may include a transvenous, subcutaneous, or extravascular pacemaker or implantable cardioverter-defibrillator (ICD), a blood analyzer, an external monitor, or a drug pump. The communication circuitry of each of the devices of medical device system 2 allows the devices to communicate with one another. In addition, although the optical sensors and electrodes are described herein as being positioned on a housing of IMD 10, in other examples, such optical sensors and/or electrodes may be positioned on a housing of another device implanted in or external to patient 4, such as a transvenous, subcutaneous, or extravascular pacemaker or ICD, or coupled to such a device by one or more leads. For example, in cases in which patient 4 has an implanted pacemaker or ICD, the techniques described herein may include sensing signals for determining $StO_2$ or other parameters with electrodes on the pacemaker or ICD. In such examples, electrodes or one or more optical sensors for detecting signals associated with $SpO_2$ and THI may be positioned on one or more external monitoring devices (e.g., a wearable monitor). In such examples, one or more of the pacemaker/ICD and the one or more external monitoring devices may include processing circuitry configured to receive signals from the electrodes or optical sensors on the respective devices and/or communication circuitry configured to transmit the signals from the electrodes or optical sensors to another device (e.g., external device 12) or server.

Figure 2:
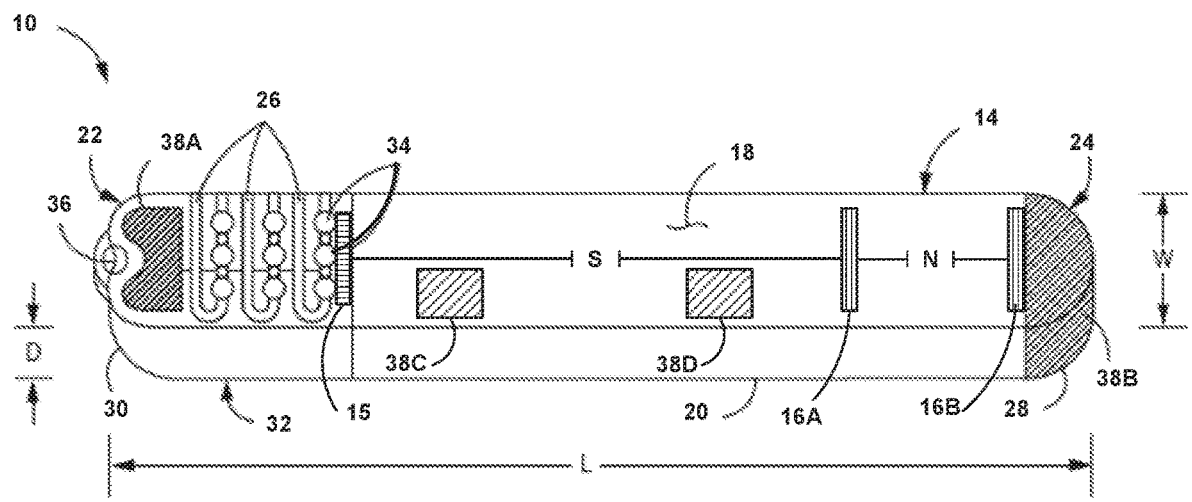
FIG. 2 is a conceptual drawing illustrating an example configuration of the leadless implantable medical device of the medical device system of FIG. 1.
Figure 3:
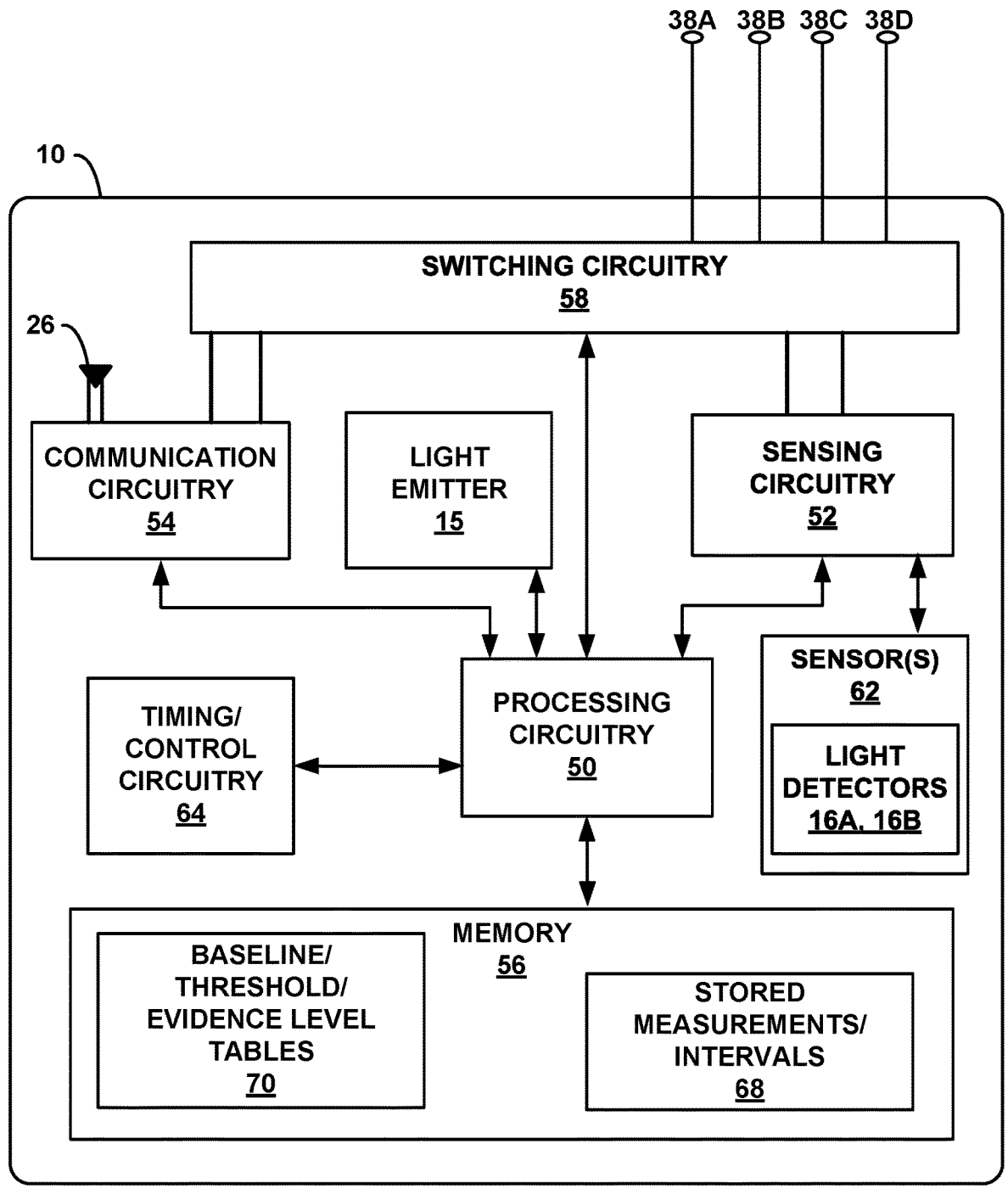
FIG. 3 is a functional block diagram illustrating another perspective of the example configuration of the leadless implantable medical device of FIG. 1.
Figure 4A:
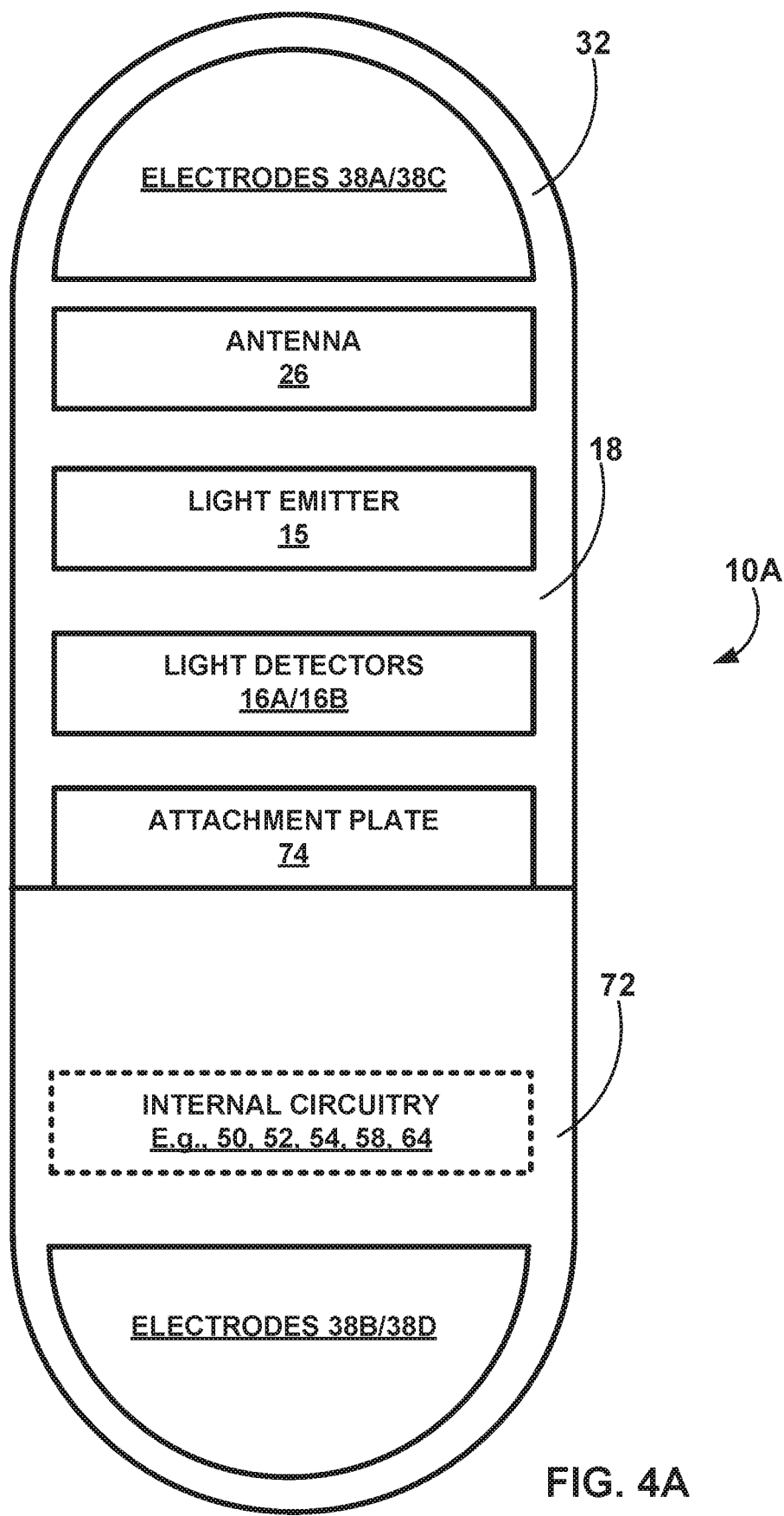

FIGS. 2-4B illustrate various aspects and example arrangements of IMD 10 of FIG. 1. For example, FIG. 2 conceptually illustrates an example physical configuration of IMD 10. FIG. 3 is a block diagram illustrating an example functional configuration of IMD 10. FIGS. 4A and 4B illustrate additional views of an example physical and functional configuration of IMD 10. It should be understood that any of the examples of IMD 10 described below with respect to FIGS. 2-4B may be used to implement the techniques described herein for determining a health status and differentiating heart failure conditions, pulmonary disorders, and anemia as causes of symptoms experienced by patient 4.

FIG. 2 is a conceptual drawing illustrating an example configuration of IMD 10 of FIG. 1. In the example shown in FIG. 2, IMD 10 may comprise a leadless, subcutaneously-implantable monitoring device having a housing 14, a light emitter 15, a proximal light detector 16A, and a distal light detector 16B. Housing 14 may further comprise first major surface 18, second major surface 20, proximal end 22, and distal end 24. In some examples, IMD 10 may include one or more additional light emitters and/or light detectors (not shown), which may be positioned on one or both of major surfaces 18, 20 of IMD 10. Housing 14 encloses electronic circuitry located inside the IMD 10, and protects the circuitry contained therein from fluids such as body fluids.

In the example shown in FIG. 2, IMD 10 is defined by a length L, a width W, and thickness or depth D. In this example, IMD 10 is in the form of an elongated rectangular prism in which length L is significantly greater than width W, and in which width W is greater than depth D. However, other configurations of IMD 10 are contemplated, such as those in which the relative proportions of length L, width W, and depth D vary from those described and shown in FIG. 2. In some examples, the geometry of the IMD 10, such as the width W being greater than the depth D, may be selected to allow IMD 10 to be inserted under the skin of the patient using a minimally invasive procedure and to remain in the desired orientation during insertion. In addition, IMD 10 may include radial asymmetries (e.g., the rectangular shape)

along a longitudinal axis of IMD 10, which may help maintain the device in a desired orientation following implantation.

Overall, IMD 10 may have a length L of about 20-30 mm, about 40-60 mm, or about 45-60 mm. In some examples, the width W of major surface 18 may range from about 3-10 mm, and may be any single width or range of widths between about 3-10 mm. In some examples, a depth D of IMD 10 may range from about 2-9 mm. In other examples, the depth D of IMD 10 may range from about 2-5 mm, and may be any single or range of depths from about 2-9 mm. In any such examples, IMD 10 is sufficiently compact to be implanted within the subcutaneous space of patient 4 in the region of a pectoral muscle.

IMD 10, according to an example of the present disclosure, may have a geometry and size designed for ease of implant and patient comfort. Examples of IMD 10 described in this disclosure may have a volume of 3 cubic centimeters ($cm^3$) or less, 1.5 $cm^3$ or less, or any volume therebetween. In addition, in the example shown in FIG. 2, proximal end 22 and distal end 24 are rounded to reduce discomfort and irritation to surrounding tissue once implanted under the skin of patient 4. In some examples, a configuration of IMD 10, including instrument and method for inserting IMD 10 is described, for example, in U.S. Patent Publication No. 2014/0276928, incorporated herein by reference in its entirety. In some examples, a configuration of IMD 10 is described, for example, in U.S. Patent Publication No. 2016/0310031, incorporated herein by reference in its entirety.

In the example shown in FIG. 2, first major surface 18 of IMD 10 faces outward towards the skin, when IMD 10 is inserted within patient 4, whereas second major surface 20 is faces inward toward musculature of patient 4. Thus, first and second major surfaces 18, 20 may face in directions along a sagittal axis of patient 4 (see FIG. 1), and this orientation may be maintained upon implantation due to the dimensions of IMD 10.

In the example shown in FIG. 2, proximal end 22 of IMD 10 includes header assembly 32 having one or more of integrated antenna 26, anti-migration projections 34, and suture hole 36. Integrated antenna 26 is located on the same major surface (e.g., first major surface 18) as light emitter 15, and may be an integral part of header assembly 32. In other examples, integrated antenna 26 may be formed on the major surface opposite from light emitter 15, or, in still other examples, may be incorporated within housing 14 of IMD 10. Antenna 26 may be configured to transmit or receive electromagnetic signals for communication. For example, antenna 26 may be configured to transmit to or receive signals from a programmer via inductive coupling, electromagnetic coupling, tissue conductance, Near Field Communication (NFC), Radio Frequency Identification (RFID), Bluetooth, WiFi, or other proprietary or non-proprietary wireless telemetry communication schemes. Antenna 26 may be coupled to communication circuitry of IMD 10, which may drive antenna 26 to transmit signals to external device 12, and may transmit signals received from external device 12 to processing circuitry of IMD 10 via communication circuitry.

IMD 10 may include several features for retaining IMD 10 in position once subcutaneously implanted in patient 4. For example, as shown in FIG. 2, housing 14 may include anti-migration projections 34 positioned adjacent integrated antenna 26. Anti-migration projections 34 may comprise a plurality of bumps or protrusions extending away from first major surface 18, and may help prevent longitudinal movement of IMD 10 after implantation in patient 4. In other examples, anti-migration projections 34 may be located on the opposite major surface as proximal electrode 38A and/or integrated antenna 26. In addition, in the example shown in FIG. 2 header assembly 32 includes suture hole 36, which provides another means of securing IMD 10 to the patient to prevent movement following insertion. In the example shown, suture hole 36 is located adjacent to proximal electrode 38A. In some examples, header assembly 32 may comprise a molded header assembly made from a polymeric or plastic material, which may be integrated or separable from the main portion of IMD 10.

In the example shown in FIG. 2, proximal light detector 16A may be positioned at a distance S from light emitter 15, and a distal light detector 16B positioned at a distance S+N from light emitter 15. In other examples, IMD 10 may include only one of light detectors 16A, 16B, or may include additional light emitters and/or additional light detectors. Collectively, light emitter 15 and light detectors 16A, 16B may comprise an optical sensor, which may be used in the techniques described herein to determine $StO_2$, $SpO_2$, and THI values of patient 4. Although light emitter 15 and light detectors 16A, 16B are described herein as being positioned on housing 14 of IMD 10, in other examples, one or more of light emitter 15 and light detectors 16A, 16B may be positioned, on a housing of another type of IMD within patient 4, such as a transvenous, subcutaneous, or extravascular pacemaker or ICD, or connected to such a device via a lead. Light emitter 15 includes a light source, such as an LED, that may emit light at one or more wavelengths within the visible and/or near-infrared (NIR) spectra. For example, light emitter 15 may emit light at one or more of about 680 nanometers (nm), 720 nm, 760 nm, 800 nm, or at any other suitable wavelengths. As discussed in further detail below, the one or more wavelengths of light emitted by light emitter 15 may be used by processing circuitry of IMD 10 to determine $StO_2$, $SpO_2$, and THI.

As shown in FIG. 2, light emitter 15 may be positioned on header assembly 32, although, in other examples, one or both of light detectors 16A, 16B may additionally or alternatively be positioned on header assembly 32. In some examples, light emitter 15 may be positioned on a medial section of IMD 10, such as part way between proximal end 22 and distal end 24. Although light emitter 15 and light detectors 16A, 16B are illustrated as being positioned on first major surface 18, light emitter 15 and light detectors 16A, 16B alternatively may be positioned on second major surface 20. In some examples, IMD may be implanted such that light emitter 15 and light detectors 16A, 16B face inward when IMD 10 is implanted, toward the muscle of patient 4, which may help minimize interference from background light coming from outside the body of patient 4. Light detectors 16A, 16B may include a glass or sapphire window, such as described below with respect to FIG. 4B, or may be positioned beneath a portion of housing 14 of IMD 10 that is made of glass or sapphire, or otherwise transparent or translucent.

Light emitter 15 may emit light into a target site of patient 4 during a technique for determining an $StO_2$ value of patient 4. The target site generally may include the blood within blood vessels in the interstitial space around IMD 10 when IMD 10 is implanted in patient 4. Light emitter 15 may emit light directionally in that light emitter may direct the signal to a side of IMD 10, such as when light emitter 15 is disposed on the side of IMD 10 that includes first major surface 18. The target site may include the subcutaneous tissue adjacent IMD 10 within patient 4. In one example, light emitter 15 may deliver 180-degree light signals, such as 180 degrees along a dimension parallel to a longitudinal axis of IMD 10. In some examples, a light signal may be a cloud of light generally directed inward, toward the musculature and away from the skin of patient 4. In some examples, the light signal may take the mean free path, as the light signal may be non-directional once emitted from light emitter 15.

Techniques for determining an $StO_2$ value may be based on the optical properties of blood-perfused tissue that change depending upon the relative amounts of oxygenated and deoxygenated hemoglobin in the microcirculation of tissue. These optical properties are due, at least in part, to the different optical absorption spectra of oxygenated and deoxygenated hemoglobin. Thus, the oxygen saturation level of the patient's tissue may affect the amount of light that is absorbed by blood within the tissue adjacent IMD 10 as well as the amount of light that is reflected by the tissue. In some cases, techniques for determining $StO_2$ may include distinguishing between the $SvO_2$ and the $SaO_2$ components of $StO_2$. For example, light emitter 15 may be configured to emit light at wavelengths that enable processing circuitry of IMD 10 to determine current $SvO_2$ and/or $SaO_2$ values from a current $StO_2$ value. Such determinations may provide information about the balance or imbalance of oxygen supply and demand in the tissue of patient 4, thus reflecting venous oxygen reserve (i.e., oxygen remaining after extraction by tissues and vital organs). Because $SvO_2$ is a measure of cardiac function, processing circuitry of IMD 10 may use this information in determining the relative effects of cardiac function on the current $StO_2$ value, which may enhance confidence in the heart failure status determined by IMD 10.

In some example techniques for determining $StO_2$, light emitter 15 may emit visible (VIS) and/or NIR light at multiple wavelengths, either simultaneously or sequentially. Such wavelengths may include approximately 680 nm, 720 nm, 760 nm, and 800 nm, or any other appropriate wavelengths. In some example techniques, light emitter 15 may emit light at one or more wavelengths capable of shallow penetration into tissue (i.e., tissue relatively close to IMD 10), as well at one or more wavelengths capable of deeper penetration into tissue (i.e., tissue further away from IMD 10). In such examples, using wavelengths capable of penetrating tissue to different depths may enable the elimination of measurement errors, which may be caused by factors such as fibrous tissue encapsulation that may form around IMD 10 post-implant. [ . . . ] For example, using wavelengths capable of penetrating tissue to different depths may enable isolation of the deeper tissue. In such examples, processing circuitry of IMD 10 may subtract a signal received from light detectors 16A, 16B that is associated with a shallow-penetrating wavelength from a signal associated with a deep-penetrating wavelength to yield a net measurement of the deeper tissue. In some examples, using wavelengths capable of penetrating tissue to different depths also may enable the identification and subtraction of effects of common-mode errors that impact signals corresponding to both the shallow-penetrating wavelength and the deep-penetrating wavelength. For example, by taking two measurements over two differing tissue volumes and determining a difference between the two corresponding signals, processing circuitry of IMD 10 identify and reduce the effects of common-mode errors associated with the difference between the two signals, such as tissue formation, adhesion, or changes in tissue content.

Light emitter 15 may include a single photodiode that is capable of emitting light at a range of wavelengths appropriate for use in determining $StO_2$. In other examples, light emitter 15 may include multiple photodiodes capable of emitting light at multiple ranges of wavelengths. Light detectors 16A, 16B each may receive light from light emitter 15 that is reflected by the tissue, and generate electrical signals indicating the intensities of the light detected by light detectors 16A, 16B. Processing circuitry of IMD 10 then may evaluate the electrical signals from light detectors 16A, 16B in order to determine an $StO_2$ value of patient 4. In examples in which light emitter 15 simultaneously emits multiple wavelengths of light, processing circuitry of IMD 10 may evaluate the signals from light detectors 16A, 16B by filtering the signals in to different wavelengths corresponding to those emitted by light emitter 15. For example, processing circuitry of IMD 10 may execute a continuous wave near-infrared algorithm for estimating local hemoglobin oxygen saturation in tissue ($StO_2$) by using single depth attenuation measurements at 680, 720, 760, and 800 nm and converting light received by light detectors 16A, 16B into two second-derivative attenuation measurements centered at 720 nm ($2D_{720}$) and 760 nm ($2D_{760}$), which may reduce effects of light scattering, chromophores with constant absorption, baseline/instrumentation drift, and movement artifacts on the determined $StO_2$ value.

In some examples, a difference between the electrical signals generated by light detectors 16A, 16B may enhance an accuracy of the $StO_2$ value determined by IMD 10. For example, because tissue absorbs some of the light emitted by light emitter 15, the intensity of the light reflected by tissue becomes attenuated as the distance (and amount of tissue) between light emitter 15 and light detectors 16A, 16B increases. Thus, because light detector 16B is positioned further from light emitter 15 (at distance S+N) than light detector 16A (at distance S), the intensity of light detected by light detector 16B should be less than the intensity of light detected by light detector 16A. Due to the close proximity of detectors 16A, 16B to one another, the difference between the intensity of light detected by detector 16A and the intensity of light detected by detector 16B should be attributable only to the difference in distance from light emitter 15. In some examples, processing circuitry of IMD 10 may use the difference between the electrical signals generated by light detectors 16A, 16B, in addition to the electrical signals themselves, in determining an $StO_2$ value of patient 4.

Light emitter 15 also may emit light into a target site of patient 4 during a technique for determining an $SpO_2$ value of patient 4, which may serve as an approximation of $SaO_2$. As with the target site for determining the $StO_2$ value of patient 4 described above, the target site for determining $SpO_2$ generally may include the blood within blood vessels in the interstitial space around IMD 10 when 1 MB 10 is implanted in patient 4. Techniques for determining an $SpO_2$ value of patient 4 may include using one or more of the components of 1 MB 10 used in techniques for determining an $StO_2$ value of patient 4, although the wavelengths of light emitted by light emitter 15 for determining the $SpO_2$ value may differ from wavelengths used to determine the $StO_2$ value.

For example, techniques for determining $SpO_2$ may include using light emitter 15 to emit light at one or more VIS wavelengths (e.g., approximately 600 nm) and at one or more NIR wavelengths (e.g., approximately 850-940 nm). In some such examples, processing circuitry of IMD 10 may control light emitter 15 to sequentially emit light at the one or more VIS wavelengths and the one or more NIR wavelengths for a duration such as 10-30 seconds. Light detectors 16A, 16B each may receive light from light emitter 15 that is reflected by the tissue, and generate electrical signals indicating the intensities of the light detected by light detectors 16A, 16B. Processing circuitry of IMD 10 then may process the signals generated by light detectors 16A, 16B during all or part of the duration. The combination of VIS and NIR wavelengths may help enable processing circuitry of IMD 10 to distinguish oxygenated hemoglobin from deoxygenated hemoglobin in the blood of patient 4, because oxygenated hemoglobin absorbs more NIR light than VIS light, whereas deoxygenated hemoglobin absorbs more VIS light than NIR light. By comparing the amount of VIS light detected by light detectors 16A, 16B to the amount of NIR light detected by light detectors 16A, 16B, processing circuitry of IMD 10 may determine the relative amounts of oxygenated and deoxygenated hemoglobin in the blood of patient 4. For example, if the amount of oxygenated hemoglobin in the blood of patient 4 decreases, the amount of VIS light detected by light detectors 16A, 16B increases and the amount of NIR light detected by light detectors 16A, 16B decreases. Similarly, if the amount of oxygenated hemoglobin in the blood of patient 4 increases, the amount of VIS light detected by light detectors 16A, 16B decreases and the amount of NIR light detected by light detectors 16A, 16B increases.

In order to determine the proportion of the oxygenated hemoglobin that is attributable to pulsatile blood volume, and thus determine $SpO_2$, processing circuitry of IMD 10 also may determine the amount of fluctuation in light absorption that occurs during cardiac cycles of patient 4. Since light absorption is increased with an increase in blood volume during systole and decreased with a decrease in blood volume during diastole, processing circuitry of IMD 10 may determine the fluctuation of light absorption that occurs during cardiac cycles of patient 4 and attribute the value of the fluctuation to pulsatile (i.e., arterial) blood. Processing circuitry of IMD 10 then may determine an $SpO_2$ value of patient 4 based on a combination of the proportion of oxygenated hemoglobin in the blood of patient 4 and the value of the fluctuation in light absorption that occurs during a cardiac cycle of patient 4.

For example, processing circuitry of IMD 10 may evaluate the signals received from light detectors 16A, 16B to determine the $SpO_2$ value of patient 4 (e.g., "signal;" or ratio of ratios "R") by determining a ratio-of-ratios of light absorption at the VIS wavelength (e.g., approximately 600 nm) to light absorption at the NIR wavelength (e.g., approximately 850 nm) according to the following equation:

$$Signal = \frac{(AC/DC)_{600}}{(AC/DC)_{850}}$$

Where $(AC/DC)_{600}$ is a ratio of light absorption by arterial blood to light absorption by other substances (e.g., venous blood or other tissues) at the example VIS wavelength of 600 nm, and $(AC/DC)_{850}$ is a ratio of light absorption of arterial blood to light absorption by other substances at the example NIR wavelength of 850 nm. Because $SpO_2$ may be an approximation of $SaO_2$, determining a ration of the ratios of light absorption by arterial blood to light absorption by other substances at the VIS and NIR wavelengths may enable processing circuitry of IMD 10 to determine the $SpO_2$ value.

Light emitter 15 also may emit light into a target site of patient 4 during a technique for determining an THI value of patient 4. As with the target sites for determining the $StO_2$ and $SpO_2$ values of patient 4 described above, the target site for determining THI generally may include the interstitial space around IMD 10 when IMD 10 is implanted in patient 4. Techniques for determining an THI value of patient 4 may include using one or more of the techniques and components of IMD 10 described above with respect to techniques for determining an $StO_2$ or $SpO_2$ value of patient 4, although in some examples the wavelengths of light emitted by light emitter 15 for determining the THI value may differ from wavelengths used to determine the $StO_2$ and $SpO_2$ values. In some other examples, such techniques may include further processing of signals used in techniques for determining $StO_2$ and $SpO_2$. For example, techniques for determining THI may include using light emitter 15 to emit light at NIR wavelengths of one or more (e.g., each) of approximately 680 nm, 720 nm, 760 nm, and 800 nm to measure a THI value of a volume of tissue of patient 4. In some examples, the emitted wavelengths may be used to determine an $StO_2$ value of the volume of tissue of patient 4, and processing circuitry of IMD 10 then may determine a THI value corresponding to the volume of tissue based on the $StO_2$ value. In some examples, processing circuitry of IMD 10 may determine the THI value according to the following equation:

$$THI = \frac{M_{SO2}(2D_{720})}{PSF}$$

Where $M_{SO2}$ is a linear slope coefficient value, $2D_{720}$ is the second-derivative attenuation measurement centered at 720 nm, and PSF is a probe scaling factor that can be used to obtain a common THI scale between different optical probe spacings or optical path lengths. As with techniques for determining $StO_2$ and $SpO_2$ values, techniques for determining THI values that include using light emitter 15 to emit light at more than one NIR wavelength advantageously may provide enhanced detection of hemoglobin chromophores in tissue, while reducing effects of confounding factors, such as optical coupling, heterogeneity, fouling, change in tissue composition, and/or detection of other chromophores that may be present in the tissue (e.g., myoglobin).

In examples in which a method of determining a health status of patient 4 includes determining one or more of a current HR value, a current HRV value, or a current Z value of patient 4, IMD 10 may include a proximal electrode 38A and a distal electrode 38B. As shown in the illustrated example, proximal electrode 38A may be positioned on header assembly 32, and distal electrode 38B may be formed from an uninsulated distal portion of conductive housing 14. Proximal electrode 38A and distal electrode 38B may be positioned near respective proximal and distal ends 22 and 24 of IMD 10, such that a spacing between proximal electrode 38A and distal electrode 38B may range from about 30-55 mm, about 35-55 mm, or about 40-55 mm, or more generally from about 25-60 mm. In some examples, IMD 10 also may include one or more additional electrodes 38C, 38D positioned on one or both of major surfaces 18, 20 of IMD 10. In any such examples, electrical feedthroughs may provide electrical connection of electrodes 38A-38D, and antenna 26, to circuitry within housing 14.

In the example shown in FIG. 2, proximal electrode 38A is in close proximity to proximal end 22, and distal electrode 38B is in close proximity to distal end 24 of IMD 10. In this example, distal electrode 38B is not limited to a flattened, outward facing surface, but may extend from first major surface 18, around rounded edges 28 or end surface 30, and onto the second major surface 20 in a three-dimensional curved configuration. As illustrated, proximal electrode 38A is located on first major surface 18 and is substantially flat and outward facing. However, in other examples not shown here, proximal electrode 38A and distal electrode 38B both may be configured like proximal electrode 38A shown in FIG. 2, or both may be configured like distal electrode 38B shown in FIG. 2. Any of electrodes 38A-38D may be formed of a biocompatible conductive material. For example, any of electrodes 38A-38D may be formed from any of stainless steel, titanium, platinum, iridium, or alloys thereof. In addition, electrodes of IMD 10 may be coated with a material such as titanium nitride or fractal titanium nitride, although other suitable materials and coatings for such electrodes may be used.

Proximal electrode 38A and distal electrode 38B may be used to sense cardiac EGM signals (e.g., ECG signals) when IMD 10 is implanted subcutaneously in patient 4. In the techniques described herein, processing circuitry of IMD 10 may determine HR and/or HRV values based on cardiac ECG signals. In some examples, processing circuitry of IMD 10 also may determine whether cardiac ECG signals of patient 4 are indicative of arrhythmia (e.g., the presence or absence of atrial fibrillation and a ventricular rate during atrial fibrillation) or other abnormalities, which processing circuitry of IMD 10 may evaluate in determining whether a cardiac function of patient 4 has changed. The cardiac ECG signals may be stored in a memory of the IMD 10, and data derived from the cardiac ECG signals may be transmitted via integrated antenna 26 to another medical device, such as external device 12.

In some examples, one or both of electrodes 38A and 38B also may be used to detect subcutaneous impedance value Z for assessing a congestion status of patient 4, and/or may be used by communication circuitry of IMD 10 for TCC communication with external device 12. For example, processing circuitry of IMD 10 may determine a Z value of patient 4 based on signals received from electrodes 38A, 38B. Processing circuitry of IMD 10 may generate one of a current or voltage signal, deliver the signal via electrodes 38A, 38B, and measure the resulting other of current or voltage. Thus, processing circuitry of IMD 10 may determine an impedance signal based on the delivered current or voltage and the measured voltage or current. In some examples, a trending decrease in Z values over time may indicate fluid overload and an increased likelihood of heart failure hospitalization due to lung congestion.

In some cases, it may be advantageous to use separate electrode pairs for determining the current HR/HRV and Z values of patient 4. For example, electrodes 38C and 38D may be used to detect subcutaneous impedance value Z, in addition to or instead of electrodes 38A, 38B. In other examples, electrodes 38A, 38B may be used to detect Z, whereas electrodes 38C, 38D may be used for ECG sensing. Using separate electrode pairs for ECG sensing impedance measurement may help reduce a likelihood that a signal generated for determining a Z value may interfere with signals sensed by the electrode pair used for ECG sensing. In addition, using separate electrode pairs for determining current Z and HR/HRV values of patient 4 may better enable adaptation of one or more aspects of electrodes 38A-38D (e.g., size or spacing) to the assigned function of each electrode.

In some examples, IMD 10 may include one or more additional sensors, such as one or more accelerometers (not shown). Such accelerometers may be 3D accelerometers configured to generate signals indicative of one or more types of movement of the patient, such as gross body movement (e.g., activity) of the patient, patient posture, movements associated with the beating of the heart, or coughing, rales, or other respiration abnormalities. In some examples, one or more of such accelerometers may be used, in conjunction with light emitter 15 and light detectors 16A, 16B, to determine a ballistocardiogram (i.e., a measure of motion corresponding to blood ejection at systole) that processing circuitry of IMD 10 may use to determine Z instead of or in addition to an ECG signal from a pair of electrodes 38A-38D. Additionally, or alternatively, one or more of the parameters monitored by IMD 10 (i.e., $StO_2$, $SpO_2$, THI, Z, HR, or HRV) may fluctuate in response to changes in one or more such types of movement. For example, increases in HR sometimes may be attributable to increased patient activity (e.g., exercise or other physical activity as compared to inactivity) or to changes in patient posture, and not necessarily to changes in cardiac function caused by a progression of heart failure. Thus, in some methods of determining a health status of patient 4, it may be advantageous to account for such fluctuations when determining whether a change in a parameter, such as HR, that exceeds a threshold is indicative of a change in a corresponding physiological function.

In such examples, processing circuitry of IMD 10 may receive one or more signals from one or more accelerometers of IMD 10, and determine a value of one or more patient-activity parameters, such as gross body movement. In this example, processing circuitry of IMD 10 may cross-reference the determined patient-activity value with values of one or more other parameters, such as an HR value. If the patient-activity value satisfies a threshold, processing circuitry of IMD 10 may determine that a change in a current HR value, relative to a baseline HR value, that otherwise may indicate a change in cardiac function does not indicate a change in cardiac function of patient 4. In such instances, processing circuitry of patient 4 may designate the HR value as an outlier and not use it in determining a health status of patient 4. In some examples, processing circuitry of IMD 10 may cross-reference the determined activity or posture values with different scaling factors to be applied the $StO_2$, $SpO_2$, THI, Z, HR, or HRV values prior to comparison to a threshold, or to different threshold values to which to compare the measured $StO_2$, $SpO_2$, THI, Z, HR, or HRV values. Although processing circuitry of IMD 10 is described above as being configured to receive signals from one or more accelerometers, light emitter 15, light detectors 16A, 16B, and/or electrodes 38A-38D of IMD 10 and determine a value of one or more parameters of patient 4 based on such signals, any steps described herein as being carried out by processing circuitry of IMD 10 may carried out by processing circuitry of one or more devices. For example, processing circuitry of external device 12, or any other suitable implantable or external device or server, may be configured to receive signals from the one or more accelerometers, light emitter 15, light detectors 16A, 16B, and/or electrodes 38A-38D of IMD 10, such as via communication circuitry of IMD 10.

FIG. 3 is a functional block diagram illustrating an example configuration of IMD 10 of FIGS. 1 and 2. In the illustrated example, IMD 10 includes processing circuitry 50 sensing circuitry 52, communication circuitry 54, memory 56, switching circuitry 58, sensors 62, timing/control circuitry 64, in addition to previously-described electrodes 38A-38D, one or more of which may be disposed within housing 14 of IMD 10, and light emitter 15. In some examples, memory 56 includes computer-readable instructions that, when executed by processing circuitry 50, cause IMD 10 and processing circuitry 50 to perform various functions attributed to IMD 10 and processing circuitry 50 herein. Memory 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Timing and control circuitry 64 may be embodied as hardware, firmware, software, or any combination thereof. In some examples, timing and control circuitry 64 may comprise a dedicated hardware circuit, such as an ASIC, separate from other processing circuitry 50 components, such as a microprocessor, or a software module executed by a component of processing circuitry 50 (e.g., a microprocessor or ASIC). Timing and control circuitry 64 may monitor the passage of time to determine when a monitoring period has elapsed, and help control IMD 10 to measure current values of $StO_2$, $SpO_2$, and THI of patient 4. Timing and control circuitry 64 also may control IMD 10 to transmit a heart failure status of patient 4 to external device 12, at the conclusion of a corresponding interval.

In some examples, timing and control circuitry 64 may be configured to associate current values of $StO_2$, $SpO_2$, and THI (and/or current values of Z, HR, or HRV) with a particular time of day, such as day time or night time, so as to enable processing circuitry 50 to take into account a circadian rhythm of patient 4 when determining heart failure, pulmonary, and/or anemia statuses of patient 4. For example, HR values of patient 4 generally may decrease when patient 4 is asleep (e.g., nighttime), and increase when patient 4 is awake (e.g., daytime). Thus, IMD 10 may be configured to use different (e.g., lower) baseline value and/or threshold values for a particular parameter, such as HR, at times when patient 4 is likely to be asleep than when patient 4 is likely to be awake. In some examples in which IMD 10 includes one or more accelerometers, processing circuitry 50 may cross-reference a time of day indicated by timing and control circuitry with accelerometer data, such as to confirm whether patient 4 is asleep or awake as predicted based on the time of day. In this manner, timing and control circuitry 64 may enhance the ability of IMD 10 to accurately determine a health status of patient 4.

In addition to sensed physiological parameters of patient 4 (e.g., determined values of $StO_2$, $SpO_2$, and THI), one or more time intervals for timing the measurements of $StO_2$, $SpO_2$, and THI by processing circuitry 50 may be stored by memory 56 in stored measurements/intervals 68. For example, the intervals 68 stored by memory 56 may instruct processing circuitry 50 to measure current values of $StO_2$, $SpO_2$, and THI of patient 4 hourly, several times daily, daily, or at any other appropriate interval. Stored measurements/intervals 68 also may include intervals at which processing circuitry may be configured to transmit a heart failure status of patient 4 to external device 12, such as daily, weekly, or at any other suitable interval. In some examples, processing circuitry 50 may select intervals for measuring $StO_2$, $SpO_2$, and THI or for transmitting a heart failure status of patient 4 from stored measurements/intervals 68. In other examples, a clinician may select interval values depending upon the needs of patient 4, such as by using an app on a tablet or other smart device, which in some examples may be external device 12.

As illustrated in FIG. 3, memory 56 also may include one or more tables 70 for storing baseline, threshold, and evidence level values. As described above, in some examples, processing circuitry 50 of IMD 10 may be configured to determine baseline values of $StO_2$, $SpO_2$, and THI during a learning phase of IMD 10, which then may be stored in tables 70. In addition, tables 70 may include pre-programmed baseline values that a clinician may select for patient 4 during setup of IMD 10, or baseline values that a clinician may manually enter based on the clinician's assessments of patient 4. Processing circuitry 50 also may be configured to determine threshold values for deviations of current values of $StO_2$, $SpO_2$, and THI from the baseline values, and store the threshold values in tables 70. In some examples, processing circuitry 50 may determine such threshold values based, at least in part, on baseline values selected for patient 4. In addition to the baseline values, tables 70 may include threshold values that a clinician may select for patient 4 during setup of IMD 10, or threshold values that a clinician may manually enter based on the clinician's assessments of patient 4. Tables 70 also may include values for evidence levels that may be associated with certain values of $StO_2$, $SpO_2$, and THI that may be used by processing circuitry 50 to determine a diagnostic score of patient 4. As described above, a health status may comprise a diagnostic score of patient 4, which in some examples may be a composite diagnostic score based on a combination of values of evidence levels associated with one or more current values of $StO_2$, $SpO_2$, and THI of patient 4.

Sensing circuitry 52 and communication circuitry 54 may be selectively coupled to electrodes 38A-38D via switching circuitry 58, as controlled by processing circuitry 50. Sensing circuitry 52 may monitor signals from electrodes 38A-38D in order to monitor electrical activity of heart (e.g., to produce an ECG for HR/HRV determination) or subcutaneous tissue impedance Z (e.g., as a measure of congestion). Sensing circuitry 52 also may monitor signals from sensors 62, which may include light detectors 16A, 16B, and any additional light detectors or accelerometers that may be positioned on IMD 10. In some examples, sensing circuitry 52 may include one or more filters and amplifiers for filtering and amplifying signals received from one or more of electrodes 38A-38D and/or light detectors 16A, 16B.

In some examples, processing circuitry 50 also may include a rectifier, filter and/or amplifier, a sense amplifier, comparator, and/or analog-to-digital converter. Upon receiving signals from electrodes 38A-38D and light detectors 16A, 16B via sensing circuitry 52, processing circuitry 50 may determine current values for each of $StO_2$, $SpO_2$, and THI for patient 4. Processing circuitry then may compare the current values of $StO_2$, $SpO_2$, and THI to the baseline levels stored in tables 70, and determine whether differences between the current values and the corresponding baseline levels exceed corresponding thresholds stored in tables 70.

The threshold values stored in tables 70 may be associated with changes in certain parameters of a health status of patient 4. For example, a threshold value corresponding to one or more of the $StO_2$, Z, HR, or HRV values may be associated with a change in a heart failure status of patient 4, whereas a threshold value corresponding to the $SpO_2$ value may be associated with a change in a pulmonary status of patient 4, and a threshold value corresponding to the THI value may be associated with a change in an anemia status of patient 4. In some examples, processing circuitry 50 may identify evidence level values associated with the current values of $StO_2$, $SpO_2$, and THI of patient 4, and determine a diagnostic score associated with a combination of the evidence levels. Processing circuitry 50 may store the determined current values, associated evidence levels, and diagnostic score in stored measurements/intervals 68 of memory 56, along with an indication of a date and time of the measurements. Simultaneously or thereafter, processing circuitry 50 may transmit, via communication circuitry 54, the diagnostic score and/or one or more additional indicators of a health status of patient 4 to external device 12.

Communication circuitry 54 may include any suitable hardware, firmware, software or any combination thereof for communicating with another device, such as external device 12 or another IMD or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. In some examples, communication circuitry 54 may communicate with external device 12. In addition, processing circuitry 50 may communicate with a networked computing device via an external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device. In some examples, the clinician may select baseline values, threshold values, times of day for $StO_2$, $SpO_2$, and THI measurements, or a number of measurements to be completed during a period, e.g., day, and may program evidence levels to be associated with the parameters of $StO_2$, $SpO_2$, and THI.

The various components of IMD 10 may be coupled a power source, which may include a rechargeable or non-rechargeable battery positioned within housing 14 of IMD 10. A non-rechargeable battery may be selected to last for several years, while a rechargeable battery may be inductively charged from an external device, e.g., on a daily or weekly basis.

FIGS. 4A and 4B illustrate two additional example IMDs that may be substantially similar to IMD 10 of FIGS. 1-3, but which may include one or more additional features. The components of FIGS. 4A and 4B may not necessarily be drawn to scale, but instead may be enlarged to show detail. FIG. 4A is a block diagram of a top view of an example configuration of an IMD 10A. FIG. 4B is a block diagram of a side view of example IMD 10B, which may include an insulative layer as described below.

FIG. 4A is a conceptual drawing illustrating another example IMD 10A that may be substantially similar to IMD 10 of FIG. 1. In addition to the components illustrated in FIGS. 1-3, the example of IMD 10 illustrated in FIG. 4A also may include a body portion 72 and an attachment plate 74. Attachment plate 74 may be configured to mechanically couple header 32 to body portion 72 of IMD 10A. Body portion 72 of IMD 10A may be configured to house one or more of the internal components of IMD 10 illustrated in FIG. 3, such as one or more of processing circuitry 50, sensing circuitry 52, communication circuitry 54, memory 56, switching circuitry 58, internal components of sensors 62, and timing/control circuitry 64. In some examples, body portion 72 may be formed of one or more of titanium, ceramic, or any other suitable biocompatible materials.

FIG. 4B is a conceptual drawing illustrating another example IMD 10B that may include components substantially similar to IMD 10 of FIG. 1. In addition to the components illustrated in FIGS. 1-3, the example of IMD 10B illustrated in FIG. 4B also may include a wafer-scale insulative cover 76, which may help insulate electrical signals passing between electrodes 38A-38D and/or light detectors 16A, 16B on housing 14B and processing circuitry 50. In some examples, insulative cover 76 may be positioned over an open housing 14 to form the housing for the components of IMD 10B. One or more components of IMD 10B (e.g., antenna 26, light emitter 15, light detectors 16A, 16B, processing circuitry 50, sensing circuitry 52, communication circuitry 54, switching circuitry 58, and/or timing/control circuitry 64) may be formed on a bottom side of insulative cover 76, such as by using flip-chip technology. Insulative cover 76 may be flipped onto a housing 14B. When flipped and placed onto housing 14B, the components of IMD 10B formed on the bottom side of insulative cover 76 may be positioned in a gap 78 defined by housing 14B.

Insulative cover 76 may be configured so as not to interfere with the operation of IMD 10B. For example, one or more of electrodes 38A-38D may be formed or placed above or on top of insulative cover 76, and electrically connected to switching circuitry 58 through one or more vias (not shown) formed through insulative cover 76. In addition, to enable IMD to determine values of $StO_2$, $SpO_2$, and THI, at least a portion of insulative cover 76 may transparent to the NIR or visible wavelengths emitted by light emitter 15 and detected by light detectors 16A, 16B, which in some examples may be positioned on a bottom side of insulative cover 76 as described above.

In some examples, light emitter 15 may include an optical filter between light emitter 15 and insulative cover 76, which may limit the spectrum of emitted light to be within a narrow band. Similarly, light detectors 16A, 16B may include optical filters between light detectors 16A, 16B and insulative cover 76, so that light detectors 16A, 16B detects light from a narrow spectrum, generally at longer wavelengths than the emitted spectrum. Other optical elements that may be included in the IMD 10B may include index matching layers, antireflective coatings, or optical barriers, which may be configured to block light emitted sideways by the light emitter 15 from reaching light detector 40.

Insulative cover 76 may be formed of sapphire (i.e., corundum), glass, parylene, and/or any other suitable insulating material. Sapphire may be greater than 80% transmissive for wavelengths in the range of about 300 nm to about 4000 nm, and may have a relatively flat profile. In the case of variation, different transmissions at different wavelengths may be compensated for, such as by using a ratiometric approach. In some examples, insulative cover 76 may have a thickness of about 300 micrometers to about 600 micrometers. Housing 14B may be formed from titanium or any other suitable material (e.g., a biocompatible material), and may have a thickness of about 200 micrometers to about 500 micrometers. These materials and dimensions are examples only, and other materials and other thicknesses are possible for devices of this disclosure.

Figure 5:
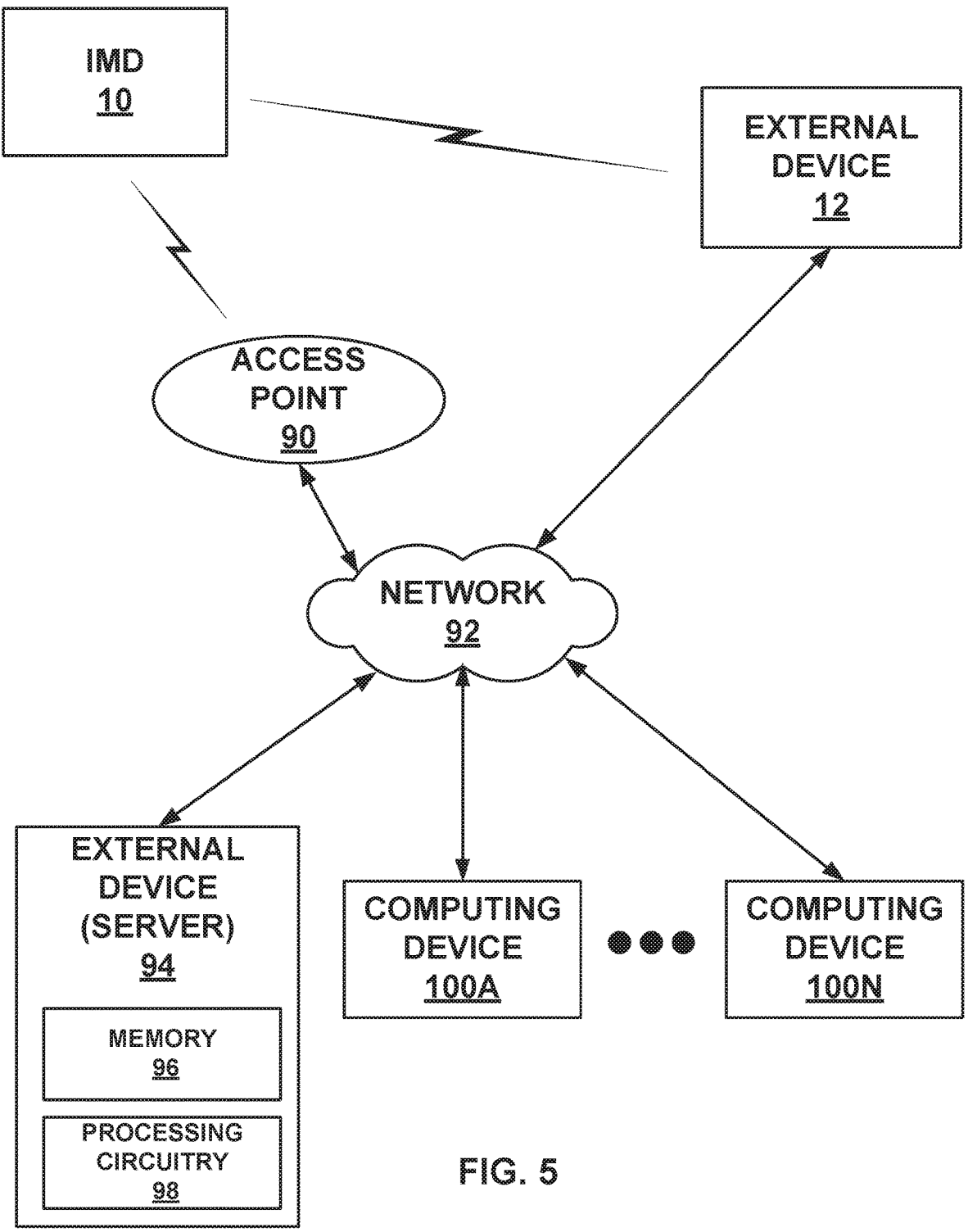
FIG. 5 is a block diagram illustrating an example system that includes an external device, such as a server, and one or more computing devices that are coupled to the leadless implantable medical device of FIG. 1 and the external device of FIG. 1 via a network.

FIG. 5 is a functional block diagram illustrating an example system that includes an access point 90, a network 92, external computing devices, such as a server 94, and one or more other computing devices 100A-100N, which may be coupled to IMD 10, external device 12, and external device 12 via network 92. In this example, IMD 10 may use communication circuitry 54 to communicate with external device 12 via a first wireless connection, and to communicate with an access point 90 via a second wireless connection. In the example of FIG. 5, access point 90, external device 12, server 94, and computing devices 100A-100N are interconnected and may communicate with each other through network 92.

Access point 90 may comprise a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. As discussed above, IMD 10 may be configured to transmit data, such as current values and heart failure statuses, to external device 12. In addition, access point 90 may interrogate IMD 10, such as periodically or in response to a command from the patient or network 92, in order to retrieve current values or heart failure statuses determined by processing circuitry 50 of IMD 10, or other operational or patient data from IMD 10. Access point 90 may then communicate the retrieved data to server 94 via network 92.

In some cases, server 94 may be configured to provide a secure storage site for data that has been collected from IMD 10, and/or external device 12. In some cases, server 94 may assemble data in web pages or other documents for viewing by trained professionals, such as clinicians, via computing devices 100A-100N. One or more aspects of the illustrated system of FIG. 5 may be implemented with general network technology and functionality, which may be similar to that provided by the Medtronic CareLink® Network developed by Medtronic plc, of Dublin, Ireland.

In some examples, one or more of computing devices 100A-100N (e.g., device 100A) may be a tablet or other smart device located with a clinician, by which the clinician may program, receive alerts from, and/or interrogate IMD 10. For example, the clinician may access patient 4's $StO_2$, $SpO_2$, and THI measurements through device 100A, such as when patient 4 is in in between clinician visits, to check on a health status of patient 4 as desired. In some examples, the clinician may enter instructions for a medical intervention for patient 4 into an app in device 100A, such as based on a heart failure status of patient 4 determined by IMD 10, or based on other patient data known to the clinician. Device 100A then may transmit the instructions for medical intervention to another of computing devices 100A-100N (e.g., device 100B) located with patient 4 or a caregiver of patient 4. For example, such instructions for medical intervention may include an instruction to change a drug dosage, timing, or selection, to schedule a visit with the clinician, or to seek medical attention. In further examples, device 100B may generate an alert to patient 4 based on a health status of patient 4 determined by IMD 10, which may enable patient 4 proactively to seek medical attention prior to receiving instructions for a medical intervention. In some examples, the alert generated by device 100B may include an updated diagnosis of one or more of a heart failure condition, a pulmonary disorder, and anemia, such as a diagnosis that a heart failure condition of patient 4 has progressed from a first type of heart failure condition to a second type of heart failure condition. In this manner, patient 4 may be empowered to take action, as needed, to address his or her health status, which may help improve clinical outcomes for patient 4.

FIGS. 6-12 are flow diagrams illustrating various techniques related to determining a health status of a patient based on a comparison of current $StO_2$, $SpO_2$, and THI values of the patient to corresponding baseline values, in accordance with examples of this disclosure. As described herein, the techniques illustrated FIGS. 6-12 may be employed using one or more components of system 2, which have been described above with respect to FIGS. 1-5. Although described as being performed by IMD 10, the techniques of FIGS. 6-12 may be performed, in whole or in part, by processing circuitry and memory of other devices of a medical device system, as described herein. For example, although processing circuitry 50 of IMD is described as carrying out most of the example techniques illustrated in FIGS. 6-9 for the sake of clarity, in other examples, one or more devices (e.g., external device 12 or other external device or server) or a clinician may carry out one or more steps attributed below to processing circuitry 50 of IMD 10.

Figure 6:
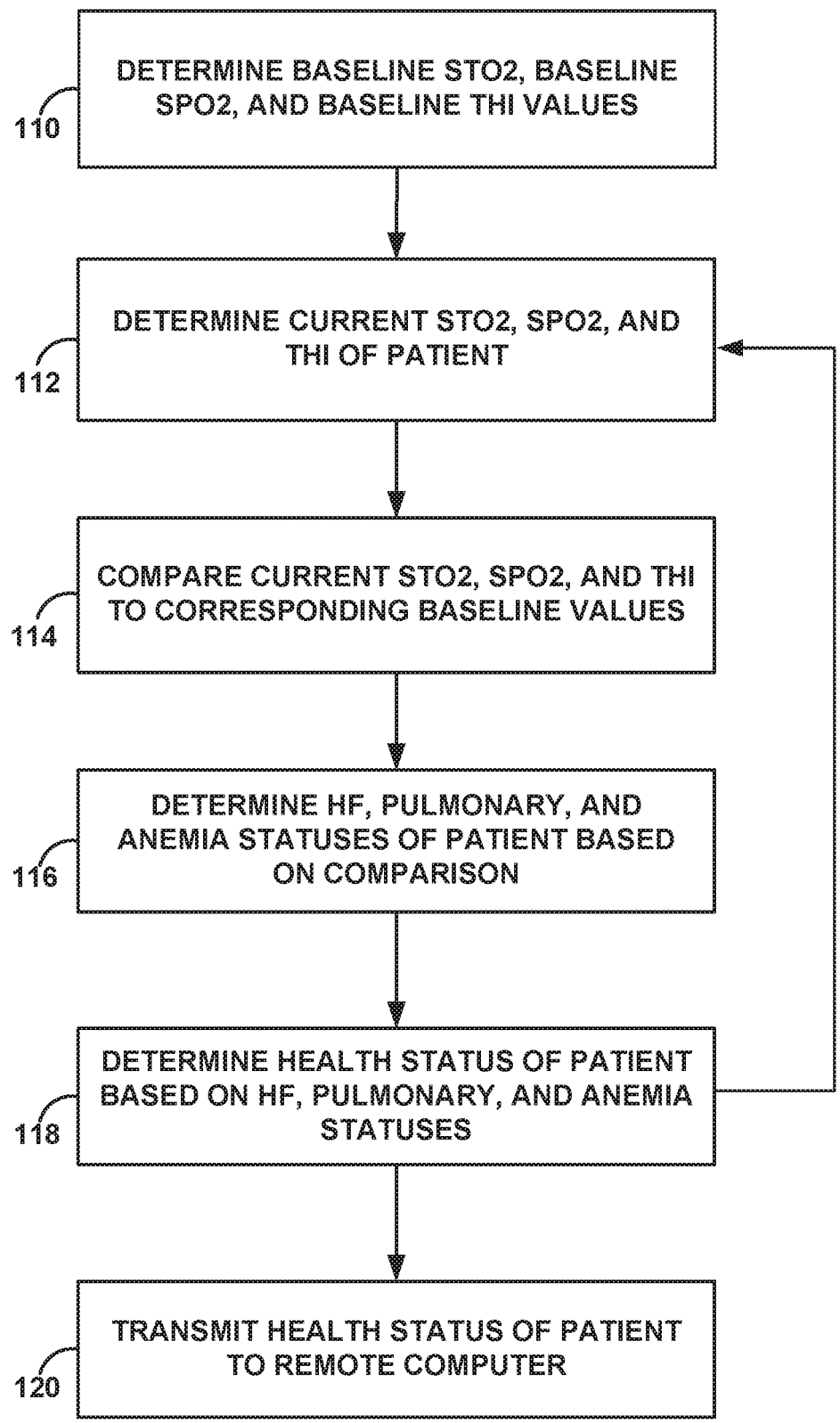
FIG. 6 is a flow diagram illustrating an example technique for determining a health status of a patient by determining heart failure, pulmonary, and anemia statuses of the patient based on based on comparisons of respective ones of current tissue oxygen saturation, pulsatile oxygen saturation, and tissue hemoglobin index values to corresponding baseline values, and transmitting the health status to a remote computer.

FIG. 6 is a flow diagram illustrating an example technique for determining, by processing circuitry 50 of IMD 10, a health status of patient 4 based on a comparison of current tissue oxygen saturation, impedance, and pulse transit time values (i.e., $StO_2$, $SpO_2$, and THI) of patient 4 to corresponding baseline values stored in tables 70 of memory 56, and transmitting the health status to external device 12. According to the example of FIG. 6, IMD 10 may determine baseline $StO_2$, $SpO_2$, and THI values for patient 4 (110). For example, such baseline $StO_2$, $SpO_2$, and THI values may represent baseline first, second, and third optical signals received by processing circuitry 50 of IMD 10 from at least one optical sensor, such as one or more of light detectors 16A, 16B. In some examples, IMD 10 may determine the baseline values during a learning phase of IMD 10 following implantation of IMD 10 into patient 4, as discussed above with respect to FIG. 1. Such a learning phase may take place after implantation of IMD 10 at a time that a heart failure condition of patient 4 is stable (e.g., compensated).

During the learning phase, IMD 10 periodically may determine current values of $StO_2$, $SpO_2$, and THI of patient 4 based on signals received from one or more of electrodes 38A-38D, light emitter 15, and light detectors 16A, 16B and store the values in stored measurements/intervals 68. IMD 10 then may analyze the collected values of $StO_2$, $SpO_2$, and THI to determine the baseline values for patient 4 (110). In some examples, IMD 10 may reject any outlier values of $StO_2$, $SpO_2$, and THI, and average the remaining measurements, although other methods of data analysis may be used to determine the baseline values from the collected values. In other examples, a clinician may determine baseline values for patient 4 by selecting baseline values stored in tables 70 of IMD 10 may as part of a start-up phase of treatment following the implantation of IMD 10 within patient 4. In some examples, IMD 10 also may determine threshold values for each of the baseline $StO_2$, $SpO_2$, and THI values for patient 4. For example, processing circuitry 50 may determine the threshold values for patient 4 based on the determined baseline values for patient 4 by selecting the threshold values from tables 70. In other examples, a clinician may select threshold values for patient 4, which IMD then may associate with the baseline values of $StO_2$, $SpO_2$, and THI for patient 4 in tables 70.

After IMD 10 has determined baseline and/or threshold values of $StO_2$, $SpO_2$, and THI for patient 4, such as at the conclusion of a learning phase of IMD 10, IMD 10 may begin determining current values of $StO_2$, $SpO_2$, and THI for patient 4 (112). For example, processing circuitry 50 of IMD 10 may receive signals from one or more of electrodes 38A-38D, light emitter 15, and light detectors 16A, 16B, and determine current values of $StO_2$, $SpO_2$, and THI based on these signals, as described above with respect to FIGS. 1-3. Next, processing circuitry 50 of IMD 10 may compare the current $StO_2$, $SpO_2$, and THI values of patient 4 to corresponding baseline values of patient 4 stored in tables 70, and determine a difference between each of the current values of $StO_2$, $SpO_2$, and THI and the corresponding baseline values (114). In some examples, processing circuitry 50 also may determine whether a difference between one or more of the current values and the corresponding baseline values satisfies a threshold value.

Based on the differences between the current values and the baseline value determined at (114) and/or the determination of whether one or more of the differences exceed a threshold value, processing circuitry 50 determines corresponding heart failure, pulmonary, and anemia statuses of patient 4 (116). Then, processing circuitry 50 determines a health status of patient 4 based on a combination of the heart failure, pulmonary, and anemia statuses (118). In some examples, a threshold value may be an absolute value of a percentage of the baseline value. For example, if a baseline value of $StO_2=X$, then a threshold value of $StO_2$ may be $X\pm0.2X$. In other examples, one or more of $StO_2$, $SpO_2$, and THI may be associated with multiple threshold values that correspond to different percentages of the baseline values, which may take into account differences in significance between values that exceed a baseline value and values that are less than a baseline value. For example, if a baseline value of $StO_2=X$, then threshold values of $StO_2$ may be $X+0.2X$ and $X-0.1X$, where values of $StO_2$ that are less than X have relatively greater significance than values of $StO_2$ that are greater than X. In any such examples, the threshold values may be based on deviations from corresponding baseline values, such as standard deviations or any other suitable statistical functions.

IMD 10 may repeat steps 112-118 to periodically determine updated health statuses of patient 4 such as daily, weekly, monthly, or at any other suitable period. In some examples, the health status of patient 4 may comprise a diagnostic score that indicates a likelihood that patient 4 may require hospitalization within a certain period of time, based on changes in one or more of cardiac, lung, or blood functions of patient 4. For example, processing circuitry 50 may determine a diagnostic score of patient 4 based on a combination of values of one or more evidence levels associated with the current values of $StO_2$, $SpO_2$, and THI. In general, evidence levels associated with greater severities of inadequate tissue perfusion (as indicated by a relatively low $StO_2$), inadequate arterial perfusion (as indicated by a relatively low $SpO_2$), and inadequate tissue hemoglobin index (as indicated by a relatively low THI) may have higher values than evidence levels associated with lesser severities of such parameters of corresponding ones of heart failure, pulmonary disorders, and anemia. Thus, a higher diagnostic score may indicate that patient 4 is at a greater risk of acute decompensation and/or hospitalization or other adverse medical events within a certain time period than a lower diagnostic score, or that a particular symptom is being caused by a particular underlying condition of patient 4's heart, lungs, or blood.

In some examples, the diagnostic score also may include an indication of which of a heart failure condition, pulmonary disorder, or anemia of patient 4 is most likely to cause patient 4 to require hospitalization within the period of time, and/or which a of an underlying condition of patient 4's heart, lungs, or blood is likely to be causing a particular symptom. For example, the diagnostic score may indicate that shortness of breath experienced by patient 4 has a 70% likelihood of being caused by a heart failure condition, a 20% likelihood of being caused by a pulmonary disorder, and a 10% likelihood of being caused by anemia. In such an example, processing circuitry 50 thus determines that a heart failure condition is the most likely cause of shortness of breath experienced by patient 4, and may include this determination in the diagnostic score. In some examples, processing circuitry 50 may determine a likelihood of each of a heart failure condition, a pulmonary disorder, and anemia being the cause of a symptom of patient 4 based on an integration of prior population data (e.g., data associated with the evidence levels, described above with respect to FIG. 1) or prior data specific to patient 4, with current measurements specific to patient 4 (e.g., the current values of $StO_2$, $SpO_2$, or THI of patient 4), such as by using Bayesian statistics or other methods of machine learning.

The determination by processing circuitry 50 of a health status of patient 4 based on diagnostic scores is described further with respect to FIG. 8 below. Regardless of whether the health status of patient 4 determined by processing circuitry 50 comprises a diagnostic score, processing circuitry then transmits the health status of patient 4 to a remote computer, such as external device 12 (120).

Figure 7:
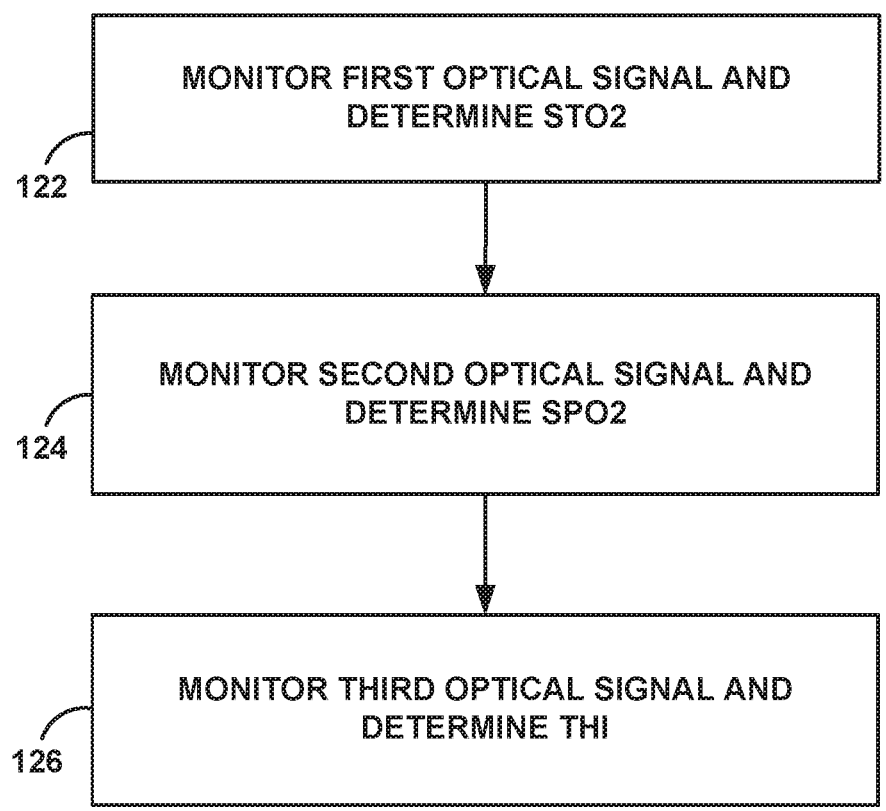
FIG. 7 is a flow diagram illustrating an example technique for determining the baseline or current values of tissue oxygen saturation, pulsatile oxygen saturation, and tissue hemoglobin index of FIG. 6.

FIG. 7 is a flow diagram illustrating an example technique for determining the baseline or current values of tissue oxygen saturation, pulsatile oxygen saturation, and tissue hemoglobin index described with respect to FIG. 6. To determine a current value of $StO_2$ for patient 4, processing circuitry 50 of IMD 10 may monitor a first optical signal. For example, processing circuitry 50 of IMD 10 may cause light emitter 15 to emit NIR light at one or more wavelengths appropriate to $StO_2$ determination, such as the wavelengths described above with respect to FIG. 2. Light detectors 16A, 16B each may receive light from light emitter 15 that is reflected by the tissue, and generate electrical signals indicating the intensities of the light detected by light detectors 16A, 16B. Processing circuitry of IMD 10 then may evaluate the electrical signals from light detectors 16A, 16B in order to determine an $StO_2$ value of patient 4 (122). The $StO_2$ value determined at (122) may be used as current value $StO_2$ of patient 4, which is a measure of tissue oxygen saturation of patient 4 and pertains to a heart failure status of patient 4. For example, a relatively low value of $StO_2$ may indicate a relatively high amount of deoxygenated hemoglobin subcutaneous tissue near IMD 10. Thus, if the current value of $StO_2$ is relatively low and/or is lower than a previous measured value of $StO_2$, patient 4 may be experiencing a decrease in tissue oxygen saturation, which may be reflected in a diagnostic score determined by processing circuitry 50.

To determine a current value of $SpO_2$ for patient 4, processing circuitry 50 of IMD 10 may monitor a second optical signal. For example, processing circuitry 50 may cause light emitter 15 to emit NIR light at one or more wavelengths appropriate to $SpO_2$ determination, such as the wavelengths described above with respect to FIG. 2. Light detectors 16A, 16B each may receive light from light emitter 15 that is reflected by the tissue, and generate electrical signals indicating the intensities of the light detected by light detectors 16A, 16B. Processing circuitry of IMD 10 then may evaluate the electrical signals from light detectors 16A, 16B in order to determine an $SpO_2$ value of patient 4 (124). The $SpO_2$ value determined at (124) may be used as current value $SpO_2$ of patient 4, which is a measure of pulsatile oxygen saturation of patient 4 (e.g., an approximation of arterial oxygen saturation of patient 4) and pertains to a pulmonary status of patient 4. For example, a relatively low value of $SpO_2$ may indicate a relatively low amount of oxygenated blood in the arteries near IMD 10. Thus, if the current value of $SpO_2$ is relatively low and/or is lower than a previous measured value of $SpO_2$, patient 4 may be experiencing a decrease in pulsatile oxygen saturation, which may be reflected in a diagnostic score determined by processing circuitry 50.

To determine a current value of THI for patient 4, processing circuitry 50 of IMD 10 may monitor a third optical signal. For example, processing circuitry 50 may cause light emitter 15 to emit NIR light at one or more wavelengths appropriate to THI determination, such as the wavelengths described above with respect to FIG. 2. Light detectors 16A, 16B each may receive light from light emitter 15 that is reflected by the tissue, and generate electrical signals indicating the intensities of the light detected by light detectors 16A, 16B. Processing circuitry of IMD 10 then may evaluate the electrical signals from light detectors 16A, 16B in order to determine an THI value of patient 4 (126). The THI value determined at (126) may be used as current value THI of patient 4, which is a measure of tissue hemoglobin index of patient 4 and pertains to an anemia status of patient 4. For example, a relatively low value of THI may indicate a relatively low concentration of hemoglobin, relative to tissue volume, in the tissue near IMD 10. Thus, if the current value of THI is relatively low and/or is lower than a previous measured value of THI, patient 4 may be experiencing a decrease in tissue hemoglobin index, which may be reflected in a diagnostic score determined by processing circuitry 50.

In some examples, the current values of one or more of $StO_2$, $SpO_2$, and THI may exhibit random variability. In order to account for such variability, a comparison of the current diagnostic score to the baseline diagnostic score carried out by processing circuitry 50 may include curve fitting and trend analysis. For example, if processing circuitry 50 measures values of $StO_2$, $SpO_2$, and THI several times daily, processing circuitry may accumulate such values over a period of time (e.g., over several days or several weeks) and fit the accumulated values of each of $StO_2$, $SpO_2$, and THI to a corresponding trendline. Then, processing circuitry 50 may use the trendlines to project corresponding current values of $StO_2$, $SpO_2$, and THI. In this manner, processing circuitry 50 may account for random fluctuations when determining current values of $StO_2$, $SpO_2$, and THI as described above, which may enhance the accuracy with which the current values of $StO_2$, $SpO_2$, and THI reflect the heart failure, pulmonary, and anemia statuses of patient 4.

Figure 8:
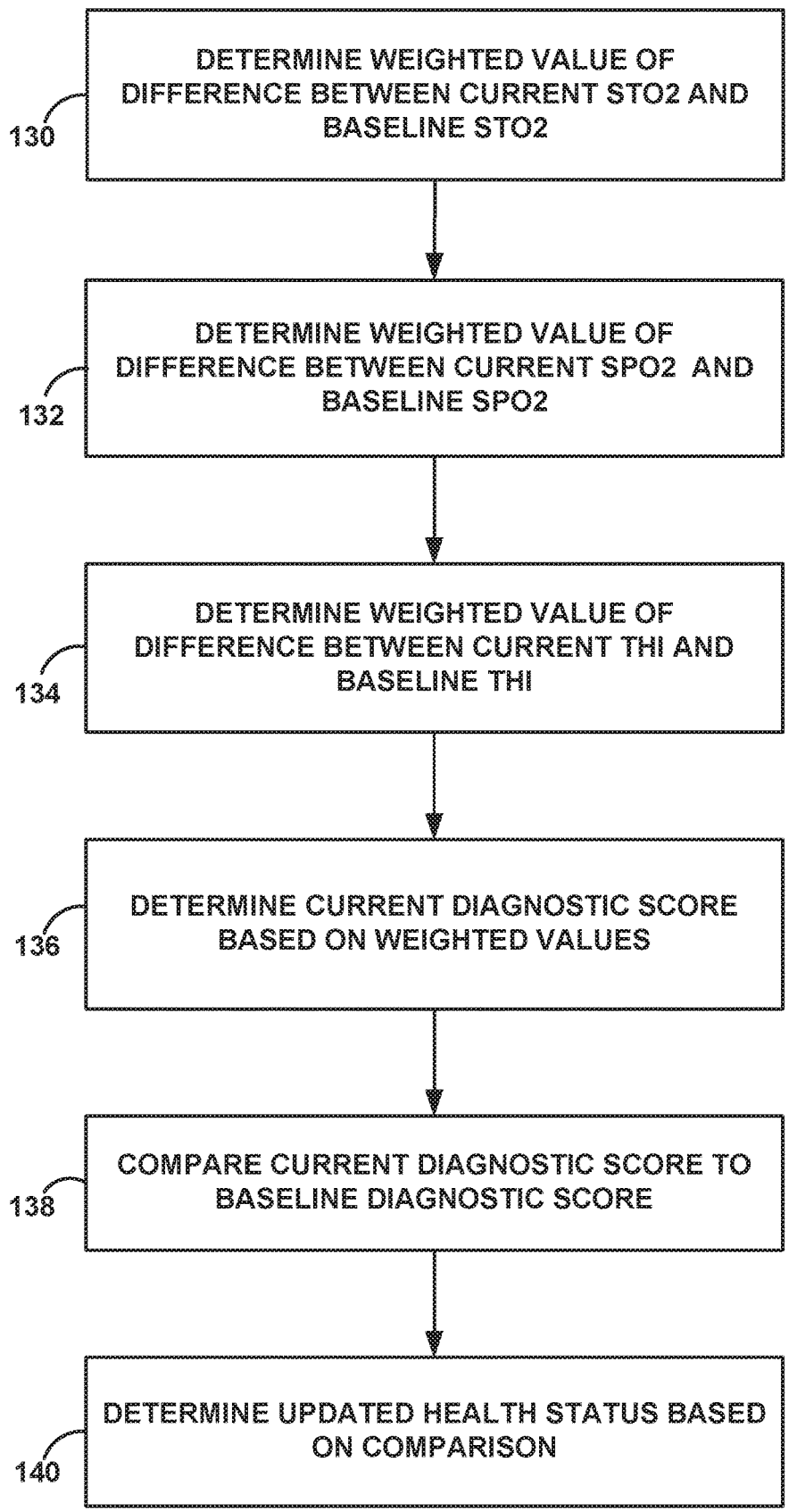
FIG. 8 is a flow diagram illustrating an example technique for determining a current diagnostic score and determining an updated health status of a patient based on a comparison of the current diagnostic score to a baseline diagnostic score.

FIG. 8 is a flow diagram illustrating an example technique for determining, by processing circuitry 50 of IMD 10, a current diagnostic score of patient 4, and determining an updated health status of patient 4 based on a comparison of the current diagnostic score to a baseline diagnostic score. A comparison of a current diagnostic score of patient 4 to a baseline diagnostic score of patient 4 may provide additional information about changes in a health status of patient 4, and may further inform monitoring and treatment decisions and improve clinical outcomes. In some examples, a current diagnostic score may be determined based on weighted values of the differences between current values ($StO_2$, $SpO_2$, and THI) of patient 4 and the corresponding baseline values. For example, processing circuitry 50 may determine a difference between current values of each of $StO_2$, $SpO_2$, and THI and the corresponding baseline values of patient 4, as described with respect to FIG. 6. Then, processing circuitry 50 may determine a weighted value for each of the differences between the current values and the corresponding baseline values. Specifically, processing circuitry 50 determines a weighted value of a difference between the current $StO_2$ and the baseline $StO_2$ of patient 4 (130), a weighted value of a difference between the current $SpO_2$ and the baseline $SpO_2$ of patient 4 (132), and a weighted value of a difference between the current THI and the baseline THI of patient 4 (134).

In some examples, the weights assigned by processing circuitry 50 to the difference values may be based on factors such as a medical history of patient 4. As discussed above with respect to FIG. 1, processing circuitry 50 of IMD 10 may assign such weights based on events in the medical history of patient 4, such as hospital admissions for heart failure, medication changes, history of systolic or diastolic heart failure, hypertension, respiratory illness (e.g., COPD), diabetes, atrial fibrillation, renal failure, one or more blood disorders (e.g., anemia), or one or more sleep disorders (e.g., sleep apnea), among others. For example, patient 4 may have a medical history of becoming anemic, which may indicate that patient 4 is especially likely to become anemic in the future. Or, population-based data may indicate that patients having a same or similar profile of baseline values as patient 4 may be particularly likely to become anemic (or to develop inadequate tissue oxygen saturation or pulsatile oxygen saturation). In such a situation, processing circuitry 50 may assign added weight to the difference between the current THI and the baseline THI, thereby rendering the diagnostic score of patient 4 more sensitive to fluctuations in THI values of patient 4. Similarly, weights assigned by processing circuitry to the difference values may have negative values, such as if a medical history of patient 4 or population-based data indicate that patient 4 is unlikely to become anemic (or to develop inadequate tissue oxygen saturation or pulsatile oxygen saturation).

Processing circuitry 50 then may combine the weighted values of the differences between the current values and the baseline values, to determine a current diagnostic score for patient 4 (136), and then compare the current diagnostic score to a baseline diagnostic score (138). The baseline diagnostic score may be a diagnostic score previously determined by processing circuitry 50 based on values of one or more evidence levels associated with the baseline values of patient 4. For example, the baseline diagnostic score may represent a risk of hospitalization for patient 4 when patient 4 is compensated, such as when the heart failure, pulmonary, and anemia statuses of patient 4 are stable. Processing circuitry 50 then may determine an updated health status of patient 4 based on the comparison of the baseline diagnostic score to the current diagnostic score (140). As in the method of FIG. 6, processing circuitry 50 may transmit the updated health status to a remote computer, such as external device 12. External device 12, or another remote computer, then may transmit instructions for a medical intervention (e.g., a change in a drug regimen, or instructions to schedule a clinician visit or seek medical attention), to an interface of a user device located with patient 4.

In some cases, this method of determining a health status of patient 4 advantageously may provide context to a current diagnostic score determined for patient 4 by taking into consideration the extent to which the current diagnostic score deviates from a baseline diagnostic score. For example, a relatively greater difference between the baseline diagnostic score and the current diagnostic score may indicate a more significant worsening of one or more aspects of patient 4's condition than a relatively smaller difference, even with the current diagnostic score held equal. In examples where a difference between the baseline and current diagnostic scores is relatively great (e.g., satisfies a threshold), external device 12 may transmit instructions for more aggressive medical interventions to a user device than examples in which the difference is smaller. In other examples, patient 4 may be added to a database of particularly at-risk patients, who may be monitored more closely by a clinician or by one or more of the devices described herein. In any such examples, treatment may be further tailored to the specific needs of patient 4 based on the magnitude of changes in patient 4's health status over time.

Figure 9:
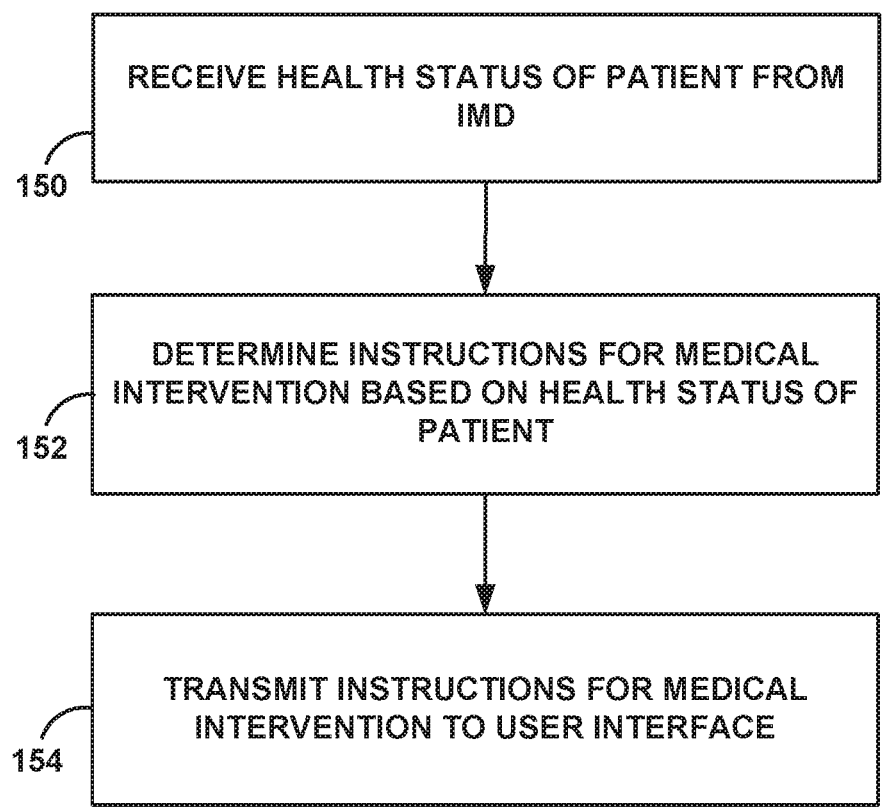
FIG. 9 is a flow diagram illustrating an example technique for a remote computer to determine instructions for a medical intervention based on a health status of a patient received from the leadless implantable medical device of FIG. 1, and transmit the instructions to a user interface.

FIG. 9 is a flow diagram illustrating an example technique for external device 12 to determine instructions for a medical intervention based on a health status of patient 4 received from IMD 10, and transmit the instructions to a user interface. The method illustrated in FIG. 9 may be used with any of the methods for determining a health status by IMD 10 described herein, such as the methods illustrated in FIGS. 6 and 8. In the illustrated example, external device 12 is configured to receive a health status of patient 4 from IMD 10, which may be transmitted to a processing circuitry of external device 12 via communication circuitry 54 and antenna 26 of IMD 10 (150).

In some examples, upon receiving the health status of patient 4 from IMD 10 and prior to determining instructions for a medical intervention for patient 4, external device 12 may transmit one or more queries to a user device. For example, external device 12 may ask patient 4 or a caregiver to answer questions about recent or current activities or symptoms of patient 4, such as whether patient 4 recently has exercised, taken medications, or experienced symptoms. In addition, external device 12 may interrogate IMD 10 for current values of $StO_2$, $SpO_2$, and THI of patient 4, if IMD 10 did not already transmit the current values to external device 12. Based on the heart failure, pulmonary, and anemia statuses of patient 4, and optionally based on answers to queries and/or the current values of patient 4, external device 12 then may determine instructions for a medical intervention for patient 4 (152).

External device 12 may determine instructions for multiple medical interventions for patient 4. For example, external device 12 may determine instructions for each of a heart failure status, a pulmonary status, and an anemia status of patient 4. For example, based on a heart failure status of patient 4, external device 12 may determine instructions for modifying (e.g., start, stop, increase, or decrease) a dose of one or more drugs, such as diuretics, nitrates, beta-blockers, ivabradine, or inotropes. In some examples, instructions for medical interventions for patient 4 may take into account the presence of cardiac arrhythmia, as indicated by ECG signals of patient 4 detected by IMD 10. For example, instructions determined by external device 12 in the presence of arrhythmia may include instructions for patient 4 to avoid taking certain medications, instruct patient 4 to visit a healthcare facility, or may recommend starting CRT or changing CRT parameters. Further, in some examples, processing circuitry of IMD 10 may disregard changes in the Z, $StO_2$, HR, or HRV values that occur during a cardiac arrhythmia. Based on a pulmonary status of patient 4, external device 12 may determine instructions for modifying dosages of one or more of a bronchodilator, steroid, diuretic, or other appropriate drug. Based on an anemia status of patient 4, external device 12 may determine instructions for modifying dosages of one or more drugs, such as an erythropoiesis-stimulating agent, a dietary supplement or instructions for seeking treatment at a healthcare facility (e.g., for a blood transfusion).

In some examples, external device 12 may determine the instructions for medical intervention independent of clinician input, such as by selecting among treatment options stored in a memory of external device 12 or a centralized database that are associated with a diagnostic score and the current values of $StO_2$, $SpO_2$, and THI of patient 4. In other examples, a clinician may determine the instructions for medical intervention on substantially the same basis, and input the instructions to external device 12. External device 12 then may transmit the instructions to an interface of the user device with patient 4 (154). In some examples, external device 12 may transmit follow-up queries to patient 4 or a caregiver via the user device after transmitting the instructions. Such queries may include questions pertaining to patient 4's understanding of the transmitted instructions, whether patient 4 has complied with the instructed medical intervention, and/or whether patient 4 is experiencing symptoms. External device 12 may store patient 4's responses in a memory of external device 12, or in a centralized database. A clinician may review the responses, and remotely follow-up with patient 4 as needed following any changes to patient 4's treatment for one or more of a heart failure condition, a pulmonary disorder, or anemia. In this manner, the techniques and systems described herein advantageously may enable patient 4 to receive individualized, frequently updated treatment at less expense than a comparable number of clinician visits would incur. In addition, the techniques and systems may help reduce cardiac remodeling that may be caused by acute decompensation episodes, which in turn may help minimize the progression of a heart failure condition of patient 4.

Figure 10:
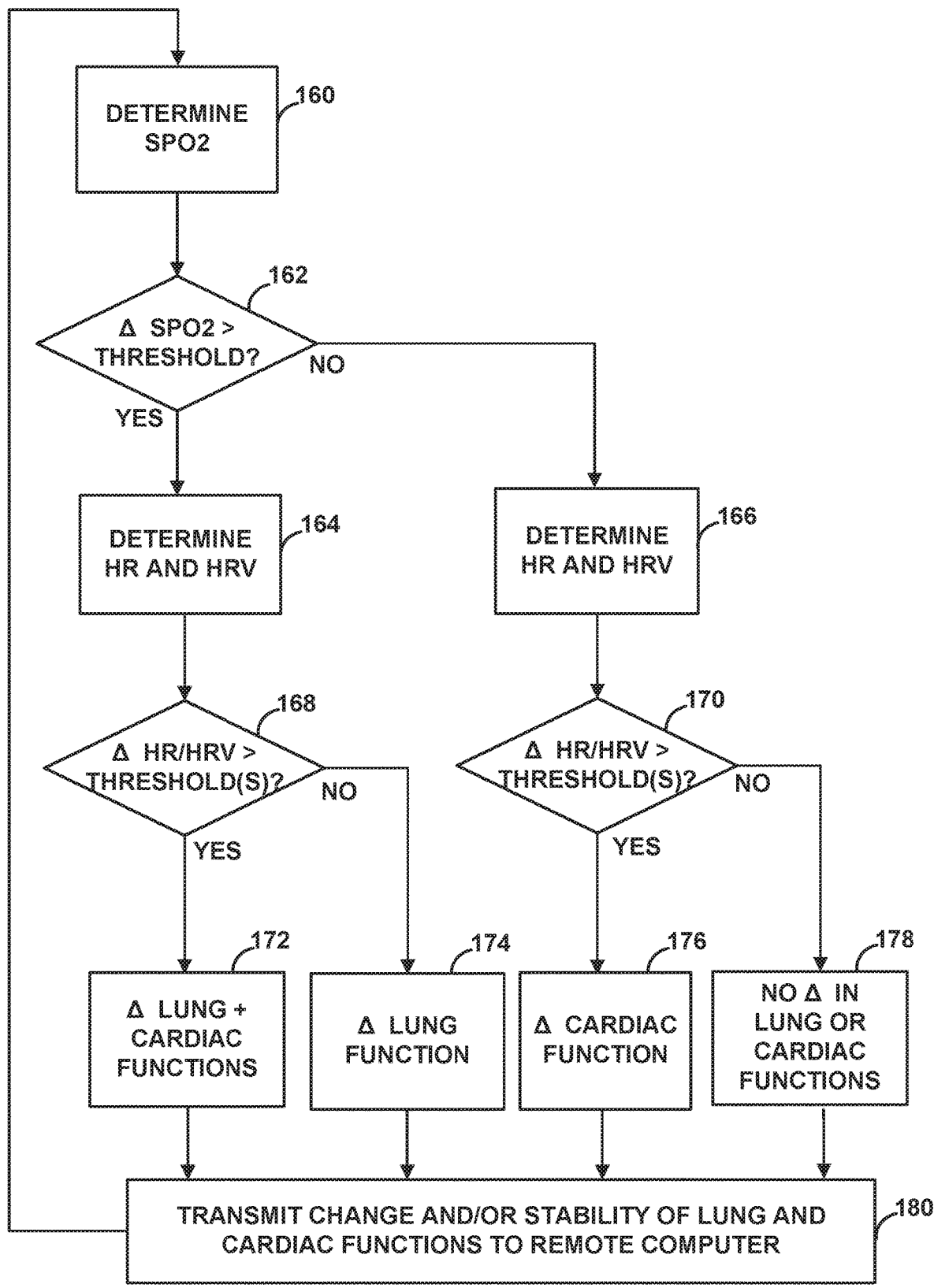
FIG. 10 is a flow diagram illustrating an example technique for determining changes in the patient's lung and/or cardiac functions based on trends in the patient's pulsatile oxygen saturation, heart rate, and heart rate variability values.
Figure 11:
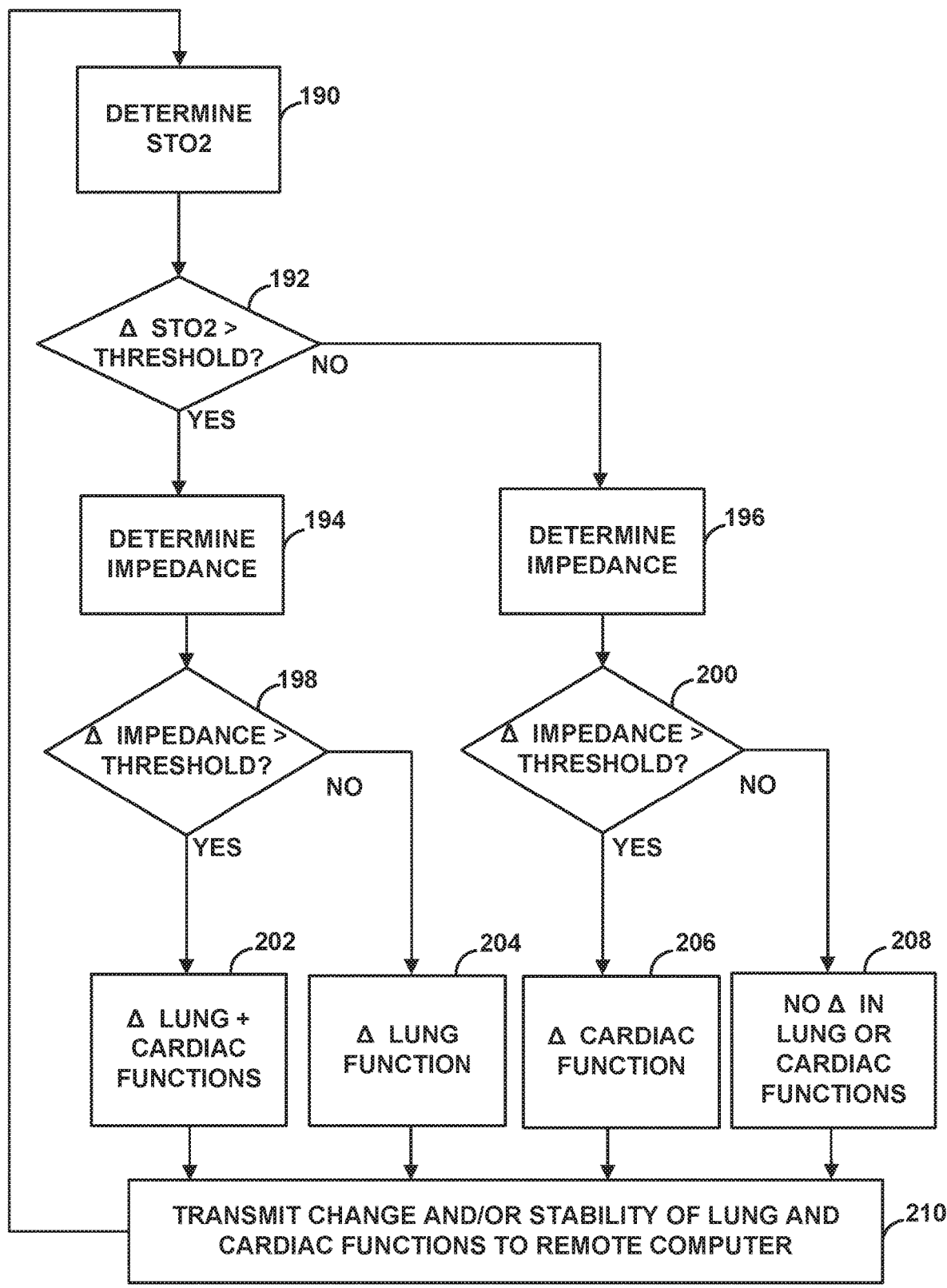
FIG. 11 is a flow diagram illustrating an example technique for determining changes in the patient's lung and/or cardiac functions based on trends in the patient's tissue oxygen saturation and tissue impedance values.
Figure 12:
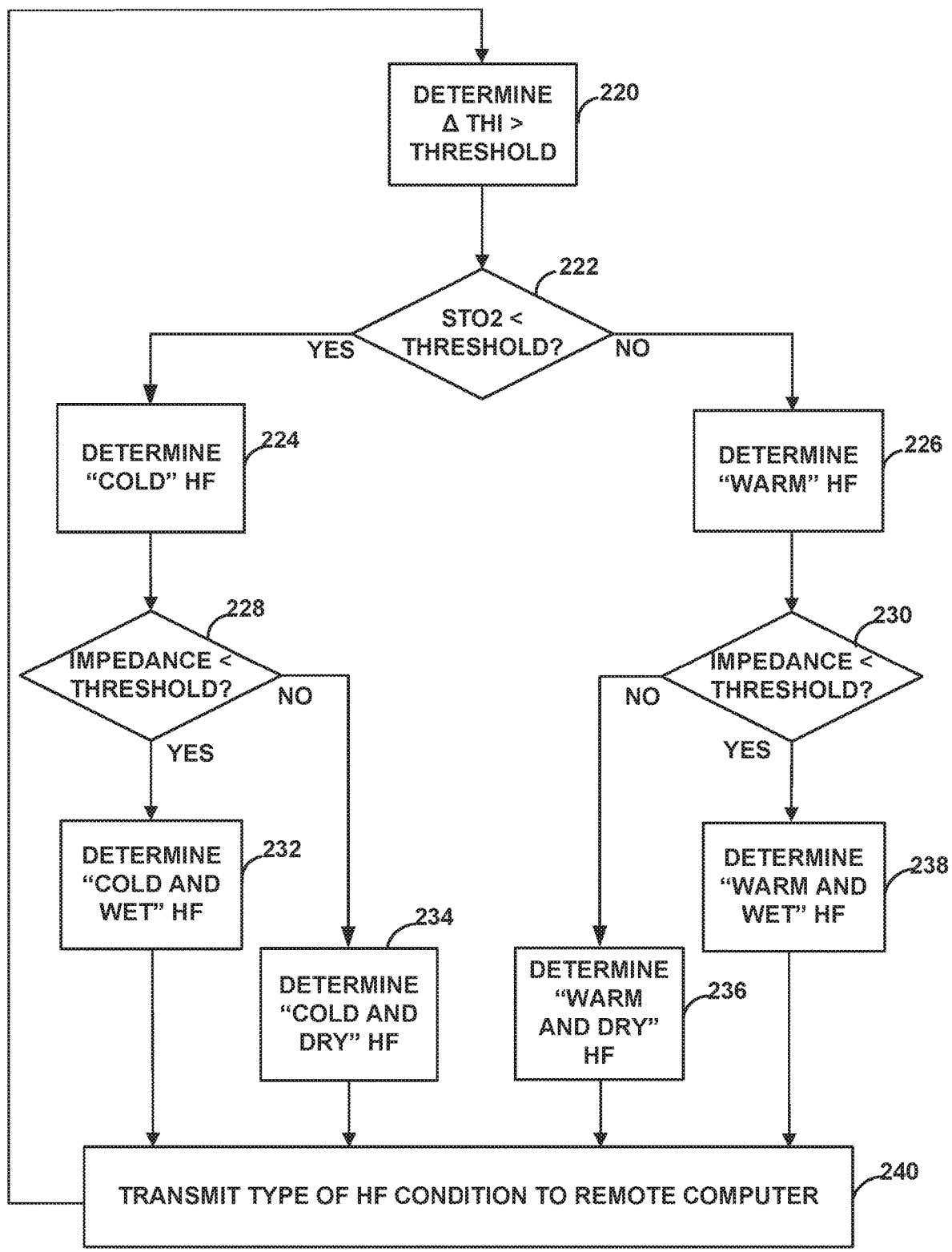
FIG. 12 is a flow diagram illustrating an example technique for determining a type of a heart failure condition of a patient based on current values of the patient's tissue oxygen saturation and tissue impedance.

FIGS. 10-12 are flow diagrams illustrating example techniques for cross-referencing current values of two or more parameters that each may be associated with cardiac and lung functions of patient 4. The outputs of the techniques illustrated FIGS. 10 and 11 indicate whether changes have occurred in the cardiac and/or lung functions of patient 4, whereas the output of the technique illustrated in FIG. 12 indicates a type of a heart failure condition of patient 4. In some examples, one or more of IMD 10, external device 12, or a clinician may use the flow diagrams of FIGS. 10-12, in conjunction with the health status and one or more current values of patient 4, to diagnose patient 4 by differentiating heart failure conditions from pulmonary disorders and to determine instructions for a medical intervention for patient 4. However, for the sake of clarity, the flow diagrams of FIGS. 10-12 are described below from the perspective of IMD 10, of which processing circuitry 50 may be configured to carry out the decisions illustrated in FIGS. 10-12.

FIG. 10 is a flow diagram illustrating an example technique for determining whether one or both of the lung and cardiac functions of patient 4 have changed, based on comparisons of current $SpO_2$ and HR and/or HRV values of patient 4 to corresponding baseline values and thresholds. In some examples, the technique illustrated in FIG. 10 may enable differential diagnosis between cardiac and pulmonary disorders, such as by identifying one or both of a heart failure condition and pulmonary disorder as being a cause of a symptom experienced by patient 4 (e.g., shortness of breath) that may be associated with one or both of a heart failure condition and a pulmonary disorder. As described above, $SpO_2$ values may be an approximation of $SaO_2$, which is associated with lung function. However, $SaO_2$ values may be affected by a congestions status of patient 4. For example, increases in congestion may be caused by heart failure progression, but may result in a decrease in $SaO_2$ values (and, by extension, in $SpO_2$ values). Thus, it may be desirable to distinguish between the effect of lung function on $SpO_2$ values and the effect of cardiac function on $SpO_2$ values, such as by cross-referencing a current $SpO_2$ value of patient 4 with current HR and HRV values of patient 4. HR and HRV values may be more closely associated with cardiac function than with lung function. Thus, by cross-referencing values of $SpO_2$ with HR and/or HRV, processing circuitry 50 of IMD 10 may assess both the cardiac and lung functions of patient 4, thereby providing an added layer of confidence to the determined heart failure and pulmonary statuses of patient 4 shown in FIG. 6. Moreover, HR and/or HRV may provide additional information about the cardiac function of patient 4, which processing circuitry 50 of IMD 10 may use in a technique for determining a heart failure status of patient 4.

At the top of the flow chart of FIG. 10, processing circuitry 50 of IMD 10 determines a current $SpO_2$ value of patient 4 (160). Next, processing circuitry 50 compares the current $SpO_2$ value of patient 4 to a corresponding baseline value, and determines whether a change in the current $SpO_2$ value relative to the baseline value satisfies a threshold (162). Regardless of whether processing circuitry 50 determines that the change in the current $SpO_2$ value relative to the baseline value satisfies the threshold, processing circuitry 50 then determines current HR and HRV values of patient 4 based on ECG signals of patient 4 (164, 166). Processing circuitry 50 of IMD 10 then compares the current values of HR and HRV to corresponding baseline values, and determines whether differences between one or both of the current values of HR and HRV and the baseline values satisfy corresponding thresholds (168, 170).

If processing circuitry 50 determines both that the difference between the current value of $SpO_2$ and the corresponding baseline value satisfies a threshold and that the differences between one or both of the current values of HR and HRV and the baseline values satisfy corresponding thresholds, then processing circuitry 50 determines that both the cardiac and lung functions of patient 4 have changed (172). In some such examples, processing circuitry 50 also may determine the relative contributions of a heart failure condition and a pulmonary disorder in causing a symptom experienced by patient 4. For example, if the change in lung function is substantially greater than the change in cardiac function, then processing circuitry 50 may determine that the pulmonary disorder is a primary cause of the symptom and/or may determine the relative contributions of the heart failure condition and the pulmonary disorder in causing the symptom. If processing circuitry 50 determines that the difference between the current value of $SpO_2$ and the corresponding baseline value satisfies a threshold but that the differences between the current values of HR and HRV and the corresponding baseline values do not satisfy corresponding thresholds, then processing circuitry 50 determines that the lung function of patient 4 has changed (174). If processing circuitry 50 determines that the difference between the current value of $SpO_2$ and the corresponding baseline value does not satisfy a threshold but that the differences between one or both of the current values of HR and HRV and the corresponding baseline values do satisfy corresponding thresholds, then processing circuitry determines that the cardiac function of patient 4 has changed (176). If processing circuitry 50 determines both that the difference between both the current value of $SpO_2$ and the corresponding baseline value does not satisfy a threshold and that one or both of the differences between the current values of HR and HRV and the baseline values do not satisfy corresponding thresholds, then processing circuitry determines that both the cardiac and lung functions of patient 4 have not changed (178). Processing circuitry 50 then transmits an indication of the change or stability of the cardiac and lung functions of patient 4 to external device 12 (180), which may include the transmitted information in a determination of a health status of patient 4 and/or in determining a medical intervention for patient 4 based on considerations similar to those described above. In some such examples, the health status of patient 4 may include a diagnostic indication, such as an indication that patient 4 has one or both of a heart failure condition and a pulmonary disorder, an indication that such condition(s) have progressed, or an indication that a symptom experienced by patient 4 is being caused by one or both of a heart failure condition and/or a pulmonary disorder. In examples in which both the cardiac and lung functions of patient 4 has changed, the health status also may include an indication of the relative contributions of the heart failure condition and the pulmonary disorder in causing the symptom. In other examples, a clinician may make a differential diagnosis pertaining to cardiac and pulmonary disorders of patient 4 based on the health status of patient 4.

FIG. 11 is a flow diagram illustrating another example technique for determining whether one or both of the lung and cardiac functions of patient 4 have changed, based on comparisons of current $StO_2$ and Z values of patient 4 to corresponding baseline values and thresholds. In some examples, the technique illustrated in FIG. 11 may enable differential diagnosis between cardiac and pulmonary disorders, such as by identifying one or both of a heart failure condition and pulmonary disorder as being a cause of a symptom experienced by patient 4 (e.g., shortness of breath) that may be associated with one or both of a heart failure condition and a pulmonary disorder. As described above, $StO_2$ values are indicative of both $SvO_2$ and $SaO_2$, the latter of which may be associated with both cardiac and lung functions. However, Z values may be more closely associated with cardiac function than with lung function. Thus, by cross-referencing a current $StO_2$ value with a current Z value, processing circuitry 50 of IMD 10 may assess both the cardiac and lung functions of patient 4, thereby providing an added layer of confidence to the determined heart failure and pulmonary statuses of patient 4 shown in FIG. 6. Moreover, a current Z value may provide additional information about the cardiac function of patient 4, which processing circuitry 50 of IMD 10 may use in a technique for determining a heart failure status of patient 4.

At the top of the flow chart of FIG. 11, processing circuitry 50 of IMD 10 determines a current $StO_2$ value of patient 4 (190). Next, processing circuitry 50 compares the current $StO_2$ value of patient 4 to a corresponding baseline value, and determines whether a change in the current $StO_2$ value relative to the baseline value satisfies a threshold (192). Regardless of whether processing circuitry 50 determines that the change in the current $StO_2$ value relative to the baseline value satisfies the threshold, processing circuitry 50 then determines a current Z value of patient 4 based on signals received from two or more electrodes 38A-38D (194, 196). Processing circuitry 50 of IMD 10 then compares the current Z value to a corresponding baseline value, and determines whether a difference between the current Z value and the baseline value satisfies a corresponding threshold (198, 200).

If processing circuitry 50 determines both that the difference between the current $StO_2$ value and the corresponding baseline value satisfies a threshold and that the difference between the current Z value and the corresponding baseline value satisfies a threshold, then processing circuitry determines that both the cardiac and lung functions of patient 4 have changed (202). In some such examples, processing circuitry 50 also may determine the relative contributions of a heart failure condition and a pulmonary disorder in causing a symptom experienced by patient 4. For example, if the change in lung function is substantially greater than the change in cardiac function, then processing circuitry 50 may determine that the pulmonary disorder is a primary cause of the symptom and/or may determine the relative contributions of the heart failure condition and the pulmonary disorder in causing the symptom. If processing circuitry 50 determines that the difference between the current $StO_2$ value and the corresponding baseline value satisfies the threshold but that the difference between the current Z value and the corresponding baseline value do not satisfy the threshold, then processing circuitry determines that the lung function of patient 4 has changed (204). If processing circuitry 50 determines that the difference between the current $StO_2$ value and the corresponding baseline value does not satisfy a threshold but that the difference between the current Z value and the corresponding baseline value does satisfy the threshold, then processing circuitry determines that the cardiac function of patient 4 has changed (206). If processing circuitry 50 determines both that the difference between both the current $StO_2$ value and the corresponding baseline value does not satisfy a threshold and that the difference between the current Z value and the corresponding baseline value do not satisfy the threshold, then processing circuitry determines that both the cardiac and lung functions of patient 4 have not changed (208). Processing circuitry 50 then transmits an indication of the change or stability of the cardiac and lung functions of patient 4 to external device 12 (210), which may include the transmitted information in a determination of a health status of patient 4 and/or in determining a medical intervention for patient 4 based on considerations similar to those described above. In some such examples, the health status of patient 4 may include a diagnostic indication, such as an indication that patient 4 has one or both of a heart failure condition and a pulmonary disorder, an indication that such condition(s) have progressed, or an indication that a symptom experienced by patient 4 is being caused by one or both of a heart failure condition and/or a pulmonary disorder. In examples in which both the cardiac and lung functions of patient 4 has changed, the health status also may include an indication of the relative contributions of the heart failure condition and the pulmonary disorder in causing the symptom. In other examples, a clinician may make a differential diagnosis pertaining to cardiac and pulmonary disorders of patient 4 based on the health status of patient 4.

FIG. 12 is a flow diagram illustrating a technique for determining a type of a heart failure condition of patient 4 by differentiating types of heart failure conditions, based on comparisons of current $StO_2$ and Z values of patient 4 to corresponding baseline values and thresholds. In some examples, the example technique illustrated in FIG. 12 may be carried out when processing circuitry 50 has determined that an anemia status of patient 4 indicates that patient 4 is anemic. However, the technique illustrated in FIG. 12 may be carried out in other situations, such as when one of the techniques in FIG. 10 or 11 indicates that a cardiac function of patient 4 has changed. In some examples, heart failure conditions may be classified based on the tissue perfusion and congestions statuses of patient 4. Determining a type of heart failure condition of patient 4 may enable external device 12 to determine an appropriate medical intervention for patient 4, and may be indicative of the progression of a heart failure condition of patient 4 from one type to another. In some examples, processing circuitry 50 may assign different values to the different types of heart failure conditions shown in FIG. 12, such that a diagnostic score of patient 4 may be based, in part, on which type of heart failure condition patient 4 may have.

At the top of the flow chart of FIG. 12, processing circuitry 50 of IMD 10 determines that a difference between a current THI value of patient 4 and a corresponding baseline value satisfies a corresponding threshold (220). Next, processing circuitry 50 determines a current $StO_2$ value of patient 4 and determines whether the current $StO_2$ value satisfies a threshold (222). If processing circuitry 50 determines that the current $StO_2$ value does not satisfy the threshold, processing circuitry 50 then determines that patient 4 has "cold" heart failure, which indicates that patient 4 has inadequate tissue perfusion (224). If processing circuitry 50 determines that the current $StO_2$ value satisfies the threshold, processing circuitry 50 then determines that patient 4 has "warm" heart failure, which indicates that patient 4 has adequate tissue perfusion (226). Regardless of whether patient 4 has "cold" or "warm" heart failure, processing circuitry 50 then determines a current Z value of patient 4 (228, 230). Processing circuitry 50 of IMD 10 then determines whether the current Z value satisfies a threshold (228, 230).

In cases in which processing circuitry 50 has determined that patient 4 has "cold" heart failure and that the current Z value is less than the threshold, processing circuitry determines that patient 4 has "cold and wet" heart failure (232), in which the "wet" designation indicates that the patient is congested. In cases in which processing circuitry 50 has determined that patient 4 has "cold" heart failure and that the current Z value is not less than the threshold, processing circuitry determines that patient 4 has "cold and dry" heart failure (234), in which the "dry" designation indicates that patient 4 is not congested. In cases in which processing circuitry 50 has determined that patient 4 has "warm" heart failure and that the current Z value is not less than the threshold, processing circuitry determines that patient 4 has "warm and dry" heart failure (236). In cases in which processing circuitry 50 has determined that patient 4 has "warm" heart failure and that the current Z value is less than the threshold, processing circuitry determines that patient 4 has "warm and wet" heart failure (238). Processing circuitry 50 then transmits an indication of the change or stability of the cardiac and lung functions of patient 4 to external device 12 (240), which may include the transmitted information in a determination of a health status of patient 4 and/or in determining a medical intervention for patient 4. In some such examples, the health status of patient 4 may include a diagnostic indication, such as an indication that patient 4 has a particular, current type of heart failure condition and/or an indication that a heart failure condition of patient 4 has progressed from a previous type to the current type. In other examples, a clinician may make a differential diagnosis pertaining to a current type and/or a progression of a heart failure condition of patient 4 based on the health status of patient 4.

In some examples, some of the medical interventions that external device 12 may recommend based on one status of patient 4 may be conditioned on another status of patient 4. For example, some medical interventions for a heart failure condition may be conditioned upon a pulmonary status of patient 4. Thus, in determining which medical interventions to instruct patient 4 to undertake, external device 12 may take into account all three of the cardiac, pulmonary, and anemia statuses of patient 4. In this manner, the methods and systems described herein may provide robust treatment for one or more of a heart failure condition, a pulmonary disorder, and/or anemia by taking into account multiple parameters of the cardiac, lung, and blood functions of patient 4.

Although processing circuitry 50 of IMD 10 and processing circuitry of external device 12 is described above as being configured to perform one or more of the steps of the techniques illustrated in FIGS. 6-12, any steps of the techniques described herein may be performed by processing circuitry of the other of IMD 10 or external device 12, or by one or more other devices. For example, processing circuitry of external device 12, or of any other suitable implantable or external device or server, may be configured to perform one or more of the steps described as being performed by processing circuitry 50 of IMD 10. In other examples, processing circuitry 50 of IMD 10, or of any other suitable implantable or external device or server, may be configured to perform one or more of the steps described as being performed by processing circuitry of external device 12. Such other implantable or external devices may include, for example, an implantable pacemaker or ICD, an external monitoring device, or any other suitable device. In addition, although the optical sensors and electrodes are described herein as being positioned on a housing of IMD 10, in other examples, such optical sensors and/or electrodes may be positioned on a housing of another device implanted in or external to patient 4, such as a transvenous, subcutaneous, or extravascular pacemaker or ICD, or coupled to such a device by one or more leads.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the terms "processor" or "processing circuitry" as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:

1. A method for determining a health status of a patient using an implantable medical device configured for subcutaneous implantation outside of a thorax of the patient, the implantable medical device comprising at least one optical sensor, the method comprising, by processing circuitry of a medical device system comprising the implantable medical device:

identifying one or more symptoms of the patient;

determining a current tissue oxygen saturation value of the patient based on a first signal received from the at least one optical sensor;

determining a current pulsatile oxygen saturation value of the patient based on a second signal received from the at least one optical sensor;

determining a current heart rate of the patient based on a cardiac electrogram signal received from at least two of a plurality of electrodes;

determining a current heart rate variability value based on the cardiac electrogram signal;

determining a current tissue impedance value of the patient based on a subcutaneous tissue impedance signal received from at least two of the plurality of electrodes;

comparing the current tissue oxygen saturation value to a baseline tissue oxygen saturation value;

comparing the current pulsatile oxygen saturation value to the baseline pulsatile oxygen saturation value;

comparing the current heart rate to a baseline heart rate;

comparing the current heart rate variability value to a baseline heart rate variability value;

comparing the current tissue impedance value to a baseline tissue impedance value;

determining a heart failure status of the patient based on the comparison of the current tissue oxygen saturation value to the baseline tissue oxygen saturation value;

determining a pulmonary status of the patient based on the comparison of the current pulsatile oxygen saturation value of the patient to the baseline pulsatile oxygen saturation value; and determining the health status of the patient based on a combination of the heart failure status and the pulmonary status of the patient, wherein determining the health status of the patient based on the combination of the heart failure status and the pulmonary status of the patient comprises providing an indication of which of the heart failure status or the pulmonary status is a cause of the one or more symptoms of the patient, and wherein determining the heart failure status of the patient and determining the pulmonary status of the patient comprises:

determining, based on comparing the current heart rate to the baseline heart rate and comparing the current heart rate variability value to the baseline heart rate variability value, whether a difference between the current pulsatile oxygen saturation value and the baseline pulsatile oxygen saturation value is caused by one or both of a change in a lung function of the patient or a change in a cardiac function of the patient; and determining, based on comparing the current tissue impedance value to the baseline tissue impedance value, whether a difference between the current tissue oxygen saturation value and the baseline tissue oxygen saturation value is caused by one or both of a change in a lung function of the patient or a change in a cardiac function of the patient.

2. The method of claim 1, wherein comparing the current tissue oxygen saturation value to a baseline tissue oxygen saturation value and comparing the current pulsatile oxygen saturation value to the baseline pulsatile oxygen saturation value comprises:

determining whether the difference between the current tissue oxygen saturation value and the baseline tissue oxygen saturation value satisfies a tissue oxygen saturation threshold value that is associated with a change in the cardiac function of the patient; and determining whether the difference between the current pulsatile oxygen saturation value and the baseline pulsatile oxygen saturation value satisfies a pulsatile oxygen saturation threshold value that is associated with a change in the lung function of the patient.

3. The method of claim 1, wherein the medical device further comprises the plurality of electrodes, and wherein determining the heart failure status of the patient and the pulmonary status of the patient further comprises:

determining a congestion status of the patient by determining whether a difference between the current tissue impedance value and the baseline tissue impedance value satisfies a tissue impedance threshold value.

4. The method of claim 1, further comprising:

determining a current tissue hemoglobin index value of the patient based on a third signal received from the at least one optical sensor;

comparing the current tissue hemoglobin index value to a baseline tissue hemoglobin index value by determining whether a difference between the current tissue hemoglobin index value and the baseline tissue hemoglobin index value satisfies a tissue hemoglobin index threshold value that is associated with a change in a red blood cell count of the patient; and determining an anemia status of the patient based on the comparison of the current tissue hemoglobin index value to the baseline tissue hemoglobin index value, wherein determining the health status of the patient further comprises determining the health status of the patient based on the anemia status of the patient.

5. The method of claim 4, wherein determining the anemia status of the patient comprises determining that the patient is anemic, and wherein determining the heart failure status of the patient further comprises:

determining whether the difference between the current tissue oxygen saturation value and the baseline tissue oxygen saturation value satisfies a tissue oxygen saturation threshold value that is associated with a change in a cardiac function of the patient; and determining a type of a heart failure condition of the patient based on the difference between the current tissue oxygen saturation value and the baseline tissue oxygen saturation value and a congestion status of the patient.

6. The method of claim 1, further comprising, by the processing circuitry:

transmitting the health status of the patient to a remote computer;

receiving, from the remote computer, instructions for a medical intervention based on the health status of the patient; and transmitting the instructions for the medical intervention to a user device.

7. The method of claim 6, wherein the instructions for the medical intervention comprise at least one of a change in a drug selection, a change in a drug dosage, instructions to schedule a visit with a clinician, or instructions for the patient to seek medical attention.

8. The method of claim 1, wherein determining the health status of the patient based on the combination of the heart failure status and the pulmonary status of the patient comprises determining, by the processing circuitry, a diagnostic score based on the combination, wherein the diagnostic score is associated with a likelihood that the patient will experience an adverse medical event.

9. The method of claim 1, wherein determining the heart failure status comprises determining a heart failure score, wherein determining the pulmonary status comprises determining a pulmonary score, and wherein the method further comprises:

comparing the heart failure score to the pulmonary score; and providing, based on the comparison of the heart failure score and the pulmonary score, an indication of which of the heart failure score or the pulmonary score is associated with a cause of the one or more symptoms of the patient.

10. The method of claim 9, wherein the heart failure score comprises a likelihood that the one or more symptoms of the patient is partially or fully caused by a heart failure condition and the pulmonary score comprises a likelihood that the one or more symptoms of the patient is partially or fully caused by a pulmonary disorder.

11. The method of claim 1, wherein the implantable medical device comprises a housing configured for subcutaneous implantation outside the thorax, and wherein the at least one optical sensor is positioned on the housing.

12. The method of claim 1, wherein the implantable medical device comprises a leadless implantable medical device.

13. A system for determining a health status of a patient using an implantable medical device configured for subcutaneous implantation outside of a thorax of the patient, the system comprising:

the implantable medical device comprising at least one optical sensor; and processing circuitry configured to:

identify one or more symptoms of the patient;

determine a current tissue oxygen saturation value of the patient based on a first signal received from the at least one optical sensor;

determine a current pulsatile oxygen saturation value of the patient based on a second signal received from the at least one optical sensor;
determine a current heart rate of the patient based on a cardiac electrogram signal received from at least two of a plurality of electrodes;
determine a current heart rate variability value based on the cardiac electrogram signal;
determine a current tissue impedance value of the patient based on a subcutaneous tissue impedance signal received from at least two of the plurality of electrodes;
compare the current tissue oxygen saturation value to a baseline tissue oxygen saturation value;
compare the current pulsatile oxygen saturation value to the baseline pulsatile oxygen saturation value;
compare the current heart rate to a baseline heart rate;
compare the current heart rate variability value to a baseline heart rate variability value;
compare the current tissue impedance value to a baseline tissue impedance value;
determine a heart failure status of the patient based on the comparison of the current tissue oxygen saturation value to the baseline tissue oxygen saturation value;
determine a pulmonary status of the patient based on the comparison of the current pulsatile oxygen saturation value of the patient to the baseline pulsatile oxygen saturation value; and
determine the health status of the patient based on a combination of the heart failure status and the pulmonary status of the patient,
wherein to determine the health status of the patient based on the combination of the heart failure status and the pulmonary status of the patient, the processing circuitry is configured to provide an indication of which of the heart failure status or the pulmonary status is a cause of the one or more symptoms of the patient, and
wherein to determine the heart failure status of the patient and to determine the pulmonary status of the patient, the processing circuitry is configured to:
determine, based on comparing the current heart rate to the baseline heart rate and comparing the current heart rate variability value to the baseline heart rate variability value, whether a difference between the current pulsatile oxygen saturation value and the baseline pulsatile oxygen saturation value is caused by one or both of a change in a lung function of the patient or a change in a cardiac function of the patient; and
determine, based on comparing the current tissue impedance value to the baseline tissue impedance value, whether a difference between the current tissue oxygen saturation value and the baseline tissue oxygen saturation value is caused by one or both of a change in a lung function of the patient or a change in a cardiac function of the patient.

14. The system of claim 13,
wherein the processing circuitry is configured to compare the current tissue oxygen saturation value to the baseline tissue oxygen saturation value and compare the current pulsatile oxygen saturation value to the baseline pulsatile oxygen saturation value by:
determining whether the difference between the current tissue oxygen saturation value and the baseline tissue oxygen saturation value satisfies a tissue oxygen saturation threshold value that is associated with a change in the cardiac function of the patient; and
determining whether the difference between the current pulsatile oxygen saturation value and the baseline pulsatile oxygen saturation value satisfies a pulsatile oxygen saturation threshold value that is associated with a change in the lung function of the patient.

15. The system of claim 13, wherein the medical device further comprises the plurality of electrodes, and wherein the processing circuitry is configured to determine the heart failure status of the patient and the pulmonary status of the patient by:
determining a congestion status of the patient by determining whether a difference between the current tissue impedance value and the baseline tissue impedance value satisfies a tissue impedance threshold value.

16. The system of claim 13, wherein the processing circuitry is further configured to:
determine a current tissue hemoglobin index value of the patient based on a third signal received from the at least one optical sensor;
compare the current tissue hemoglobin index value to a baseline tissue hemoglobin index value by determining whether a difference between the current tissue hemoglobin index value and the baseline tissue hemoglobin index value satisfies a tissue hemoglobin index threshold value that is associated with a change in a red blood cell count of the patient; and
determine an anemia status of the patient based on the comparison of the current tissue hemoglobin index value to the baseline tissue hemoglobin index value,
wherein the processing circuitry is configured to determine the health status of the patient by determining the health status of the patient based on the anemia status of the patient.

17. The system of claim 16, wherein the anemia status of the patient comprises an indication that the patient is anemic, and wherein the processing circuitry is further configured to:
determine whether the difference between the current tissue oxygen saturation value and the baseline tissue oxygen saturation value satisfies a tissue oxygen saturation threshold value that is associated with a change in a cardiac function of the patient; and
determine a type of a heart failure condition of the patient based on the difference between the current tissue oxygen saturation value and the baseline tissue oxygen saturation value and a congestion status of the patient.

18. The system of claim 13, further comprising an implantable pressure sensing device configured for implantation within a pulmonary artery of the patient and configured to determine a current pulmonary artery pressure value of the patient and transmit the pulmonary artery pressure to the implantable medical device, wherein the processing circuitry is further configured to:
compare the current pulmonary artery pressure to a baseline pulmonary artery pressure; and
determine the heart failure status of the patient based on the comparison of the current pulmonary artery pressure value to the baseline pulmonary artery pressure value.

19. The system of claim 13, wherein the processing circuitry is further configured to:
transmit the health status of the patient to a remote computer;
receive, from the remote computer, instructions for a medical intervention based on the health status of the patient; and transmit the instructions for the medical intervention to a user interface.

20. The system of claim 19, wherein the instructions for the medical intervention comprise at least one of a change in a drug selection, a change in a drug dosage, instructions to schedule a visit with a clinician, or instructions for the patient to seek medical attention.

21. The system of claim 13, wherein the processing circuitry is configured to determine the health status of the patient based on the combination of the heart failure status and the pulmonary status of the patient by determining a diagnostic score based on the combination, wherein the diagnostic score is associated with a likelihood that the patient will experience an adverse medical event.

22. The system of claim 13,
wherein to determine the heart failure status, the processing circuitry is configured to determine a heart failure score,
wherein to determine the pulmonary status, the processing circuitry is configured to determining a pulmonary score, and wherein the method further comprises:
comparing the heart failure score to the pulmonary score; and
providing, based on the comparison of the heart failure score and the pulmonary score, an indication of which of the heart failure score or the pulmonary score is associated with a cause of the one or more symptoms of the patient.

23. The system of claim 22, wherein the heart failure score comprises a likelihood that the one or more symptoms of the patient is partially or fully caused by a heart failure condition, the pulmonary score comprises a likelihood that the one or more symptoms of the patient is partially or fully caused by a pulmonary disorder.

24. The system of claim 13, wherein the implantable medical device comprises a housing configured for subcutaneous implantation outside the thorax, and wherein the at least one optical sensor is positioned on the housing.

25. The system of claim 13 wherein the implantable medical device comprises the processing circuitry.

26. The system of claim 13, wherein the implantable medical device comprises a leadless implantable medical device.

27. A system for determining a health status of a patient using an implantable medical device configured for subcutaneous implantation outside of a thorax of the patient, the system comprising:
the implantable medical device comprising at least one optical sensor; and
processing circuitry configured to:
identify one or more symptoms of the patient;
determine a current tissue oxygen saturation value of the patient based on a first signal received from the at least one optical sensor;
determine a current pulsatile oxygen saturation value of the patient based on a second signal received from the at least one optical sensor;
determine a current tissue hemoglobin index value of the patient based on a third signal received from the at least one optical sensor;
determine a current heart rate of the patient based on a cardiac electrogram signal received from at least two of a plurality of electrodes;
determine a current heart rate variability value based on the cardiac electrogram signal;
determine a current tissue impedance value of the patient based on a subcutaneous tissue impedance signal received from at least two of the plurality of electrodes;
compare the current tissue oxygen saturation value to a baseline tissue oxygen saturation value;
compare the current pulsatile oxygen saturation value to a baseline pulsatile oxygen saturation value;
compare the current tissue hemoglobin index value to a baseline tissue hemoglobin index value;
compare the current heart rate to a baseline heart rate;
compare the current heart rate variability value to a baseline heart rate variability value;
compare the current tissue impedance value to a baseline tissue impedance value;
determine whether a difference between the current tissue oxygen saturation value and the baseline tissue oxygen saturation value satisfies a tissue oxygen saturation threshold value that is associated with a change in a cardiac function of the patient;
determine whether a difference between the current pulsatile oxygen saturation value and the baseline pulsatile oxygen saturation value satisfies a pulsatile oxygen saturation threshold value that is associated with a change in a lung function of the patient; and
determine whether a difference between the current tissue hemoglobin index value and the baseline tissue hemoglobin index value satisfies a tissue hemoglobin index threshold value that is associated with a change in a red blood cell count of the patient;
determine a heart failure status of the patient based on the comparison of the current tissue oxygen saturation value to the baseline tissue oxygen saturation value;
determine a pulmonary status of the patient based on the comparison of the current pulsatile oxygen saturation value of the patient to the baseline pulsatile oxygen saturation value;
determine an anemia status of the patient based on the comparison of the current tissue hemoglobin index value to the baseline tissue hemoglobin index value;
determine the health status of the patient based on a combination of the heart failure status, the pulmonary status, and the anemia status of the patient,
wherein to determine the health status of the patient based on the combination of the heart failure status, the pulmonary status, and the anemia status, the processing circuitry is configured to provide an indication of which one or more of the heart failure status, the pulmonary status, or the anemia status is a cause of the one or more symptoms of the patient, and
wherein to determine the heart failure status of the patient and to determine the pulmonary status of the patient, the processing circuitry is configured to:
determine, based on comparing the current heart rate to the baseline heart rate and comparing the current heart rate variability value to the baseline heart rate variability value, whether the difference between the current pulsatile oxygen saturation value and the baseline pulsatile oxygen saturation value is caused by one or both of a change in a lung function of the patient or a change in a cardiac function of the patient; and
determine, based on comparing the current tissue impedance value to the baseline tissue impedance value, whether the difference between the current tissue oxygen saturation value and the baseline tissue oxygen saturation value is caused by one or both of a change in a lung function of the patient or a change in a cardiac function of the patient; and transmit the health status of the patient to a remote computer, wherein the remote computer comprises processing circuitry configured to:
receive the health status of the patient transmitted by the processing circuitry of the implantable medical device;
determine instructions for a medical intervention based on the health status of the patient; and
transmit the instructions for the medical intervention to a user device.

28. A system for determining a health status of a patient, the system comprising:
means for identifying one or more symptoms of the patient;
means for determining a current tissue oxygen saturation value of the patient based on a first signal received from at least one optical sensor;
means for determining a current pulsatile oxygen saturation value of the patient based on a second signal received from the at least one optical sensor;
means for determining a current heart rate of the patient based on a cardiac electrogram signal received from at least two of a plurality of electrodes;
means for determining a current heart rate variability value based on the cardiac electrogram signal;
means for determining a current tissue impedance value of the patient based on a subcutaneous tissue impedance signal received from at least two of the plurality of electrodes;
means for comparing the current tissue oxygen saturation value to a baseline tissue oxygenation oxygen saturation value;
means for comparing the current pulsatile oxygen saturation value to the baseline pulsatile oxygen saturation value;
means for comparing the current heart rate to a baseline heart rate;
means for comparing the current heart rate variability value to a baseline heart rate variability value;
means for comparing the current tissue impedance value to a baseline tissue impedance value;
means for determining a heart failure status of the patient based on the comparison of the current tissue oxygen saturation value to the baseline tissue oxygen saturation value;
means for determining a pulmonary status of the patient based on the comparison of the current pulsatile oxygen saturation value of the patient to the baseline pulsatile oxygen saturation value; and
means for determining the health status of the patient based on a combination of the heart failure status and the pulmonary status of the patient,
wherein the means for determining the health status of the patient based on the combination of the heart failure status and the pulmonary status of the patient comprises means for providing an indication of which of the heart failure status or the pulmonary status is a cause of the one or more symptoms of the patient, and
wherein the means for determining the heart failure status of the patient and the means for determining the pulmonary status of the patient comprises:
means for determining, based on comparing the current heart rate to the baseline heart rate and comparing the current heart rate variability value to the baseline heart rate variability value, whether a difference between the current pulsatile oxygen saturation value and the baseline pulsatile oxygen saturation value is caused by one or both of a change in a lung function of the patient or a change in a cardiac function of the patient; and
means for determining, based on comparing the current tissue impedance value to the baseline tissue impedance value, whether a difference between the current tissue oxygen saturation value and the baseline tissue oxygen saturation value is caused by one or both of a change in a lung function of the patient or a change in a cardiac function of the patient.

29. The system of claim 28,
wherein the means for comparing the current tissue oxygen saturation value to a baseline tissue oxygen saturation value and the means for comparing the current pulsatile oxygen saturation value to the baseline pulsatile oxygen saturation value comprises:
means for determining whether the difference between the current tissue oxygen saturation value and the baseline tissue oxygen saturation value satisfies a tissue oxygen saturation threshold value that is associated with a change in the cardiac function of the patient; and
means for determining whether the difference between the current pulsatile oxygen saturation value and the baseline pulsatile oxygen saturation value satisfies a pulsatile oxygen saturation threshold value that is associated with a change in the lung function of the patient.

30. A non-transitory computer-readable medium storing instructions for causing processing circuitry to perform a method for determining a health status of a patient using an implantable medical device configured for subcutaneous implantation outside of a thorax of the patient, the implantable medical device comprising at least one optical sensor, the method comprising:
identifying one or more symptoms of the patient;
determining a current tissue oxygen saturation value of the patient based on a first signal received from the at least one optical sensor;
determining a current pulsatile oxygen saturation value of the patient based on a second signal received from the at least one optical sensor;
determining a current heart rate of the patient based on a cardiac electrogram signal received from at least two of a plurality of electrodes;
determining a current heart rate variability value based on the cardiac electrogram signal;
determining a current tissue impedance value of the patient based on a subcutaneous tissue impedance signal received from at least two of the plurality of electrodes;
comparing the current tissue oxygen saturation value to a baseline tissue oxygen saturation value;
comparing the current pulsatile oxygen saturation value to the baseline pulsatile oxygen saturation value;
comparing the current heart rate to a baseline heart rate;
comparing the current heart rate variability value to a baseline heart rate variability value;
comparing the current tissue impedance value to a baseline tissue impedance value;
determining a heart failure status of the patient based on the comparison of the current tissue oxygen saturation value to the baseline tissue oxygen saturation value;

determining a pulmonary status of the patient based on the comparison of the current pulsatile oxygen saturation value of the patient to the baseline pulsatile oxygen saturation value; and determining the health status of the patient based on a combination of the heart failure status and the pulmonary status of the patient, wherein determining the health status of the patient based on the combination of the heart failure status and the pulmonary status of the patient comprises providing an indication of which of the heart failure status or the pulmonary status is a cause of the one or more symptoms of the patient, and wherein determining the heart failure status of the patient and determining the pulmonary status of the patient comprises:

determining, based on comparing the current heart rate to the baseline heart rate and comparing the current heart rate variability value to the baseline heart rate variability value, whether a difference between the current pulsatile oxygen saturation value and the baseline pulsatile oxygen saturation value is caused by one or both of a change in a lung function of the patient or a change in a cardiac function of the patient; and determining, based on comparing the current tissue impedance value to the baseline tissue impedance value, whether a difference between the current tissue oxygen saturation value and the baseline tissue oxygen saturation value is caused by one or both of a change in a lung function of the patient or a change in a cardiac function of the patient.

31. The non-transitory computer-readable medium of claim 30, wherein the method further comprises:

determining whether the difference between the current tissue oxygen saturation value and the baseline tissue oxygen saturation value satisfies a tissue oxygen saturation threshold value that is associated with a change in the cardiac function of the patient; and determining whether the difference between the current pulsatile oxygen saturation value and the baseline pulsatile oxygen saturation value satisfies a pulsatile oxygen saturation threshold value that is associated with a change in the lung function of the patient.

32. The method of claim 1, wherein determining the heart failure status of the patient and determining the pulmonary status of the patient comprises:

determining whether the difference between the current pulsatile oxygen saturation value and the baseline pulsatile oxygen saturation value satisfies a pulsatile oxygen saturation threshold value;

determining whether a difference between the current heart rate and the baseline heart rate satisfies a heart rate threshold value that is associated with a change in the cardiac function of the patient;

determining whether a difference between the current heart rate variability value and the baseline heart rate variability value satisfies a heart rate variability threshold value that is associated with a change in the cardiac function of the patient;

determining, when the difference between the current pulsatile oxygen saturation value and the baseline pulsatile oxygen saturation value satisfies the pulsatile oxygen saturation threshold value, and when the difference between the current heart rate and the baseline heart rate satisfies the heart rate threshold value or the difference between the current heart rate variability value and the baseline heart rate variability value satisfies the heart rate variability threshold value, that the difference between the current pulsatile oxygen saturation value and the baseline pulsatile oxygen saturation value is caused by both of a change in the lung function of the patient and a change in the cardiac function of the patient;

determining, when the difference between the current pulsatile oxygen saturation value and the baseline pulsatile oxygen saturation value satisfies the pulsatile oxygen saturation threshold value and when the difference between the current heart rate and the baseline heart rate does not satisfy the heart rate threshold value and the difference between the current heart rate variability value and the baseline heart rate variability value does not satisfy the heart rate variability threshold value, that the difference between the current pulsatile oxygen saturation value and the baseline pulsatile oxygen saturation value is caused by a change in the lung function of the patient;

determining, when the difference between the current pulsatile oxygen saturation value and the baseline pulsatile oxygen saturation value does not satisfy the pulsatile oxygen saturation threshold value, and when the difference between the current heart rate and the baseline heart rate satisfies the heart rate threshold value or the difference between the current heart rate variability value and the baseline heart rate variability value satisfies the heart rate variability threshold value, that the difference between the current pulsatile oxygen saturation value and the baseline pulsatile oxygen saturation value is caused by a change in the cardiac function of the patient; and determining, when the difference between the current pulsatile oxygen saturation value and the baseline pulsatile oxygen saturation value does not satisfy the pulsatile oxygen saturation threshold value and when the difference between the current heart rate and the baseline heart rate does not satisfy the heart rate threshold value and the difference between the current heart rate variability value and the baseline heart rate variability value does not satisfy the heart rate variability threshold value, that the cardiac function of the patient and the lung function of the patient have not changed.

33. The method of claim 1, wherein determining the heart failure status of the patient and determining the pulmonary status of the patient comprises:

determining whether the difference between the current tissue oxygen saturation value and the baseline tissue oxygen saturation value satisfies a tissue oxygen saturation threshold value;

determining whether a difference between the current tissue impedance value and the baseline tissue impedance value satisfies a tissue impedance threshold value that is associated with a change in the cardiac function of the patient;

determining, when the difference between the current tissue oxygen saturation value and the baseline tissue oxygen saturation value satisfies the tissue oxygen saturation threshold value, and when the difference between the current tissue impedance value and the baseline tissue impedance value satisfies the tissue impedance threshold value, that the difference between the current tissue oxygen saturation value and the baseline tissue oxygen saturation value is caused by both of a change in the lung function of the patient and a change in the cardiac function of the patient;

determining, when the difference between the current tissue oxygen saturation value and the baseline tissue oxygen saturation value satisfies the tissue oxygen saturation threshold value and when the difference between the current tissue impedance value and the baseline tissue impedance value does not satisfy the tissue impedance threshold value, that the difference between the current tissue oxygen saturation value and the baseline tissue oxygen saturation value is caused by a change in the lung function of the patient;

determining, when the difference between the current tissue oxygen saturation value and the baseline tissue oxygen saturation value does not satisfy the tissue oxygen saturation threshold value, and when the difference between the current tissue impedance value and the baseline tissue impedance value satisfies the tissue impedance threshold value, that the difference between the current tissue oxygen saturation value and the baseline tissue oxygen saturation value is caused by a change in the cardiac function of the patient; and determining, when the difference between the current tissue oxygen saturation value and the baseline tissue oxygen saturation value does not satisfy the tissue oxygen saturation threshold value and when the difference between the current tissue impedance value and the baseline tissue impedance value does not satisfy the tissue impedance threshold value, that the cardiac function of the patient and the lung function of the patient have not changed.

* * * * *